US008569484B2

(12) United States Patent
Bifulco et al.

(10) Patent No.: US 8,569,484 B2
(45) Date of Patent: Oct. 29, 2013

(54) HETEROCYCLIC UREA DERIVATIVES AND METHODS OF USE THEREOF

(75) Inventors: Neil Bifulco, Waltham, MA (US); Allison Laura Choy, Waltham, MA (US); Olga Quiroga, Waltham, MA (US); Brian Alan Sherer, Waltham, MA (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 13/322,717

(22) PCT Filed: May 28, 2010

(86) PCT No.: PCT/GB2010/050908
§ 371 (c)(1),
(2), (4) Date: Jan. 26, 2012

(87) PCT Pub. No.: WO2010/136817
PCT Pub. Date: Dec. 2, 2010

(65) Prior Publication Data
US 2012/0122817 A1  May 17, 2012

Related U.S. Application Data

(60) Provisional application No. 61/182,373, filed on May 29, 2009, provisional application No. 61/285,017, filed on Dec. 9, 2009.

(51) Int. Cl.
*C07D 471/04* (2006.01)
*C07F 9/6561* (2006.01)

(52) U.S. Cl.
USPC ............ 544/58.2; 544/127; 544/362; 546/23; 546/123

(58) Field of Classification Search
None
See application file for complete search history.

(56) References Cited

U.S. PATENT DOCUMENTS 8,283,361 B2 * 10/2012 Choy et al. .................... 514/312

FOREIGN PATENT DOCUMENTS

WO    2006/092599 A2    9/2006
WO    2008/068470 A1    6/2008

OTHER PUBLICATIONS

Richard B. Silverman, The Organic Chemistry of Drug Design and Drug Action, Chapter 2: Drug Discovery, Design, and Development, Academic Press, p. 5-51 (1992).*
International Search Report for PCT/GB2010/050908; mailed Sep. 15, 2010.

* cited by examiner

*Primary Examiner* — Janet Andres
*Assistant Examiner* — Timothy R Rozof

(57) ABSTRACT

Compounds of formula (IA) and their pharmaceutically acceptable salts are described. Processes for their preparation, pharmaceutical compositions containing them, their use as medicaments and their use in the treatment of bacterial infections are also described.

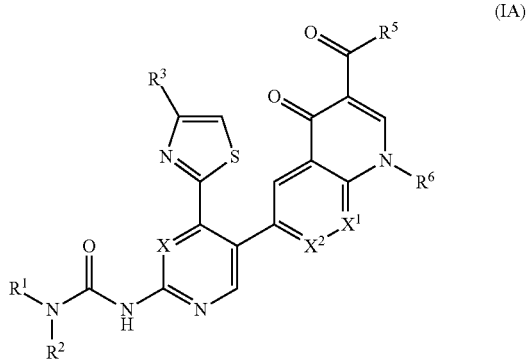

9 Claims, No Drawings

HETEROCYCLIC UREA DERIVATIVES AND METHODS OF USE THEREOF

CROSS-REFERENCE TO RELATED APPLICATIONS

This application is a US National Stage under 35 U.S.C §371 of International Application No. PCT/GB2010/050908 (filed May 28, 2010) which claims priority under 35 U.S.C. §119(e) to Application No. 61/182,373 filed on May 29, 2009 and Application No. 61/285,017 filed on Dec. 9, 2009.

FIELD OF THE INVENTION

The present invention relates to compounds which demonstrate antibacterial activity, processes for their preparation, pharmaceutical compositions containing them as the active ingredient, to their use as medicaments and to their use in the manufacture of medicaments for use in the treatment of bacterial infections in warm-blooded animals such as humans. In particular, this invention relates to compounds useful for the treatment of bacterial infections in warm-blooded animals such as humans, more particularly to the use of these compounds in the manufacture of medicaments for use in the treatment of bacterial infections in warm-blooded animals such as humans.

BACKGROUND OF THE INVENTION

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus aureus* (MRSA), methicillin resistant coagulase negative staphylococci (MRCNS), penicillin resistant *Streptococcus pneumoniae* and multiple resistant *Enterococcus faecium*.

The preferred clinically effective antibiotic for treatment of last resort of such resistant Gram-positive pathogens is vancomycin. Vancomycin is a glycopeptide and is associated with various toxicities, including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Consequently, in order to overcome the threat of widespread multi-drug resistant organisms, there is an on-going need to develop new antibiotics, particularly those with either a novel mechanism of action and/or containing new pharmacophoric groups.

Deoxyribonucleic acid (DNA) gyrase is a member of the type II family of topoisomerases that control the topological state of DNA in cells (Champoux, J. J.; 2001. Ann. Rev. Biochem. 70: 369-413). Type II topoisomerases use the free energy from adenosine triphosphate (ATP) hydrolysis to alter the topology of DNA by introducing transient double-stranded breaks in the DNA, catalyzing strand passage through the break and resealing the DNA. DNA gyrase is an essential and conserved enzyme in bacteria and is unique among topoisomerases in its ability to introduce negative supercoils into DNA. The enzyme consists of two subunits, encoded by gyrA and gyrB, forming an $A_2B_2$ tetrameric complex. The A subunit of gyrase (GyrA) is involved in DNA breakage and resealing and contains a conserved tyrosine residue that forms the transient covalent link to DNA during strand passage. The B subunit (GyrB) catalyzes the hydrolysis of ATP and interacts with the A subunit to translate the free energy from hydrolysis to the conformational change in the enzyme that enables strand-passage and DNA resealing.

Another conserved and essential type II topoisomerase in bacteria, called topoisomerase IV, is primarily responsible for separating the linked closed circular bacterial chromosomes produced in replication. This enzyme is closely related to DNA gyrase and has a similar tetrameric structure formed from subunits homologous to Gyr A and to Gyr B. The overall sequence identity between gyrase and topoisomerase IV in different bacterial species is high. Therefore, compounds that target bacterial type II topoisomerases have the potential to inhibit two targets in cells, DNA gyrase and topoisomerase IV; as is the case for existing quinolone antibacterials (Maxwell, A. 1997, Trends Microbiol. 5: 102-109).

DNA gyrase is a well-validated target of antibacterials, including the quinolones and the coumarins. The quinolones (e.g. ciprofloxacin) are broad-spectrum antibacterials that inhibit the DNA breakage and reunion activity of the enzyme and trap the GyrA subunit covalently complexed with DNA (Drlica, K., and X. Zhao, 1997, Microbiol. Molec. Biol. Rev. 61: 377-392). Members of this class of antibacterials also inhibit topoisomerase IV and as a result, the primary target of these compounds varies among species. Although the quinolones are successful antibacterials, resistance generated primarily by mutations in the target (DNA gyrase and topoisomerase IV) is becoming an increasing problem in several organisms, including *S. aureus* and *Streptococcus pneumoniae* (Hooper, D. C., 2002, The Lancet Infectious Diseases 2: 530-538). In addition, quinolones, as a chemical class, suffer from toxic side effects, including arthropathy that prevents their use in children (Lipsky, B. A. and Baker, C. A., 1999, Clin. Infect. Dis. 28: 352-364). Furthermore, the potential for cardiotoxicity, as predicted by prolongation of the $QT_c$ interval, has been cited as a toxicity concern for quinolones.

There are several known natural product inhibitors of DNA gyrase that compete with ATP for binding the GyrB subunit (Maxwell, A. and Lawson, D. M. 2003, Curr. Topics in Med. Chem. 3: 283-303). The coumarins are natural products isolated from *Streptomyces* spp., examples of which are novobiocin, chlorobiocin and coumermycin A1. Although these compounds are potent inhibitors of DNA gyrase, their therapeutic utility is limited due to toxicity in eukaryotes and poor penetration in Gram-negative bacteria (Maxwell, A. 1997, Trends Microbiol. 5: 102-109). Another natural product class of compounds that targets the GyrB subunit is the cyclothialidines, which are isolated from *Streptomyces filipensis* (Watanabe, J. et al 1994, J. *Antibiot.* 47: 32-36). Despite potent activity against DNA gyrase, cyclothialidine is a poor antibacterial agent showing activity only against some eubacterial species (Nakada, N, 1993, *Antimicrob. Agents Chemother.* 37: 2656-2661).

Synthetic inhibitors that target the B subunit of DNA gyrase and topoisomerase IV are known in the art. For example, coumarin-containing compounds are described in patent application number WO 99/35155, 5,6-bicyclic heteroaromatic compounds are described in patent application WO 02/060879, and pyrazole compounds are described in patent application WO 01/52845 (U.S. Pat. No. 6,608,087). AstraZeneca has also published certain applications describing anti-bacterial compounds: WO2005/026149, WO2006/087544, WO2006/087548, WO2006/087543, WO2006/092599, WO2006/092608, and WO2007/071965.

SUMMARY OF THE INVENTION

We have discovered a new class of compounds which are useful for inhibiting DNA gyrase and/or topoisomerase IV.

In one embodiment, according to the present invention there is provided a compound of formula (IA):

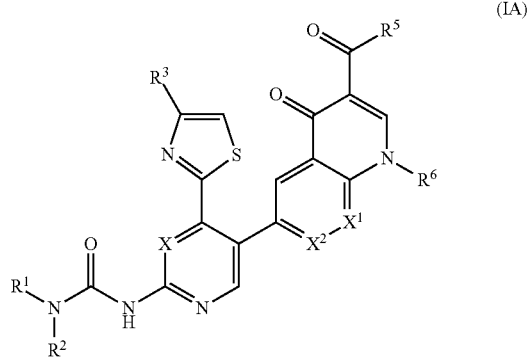

(IA)

or a pharmaceutically acceptable salt thereof, wherein:

X is N or CH;

$X^1$ is N or CH;

$X^2$ is N or $CR^{24}$, wherein only one of $X^1$ and $X^2$ is N and the other is not N;

$R^1$ is selected from $C_{1-6}$alkyl, $C_{2-6}$alkenyl, $C_{2-6}$alkynyl or $C_{3-6}$cycloalkyl; wherein $R^1$ may be optionally substituted on carbon by one or more $R^7$;

$R^2$ is selected from hydrogen or $C_{1-6}$alkyl; wherein said $C_{1-6}$alkyl may be optionally substituted by one or more groups independently selected from halo, cyano, hydroxy, nitro and amino;

or $R^1$ and $R^2$ together with the nitrogen to which they are attached form a heterocyclyl; wherein said heterocyclyl may be optionally substituted on one or more carbon atoms with one or more $R^8$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^9$;

$R^3$ is a $C_{1-6}$alkyl, a 4-7 membered-heterocyclyl or a $C_{3-14}$carbocyclyl; wherein the alkyl or carbocyclyl may be optionally substituted on one or more carbon atoms by one or more $R^{10}$;

$R^5$ is —OH, —$NH_2$, a $C_{1-6}$alkoxy, an N-($C_{1-6}$alkyl)amino, or N,N-($C_{1-6}$alkyl)$_2$amino; wherein the $C_{1-6}$alkoxy, N-($C_{1-6}$alkyl)amino, or N,N-($C_{1-6}$alkyl)$_2$amino may be optionally substituted on one or more carbon atoms with one or more, independently selected $R^{14}$;

$R^6$ is hydrogen, $C_{1-6}$alkyl, $C_{3-14}$carbocyclyl-L-, or heterocyclyl-L-; wherein $R^6$ is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$;

$R^7$, $R^8$, and $R^{10}$ are substituents on carbon which, for each occurrence, are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{3-6}$carbocyclyl or heterocyclyl; wherein $R^7$, $R^8$, and $R^{10}$, independently of each other may be optionally substituted on one or more carbon by one or more $R^{19}$; and wherein if said heterocyclyl contains an —NH— moiety that nitrogen may be optionally substituted by a group selected from $R^{20}$; and wherein if said heterocyclyl contains an =N— or a —S— moiety that nitrogen may be optionally substituted by one oxo group and that sulfur may be optionally substituted by one or two oxo groups;

$R^{14}$ and $R^{16}$ are substituents on carbon which, for each occurrence, are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{3-6}$carbocyclyl, heterocyclyl, or —OP(=O)(OR$^a$)$_2$, wherein $R^a$, for each occurrence is independently H or a $C_{1-6}$alkyl; wherein $R^{14}$ and $R^{16}$ independently of each other may be optionally substituted on one or more carbon by one or more $R^{19}$; and wherein if said heterocyclyl contains an —NH— moiety that nitrogen may be optionally substituted by a group selected from $R^{20}$; and wherein if said heterocyclyl contains an =N— or a —S— moiety that nitrogen may be optionally substituted by one oxo group and that sulfur may be optionally substituted by one or two oxo groups;

$R^9$, $R^{17}$ and $R^{20}$, for each occurrence, are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)carbamoyl, benzyl, benzyloxycarbonyl, benzoyl and phenylsulphonyl; wherein $R^9$, $R^{17}$, and $R^{20}$ independently of each other may be optionally substituted on carbon by one or more $R^{23}$;

$R^{19}$ and $R^{23}$, for each occurrence, are independently selected from halo, nitro, cyano, hydroxy, trifluoromethoxy, trifluoromethyl, phenyl, morpholinyl, piperazinyl, piperidinyl, amino, carboxy, carbamoyl, mercapto, sulphamoyl, $C_{1-6}$alkyl, $C_{1-6}$alkoxy, acetyl, acetoxy, methylamino, ethylamino, dimethylamino, diethylamino, dipropylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

$R^{24}$ is selected from the group consisting of hydrogen, halo, nitro, cyano, hydroxy, amino, mercapto, heterocyclyl, $C_{1-6}$alkyl, $C_{2-6}$alkenyl, $C_{2-6}$alkynyl, $C_{1-6}$alkoxy, N-($C_{1-6}$alkyl)amino, N,N-($C_{1-6}$alkyl)$_2$amino, and $C_{1-6}$alkylsulfanyl; wherein $R^{24}$ may be optionally substituted on one or more carbon by one or more one or more $R^{25}$; wherein if said heterocyclyl contains an —NH— moiety that nitrogen may be optionally substituted by $C_{1-6}$alkyl;

$R^{25}$ are substituents on carbon which, for each occurrence, are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{3-6}$carbocyclyl or heterocyclyl; wherein $R^{25}$ may be optionally substituted on one or more carbon by one or more $R^{26}$; and wherein if said heterocyclyl contains an —NH— moiety that nitrogen may be optionally substituted by a group selected from $R^{27}$; and wherein if said heterocyclyl contains an =N— or a —S— moiety that nitrogen may be optionally substituted by one oxo group and that sulfur may be optionally substituted by one or two oxo groups;

$R^{26}$ and $R^{28}$, for each occurrence, are independently selected from halo, nitro, cyano, hydroxy, trifluoromethoxy, trifluoromethyl, amino, carboxy, carbamoyl, mercapto, sulphamoyl, $C_{1-6}$alkyl, $C_{1-6}$alkoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

$R^{27}$, for each occurrence, is independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)$_2$carbamoyl, benzyl, benzyloxycarbonyl, benzoyl and phenylsulphonyl; wherein $R^{27}$ may be optionally substituted on carbon by one or more $R^{28}$; and L is a direct bond or a $C_{1-6}$alkylene.

In another embodiment, according to the present invention there is provided a compound of formula (I):

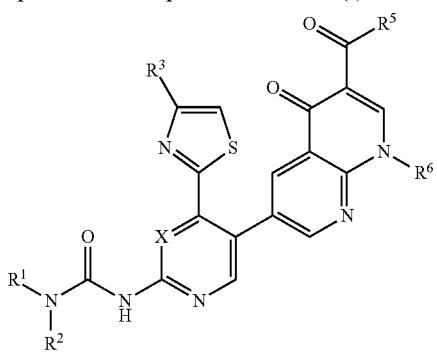

(I)

or a pharmaceutically acceptable salt thereof, wherein:

X is N or CH;

$R^1$ is selected from $C_{1-6}$alkyl, $C_{2-6}$alkenyl, $C_{2-6}$alkynyl or $C_{3-6}$cycloalkyl; wherein $R^1$ may be optionally substituted on carbon by one or more $R^7$;

$R^2$ is selected from hydrogen or $C_{1-6}$alkyl; wherein said $C_{1-6}$alkyl may be optionally substituted by one or more groups independently selected from halo, cyano, hydroxy, nitro and amino;

or $R^1$ and $R^2$ together with the nitrogen to which they are attached form a heterocyclyl; wherein said heterocyclyl may be optionally substituted on one or more carbon atoms with one or more $R^8$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^9$;

$R^3$ is an $C_{1-6}$alkyl or a $C_{3-14}$carbocyclyl; wherein the alkyl or carbocyclyl may be optionally substituted on one or more carbon atoms by one or more $R^{16}$;

$R^5$ is —OH, —NH$_2$, a $C_{1-6}$alkoxy, an N-($C_{1-6}$alkyl)amino, or N,N-($C_{1-6}$alkyl)$_2$amino; wherein the $C_{1-6}$alkoxy, N-($C_{1-6}$alkyl)amino, or N,N-($C_{1-6}$alkyl)$_2$amino may be optionally substituted on one or more carbon atoms with one or more, independently selected $R^{14}$;

$R^6$ is hydrogen, $C_{1-6}$alkyl, $C_{3-14}$carbocyclyl-L-, or heterocyclyl-L-; wherein $R^6$ is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$;

$R^7$, $R^8$, and $R^{10}$ are substituents on carbon which, for each occurrence, are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{3-6}$carbocyclyl or heterocyclyl; wherein $R^7$, $R^8$, and $R^{10}$, independently of each other may be optionally substituted on one or more carbon by one or more $R^{19}$; and wherein if said heterocyclyl contains an —NH— moiety that nitrogen may be optionally substituted by a group selected from $R^{20}$; and wherein if said heterocyclyl contains an =N— or a —S— moiety that nitrogen may be optionally substituted by one oxo group and that sulfur may be optionally substituted by one or two oxo groups;

$R^{14}$ and $R^{16}$ are substituents on carbon which, for each occurrence, are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{3-6}$carbocyclyl, heterocyclyl, or —OP(=O)(OR$^a$)$_2$, wherein R$^a$, for each occurrence is independently H or a $C_{1-6}$alkyl; wherein $R^{14}$ and $R^{16}$ independently of each other may be optionally substituted on one or more carbon by one or more $R^{19}$; and wherein if said heterocyclyl contains an —NH— moiety that nitrogen may be optionally substituted by a group selected from $R^{20}$; and wherein if said heterocyclyl contains an =N— or a —S— moiety that nitrogen may be optionally substituted by one oxo group and that sulfur may be optionally substituted by one or two oxo groups;

$R^9$, $R^{17}$ and $R^{20}$, for each occurrence, are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)$_2$carbamoyl, benzyl, benzyloxycarbonyl, benzoyl and phenylsulphonyl; wherein $R^9$, $R^{17}$, and $R^{20}$ independently of each other may be optionally substituted on carbon by one or more $R^{23}$;

$R^{19}$ and $R^{23}$, for each occurrence, are independently selected from halo, nitro, cyano, hydroxy, trifluoromethoxy, trifluoromethyl, phenyl, morpholinyl, piperazinyl, piperidinyl, amino, carboxy, carbamoyl, mercapto, sulphamoyl, $C_{1-6}$alkyl, $C_{1-6}$alkoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and L is a direct bond or a $C_{1-6}$alkylene.

In another embodiment, the invention provides pharmaceutical compositions comprising a compound represented by formula (I) or (IA), or a pharmaceutically acceptable salt thereof, and a pharmaceutically acceptable excipient or carrier.

In another embodiment, the invention provides a method of inhibiting bacterial DNA gyrase and/or bacterial topoisomerase IV in a warm-blooded animal in need of such treatment, comprising administering to the animal an effective amount of a compound represented by formula (I) or (IA), or a pharmaceutically acceptable salt thereof. In a particular embodiment, the warm-blooded animal is a human.

In another embodiment, the invention provides a method of producing an antibacterial effect in a warm-blooded animal in need of such treatment, comprising administering to the animal an effective amount of a compound represented by formula (I) or (IA), or a pharmaceutically acceptable salt thereof. In a particular embodiment, the warm-blooded animal is a human.

In another embodiment, the invention provides a method of treating a bacterial infection in a warm-blooded animal in need thereof, comprising administering to the animal an effective amount of a compound represented by formula (I) or (IA), or a pharmaceutically acceptable salt thereof. In a particular embodiment, the warm-blooded animal is a human. In one embodiment, the bacterial infection is selected from the group consisting of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci. In a particular embodiment, the warm-blooded animal is a human.

In another embodiment, the invention provides the use of a compound represented by formula (I) or (IA), or a pharmaceutically acceptable salt thereof, for the manufacture of a medicament for use in the production of an antibacterial effect in a warm-blooded animal. In a particular embodiment, the warm-blooded animal is a human.

In another embodiment, the invention provides the use of a compound represented by formula (I) or (IA), or a pharmaceutically acceptable salt thereof, for the manufacture of a medicament for use in inhibition of bacterial DNA gyrase and/or topoisomerase IV in a warm-blooded animal. In a particular embodiment, the warm-blooded animal is a human.

In another embodiment, the invention provides the use of a compound represented by formula (I) or (IA), or a pharmaceutically acceptable salt thereof, for the manufacture of a medicament for use the treatment of a bacterial infection in a warm-blooded animal. In one embodiment, the bacterial infection is selected from the group consisting of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections, Penicillin-resistant *Streptococcus pneumoniae*, methicillin-resistant *Staphylococcus aureus*, methicillin-resistant *Staphylococcus epidermidis* and Vancomycin-Resistant Enterococci. In a particular embodiment, the warm-blooded animal is a human.

In another embodiment, the invention provides a compound represented by formula (I) or (IA), or a pharmaceutically acceptable salt thereof, for use in production of an anti-bacterial effect in a warm-blooded animal.

In another embodiment, the invention provides a compound represented by formula (I) or (IA), or a pharmaceutically acceptable salt thereof, for use in inhibition of bacterial DNA gyrase and/or topoisomerase IV in a warm-blooded animal.

In another embodiment, the invention provides a compound represented by formula (I) or (IA), or a pharmaceutically acceptable salt thereof, for use in the treatment of a bacterial infection in a warm-blooded animal.

In another embodiment, the invention provides a compound represented by formula (I) or (IA), or a pharmaceutically acceptable salt thereof, for use in the treatment of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections, Penicillin-resistant *Streptococcus pneumoniae*, methicillin-resistant *Staphylococcus aureus*, methicillin-resistant *Staphylococcus epidermidis* or Vancomycin-Resistant Enterococci.

DETAILED DESCRIPTION OF THE INVENTION

In this specification the term alkyl includes both straight chained and branched saturated hydrocarbon groups. For example, "$C_{1-6}$alkyl" refers to an alkyl that has from 1 to 6 carbon atom and includes, for example, methyl, ethyl, propyl, isopropyl and t-butyl. However references to individual alkyl groups such as propyl are specific for the straight chain version only unless otherwise indicated (e.g., isopropyl). An analogous convention applies to other generic terms.

As used herein, the term "$C_{2-6}$akenyl" refers to a straight chained or branched hydrocarbon which has from 2 to 6 carbon atoms and has one or more double bond. Examples of "$C_{2-6}$alkenyl" are vinyl, allyl and 1-propenyl.

As used herein, the term "$C_{2-6}$akynyl" refers to a straight chained or branched hydrocarbon which has from 2 to 6 carbon atoms and has one or more triple bond. Examples of "$C_{2-6}$alkynyl" are ethynyl, 1-propynyl and 2-propynyl.

As used herein, the term "halo" refers to fluoro, chloro, bromo, and iodo.

A "heterocyclyl" is a saturated, partially saturated or unsaturated, mono or bicyclic ring containing 4-14 atoms of which at least one atom is chosen from nitrogen, sulphur or oxygen, which may, unless otherwise specified, be carbon or nitrogen linked, wherein a —$CH_2$— group can optionally be replaced by a —C(O)— and a ring nitrogen may be optionally substituted with one oxo to form an N-oxide and a ring sulfur may be optionally substituted with one or two oxo groups to form S-oxide(s). In one embodiment of the invention a "heterocyclyl" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked. In a further aspect of the invention a "heterocyclyl" is an unsaturated, carbon-linked, monocyclic ring containing 5 or 6 atoms of which at least one atom is chosen from nitrogen, sulphur or oxygen. Examples and suitable values of the term "heterocyclyl" are morpholinyl, piperidyl, pyridinyl, pyranyl, pyrrolyl, pyrazolyl, isothiazolyl, indolyl, quinolinyl, thienyl, 1,3-benzodioxolyl, benzothiazolyl, thiadiazolyl, oxadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, 4,5-dihydro-oxazolyl, pyrimidinyl, pyrazinyl, pyridazinyl, isoxazolyl, thiazolyl, 1H-tetrazolyl, 1H-triazolyl, N-methylpyrrolyl, 4-pyridone, quinolin-4(1H)-one, pyridin-2(1H)-one, imidazo[1,2-a]pyridinyl, 1-isoquinolone, 2-pyrrolidone, 4-thiazolidone, quinoxalinyl, 5,6-dihydro[1,3]thiazolo[4,5-d]pyridazinyl, pyridine-N-oxide and quinoline-N-oxide. Suitable examples of "a nitrogen linked heterocyclyl" are morpholino, piperazin-1-yl, piperidin-1-yl and imidazol-1-yl. In a further aspect of the invention a "heterocyclyl" is a heteroaryl. The term "heteroaryl" refers to an unsaturated and aromatic heterocyclyl. Examples and suitable values for heteroaryl groups include pyridinyl, pyrrolyl, pyrazolyl, isothiazolyl, indolyl, quinolinyl, thienyl, benzothiazolyl, thiadiazolyl, oxadiazolyl, imidazolyl, pyrimidinyl, pyrazinyl, pyridazinyl, isoxazolyl, thiazolyl, 1H-tetrazolyl, 1H-triazolyl, N-methylpyrrolyl, quinolin-4(1H)-one, pyridin-2(1H)-one, imidazo[1,2-a]pyridinyl, 1-isoquinolone, quinoxalinyl, pyridine-N-oxide and quinoline-N-oxide. In a particular embodiment, the heteroaryl is a 5- or 6-membered heteroaryl, for example, pyridinyl, pyrrolyl, pyrazolyl, isothiazolyl, thienyl, thiadiazolyl, oxadiazolyl, imidazolyl, pyrimidinyl, pyrazinyl, pyridazinyl, isoxazolyl, thiazolyl, 1H-tetrazolyl, 1H-triazolyl, N-methylpyrrolyl, and pyridine-N-oxide.

A "carbocyclyl" is a saturated, partially saturated or unsaturated, mono-, bi- or tricyclic carbon ring that contains 3-14 atoms; wherein a —CH$_2$— group can optionally be replaced by a —C(O)—. In one embodiment, "carbocyclyl" is a monocyclic ring containing 5 or 6 atoms or a bicyclic ring containing 9 or 10 atoms. Examples of carbocyclyls include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. The term carbocyclyl encompasses both cycloalkyl and aryl groups. The term cycloalkyl refers to a carbocyclyl which is completely saturated, for example cyclopropyl, cyclobutyl, cyclopentyl, and cyclohexyl. The term "aryl" refers to a carbocyclyl which is completely unsaturated and is aromatic. A $C_{6-14}$aryl is an aromatic, mono-, bi- or tricyclic carbon ring that contains 6-14 atoms, for example phenyl or naphthenyl.

As used herein, a "$C_{1-6}$alkoxy" refers to a group which has a $C_{1-6}$alkyl that is attached to another moiety via an oxygen atom. Examples of "$C_{1-6}$alkoxy" are methoxy, ethoxy and propoxy.

As used herein, a "N-($C_{1-6}$alkyl)amino" refers to a group which has a $C_{1-6}$alkyl that is attached to another moiety via —NH—. Examples of "N-($C_{1-6}$alkyl)amino" are methylamino and ethylamino As used herein, a "N,N-($C_{1-6}$alkyl)$_2$amino" refers to a group which has two independently selected $C_{1-6}$alkyl that are attached to another moiety via a nitrogen atom.

Examples of "N,N-($C_{1-6}$alkyl)$_2$amino" are N,N-dimethylamino, N,N-diethylamino and N-ethyl-N-methylamino As used herein, a "$C_{1-6}$alkanoyloxy" refers to a group which has the formula —OC(O)R, wherein R is a $C_{1-6}$alkyl. An example of "$C_{1-6}$alkanoyloxy" is acetoxy.

As used herein, a "$C_{1-6}$alkoxycarbonyl" refers to a group which has the formula —C(O)OR, wherein R is a $C_{1-6}$alkyl. Examples of "$C_{1-6}$alkoxycarbonyl" are methoxycarbonyl, ethoxycarbonyl, n- and t-butoxycarbonyl.

As used herein, a "$C_{1-6}$alkoxycarbonylamino" refers to a group which has the formula —NHC(O)OR, wherein R is a $C_{1-6}$alkyl. Examples of "$C_{1-6}$alkoxycarbonylamino" are methoxycarbonylamino, ethoxycarbonylamino, n- and t-butoxycarbonylamino As used herein, a "$C_{1-6}$alkanoylamino" refers to a group which has the formula —NHC(O)R, wherein R is a $C_{1-6}$alkyl. Examples of "$C_{1-6}$alkanoylamino" are formamido, acetamido and propionylamino As used herein, a "$C_{1-6}$alkanoyl" refers to a group which has the formula —C(O)R, wherein R is a $C_{1-6}$alkyl. Examples of "$C_{1-6}$alkanoyl" are propionyl and acetyl.

As used herein, a "N-($C_{1-6}$alkyl)sulphamoyl" refers to a group which has the formula —S(O)$_2$NHR, wherein R is a $C_{1-6}$alkyl. Examples of "N-($C_{1-6}$alkyl)sulphamoyl" are N-(methyl)sulphamoyl and N-(ethyl)sulphamoyl.

As used herein, a "N,N-($C_{1-6}$alkyl)$_2$sulphamoyl" refers to a group which has the formula —S(O)$_2$NR$_2$, wherein R, for each occurrence, is independently a $C_{1-6}$alkyl. Examples of "N,N-($C_{1-6}$alkyl)$_2$sulphamoyl" are N,N-(dimethyl)sulphamoyl and N-(methyl)-N-(ethyl)sulphamoyl.

As used herein, a "N-($C_{1-6}$alkyl)carbamoyl" refers to a group which has the formula —C(O)NHR, wherein R is a $C_{1-6}$alkyl. Examples of "N-($C_{1-6}$alkyl)carbamoyl" are methylaminocarbonyl and ethylaminocarbonyl.

As used herein, a "N,N-($C_{1-6}$alkyl)$_2$carbamoyl" refers to a group which has the formula —C(O)NR$_2$, wherein R, for each occurrence, is independently a $C_{1-6}$alkyl. Examples of "N,N-($C_{1-6}$alkyl)$_2$carbamoyl" are dimethylaminocarbonyl and methylethylaminocarbonyl.

As used herein, a "$C_{1-6}$alkylsulphonylamino" refers to a group which has the formula —S(O)$_2$NHR, wherein R is a $C_{1-6}$alkyl. Examples of "$C_{1-6}$alkylsulphonylamino" are methylsulphonylamino, isopropylsulphonylamino and t-butylsulphonylamino As used herein, a "$C_{1-6}$alkylsulphonyl" refers to a group which has the formula —S(O)$_2$R, wherein R is a $C_{1-6}$alkyl. Examples of "$C_{1-6}$alkylsulphonyl" are methylsulphonyl, isopropylsulphonyl and t-butylsulphonyl.

Examples of "$C_{1-6}$alkylS(O)$_a$ wherein a is 0, 1, or 2" are methylthio, ethylthio, methylsulphinyl, ethylsulphinyl, mesyl and ethylsulphonyl.

The term "formula (I) or (IA)", unless otherwise specified, refers to all embodiments of formula (I) or (IA) including but not limited to the specific examples disclosed herein.

A compound of formula (I) or (IA) may form stable acid or basic salts, and in such cases administration of a compound as a salt may be appropriate, and pharmaceutically acceptable salts may be made by conventional methods such as those described below.

Suitable pharmaceutically-acceptable salts include acid addition salts such as methanesulfonate, tosylate, α-glycerophosphate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

Within the present invention it is to be understood that a compound of the formula (I) or (IA), or a salt thereof may exhibit the phenomenon of tautomerism and that the formulae drawings within this specification can represent only one of the possible tautomeric forms. It is to be understood that the invention encompasses any tautomeric form which inhibits DNA gyrase and/or topoisomerase IV and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been possible to show graphically herein. The same applies to compound names.

It will be appreciated by those skilled in the art that certain compounds of formula (I) or (IA) contain an asymmetrically substituted carbon and/or sulfur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the inhibition of DNA gyrase and/or topoisomerase IV, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DNA gyrase and/or topoisomerase IV by the standard tests described hereinafter.

By way of clarity, compounds of the invention included all isotopes of the atoms present in formula (I) or (IA) and any of the examples or embodiments disclosed herein. For example, H (or hydrogen) represents any isotopic form of hydrogen including $^1H$, $^2H$ (D), and $^3H$ (T); C represents any isotopic form of carbon including $^{12}C$, $^{13}C$, and $^{14}C$; O represents any isotopic form of oxygen including $^{16}O$, $^{17}O$ and $^{18}O$; N represents any isotopic form of nitrogen including $^{13}N$, $^{14}N$ and $^{15}N$; P represents any isotopic form of phosphorous including $^{31}P$ and $^{32}P$; S represents any isotopic form of sulfur including $^{32}S$ and $^{35}S$; F represents any isotopic form of fluorine including $^{19}F$ and $^{18}F$; Cl represents any isotopic form of chlorine including $^{35}Cl$, $^{37}Cl$ and $^{36}Cl$; and the like. In a one embodiment, compounds represented by formula (I) or (IA) comprises isomers of the atoms therein in their naturally occurring abundance. However, in certain instances, it is desirable to enrich one or more atom in a particular isotope which would normally be present in less abundance. For example, $^1H$ would normally be present in greater than 99.98% abundance; however, a compound of the invention can be enriched in $^2H$ or $^3H$ at one or more positions where H is present. In particular embodiments of the compounds of formula (I) or (IA), when, for example, hydrogen is enriched in the deuterium isotope, the symbol "D" is used to represent the enrichment in deuterium. In one embodiment, when a compound of the invention is enriched in a radioactive isotope, for example $^3H$ and $^{14}C$, they may be useful in drug and/or substrate tissue distribution assays. It is to be understood that the invention encompasses all such isotopic forms which inhibit DNA gyrase and/or topoisomerase IV.

It is also to be understood that certain compounds of the formula (I) or (IA), and salts thereof can exist in solvated as well as unsolvated forms such as, for example, hydrated forms. It is to be understood that the invention encompasses all such solvated forms which inhibit DNA gyrase and/or topoisomerase IV.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention.

In one embodiment, the invention provides compounds of formula (IA), or a pharmaceutically acceptable salts thereof, wherein $X^1$ is N, and $X^2$ is $CR^{24}$. In certain embodiments, $R^{24}$ is selected from the group consisting of halo, heterocyclyl, $C_{1-6}$alkoxy, N-($C_{1-6}$alkyl)amino; wherein $R^{24}$ may be optionally substituted on one or more carbon by one or more one or more $R^{25}$; wherein if said heterocyclyl contains an —NH— moiety that nitrogen may be optionally substituted by $C_{1-6}$alkyl. In particular embodiments, $R^{25}$ is N,N-($C_{1-6}$alkyl)$_2$amino. In specific embodiments, $R^{24}$ is fluoro, methoxy, 2-(dimethylamino)ethoxy, 2-(dimethylamino)ethyl, or 4-methylpiperazin-1-yl.

In an alternate embodiment, the invention provides compounds of formula (IA), or a pharmaceutically acceptable salts thereof, wherein $X^2$ is N, and $X^1$ is CH.

In another embodiment, the invention provides compounds of formula (I) or (IA), or a pharmaceutically acceptable salts thereof, wherein X is CH.

In another embodiment, the invention provides compounds of formula (I) or (IA), or a pharmaceutically acceptable salts thereof, wherein X is N.

In another embodiment, the invention provides compounds of formula (I) or (IA), or a pharmaceutically acceptable salts thereof, wherein $R^1$ is a $C_{1-6}$alkyl.

In another embodiment, the invention provides compounds of formula (I) or (IA), or a pharmaceutically acceptable salts thereof, wherein $R^1$ is ethyl.

In another embodiment, the invention provides compounds of formula (I) or (IA), or a pharmaceutically acceptable salts thereof, wherein $R^2$ is hydrogen.

In another embodiment, the invention provides compounds of formula (I) or (IA), or a pharmaceutically acceptable salts thereof, wherein $R^3$ is ethyl, trifluouromethyl, or phenyl.

In another embodiment, the invention provides compounds of formula (I) or (IA), or a pharmaceutically acceptable salts thereof, wherein $R^5$ is —OH or $C_{1-6}$alkoxy which is optionally substituted on one or more carbon atoms with one or more $R^{14}$.

In another embodiment, the invention provides compounds of formula (I) or (IA), or a pharmaceutically acceptable salts thereof, wherein $R^5$ is selected from the group consisting of —OH, ethoxy, 2-hydroxyethoxy, 3-hydroxypropoxy, 2-(phosphonooxy)ethoxy, 3-(phosphonooxy)propoxy, or 2-{[bis(benzyloxy)phosphoryl]oxy}ethoxy.

In another embodiment, the invention provides compounds of formula (I) or (IA), or a pharmaceutically acceptable salts thereof, wherein $R^6$ is a $C_{1-6}$alkyl which is substituted on one or more carbon atoms with one or more independently selected $R^{16}$.

In another embodiment, the invention provides compounds of formula (I) or (IA), or a pharmaceutically acceptable salts thereof, wherein $R^6$, or a pharmaceutically acceptable salts thereof, wherein $R^6$ is 2-hydroxyethyl, ethyl, 1,3-dimethoxypropan-2-yl, 3,3-dimethylbutyl, 2-methoxyethyl, 1-hydroxy-4-methyl-pentan-2-yl, 2-(N,N-dimethylamino)-ethyl, 1-hydroxy-3,3-dimethyl-butan-2-yl, 2-(phosphonooxy) ethoxy, 1-(phosphonooxy)-4-methyl-pentan-2-yl, 2-{[bis (benzyloxy)phosphoryl]oxy}ethyl, or 1-{[(benzyloxy)(hydroxy)phosphoryl]oxy}-4-methyl-penan-2-yl.

In another embodiment, the invention provides compounds of formula (I) or (IA), or a pharmaceutically acceptable salts thereof, wherein $R^6$ is 2-hydroxyethyl, ethyl, 1-hydroxy-4-methyl-pentan-2-yl, 2-(N,N-dimethylamino)-ethyl, 1-hydroxy-3,3-dimethyl-butan-2-yl, 2-(phosphonooxy)ethoxy, 1-(phosphonooxy)-4-methyl-pentan-2-yl, 2-{[bis(benzyloxy)phosphoryl]oxy}ethyl, or 1-{[(benzyloxy)(hydroxy) phosphoryl]oxy}-4-methyl-penan-2-yl.

In another embodiment, the invention provides compounds of formula (I) or (IA), or a pharmaceutically acceptable salts thereof, wherein $R^6$ is $C_{3-6}$cycloalkyl.

In another embodiment, the invention provides compounds of formula (I) or (IA), or a pharmaceutically acceptable salts thereof, wherein $R^6$ is a heterocyclyl-L-; wherein said heterocyclyl is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$.

In another embodiment, the invention provides compounds of formula (I) or (IA), or a pharmaceutically acceptable salts thereof, wherein $R^6$ is 2-(1-methyl-piperidin-4-yl)-ethyl, 1-ethylpyrrolidin-2-yl)methyl, (1-methyl-1H-imidazol-4-yl) methyl, 2-morpholinopropyl, (2-(diethylamino)ethyl)piperidin-3-yl, cyclohexyl, 1-(2-morpholino-ethyl)-piperidin-3-yl, 1-methyl-piperidin-4-ylmethyl, or 1-(tert-butoxycarbonyl)-piperidin-3-yl, piperidin-3-yl.

In another embodiment, the invention provides compounds of formula (I) or (IA), or a pharmaceutically acceptable salts thereof, wherein $R^6$ is 2-(1-methyl-piperidin-4-yl)-ethyl, 1-(2-morpholino-ethyl)-piperidin-3-yl, 1-methyl-piperidin-4-ylmethyl, or 1-(tert-butoxycarbonyl)-piperidin-3-yl, piperidin-3-yl.

In another embodiment, the invention provides compounds of formula (IA), or a pharmaceutically acceptable salts thereof represented by the following formula:

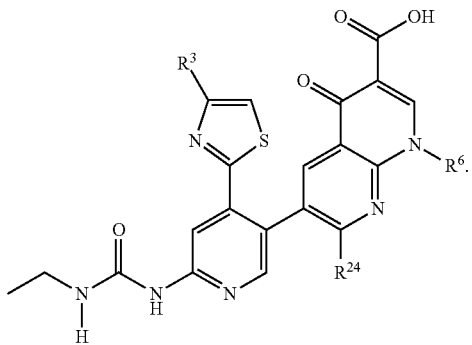

In another embodiment, the invention provides compounds of formula (IA), or a pharmaceutically acceptable salts thereof represented by the following formula:

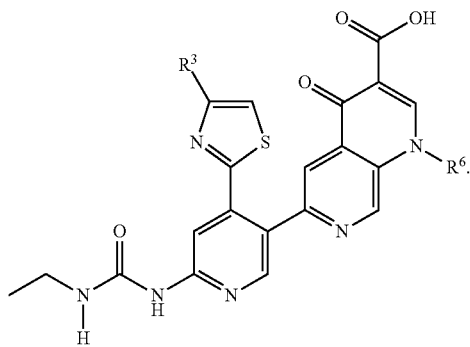

In another embodiment, the invention provides compounds of formula (IA), or a pharmaceutically acceptable salts thereof represented by the following formula:

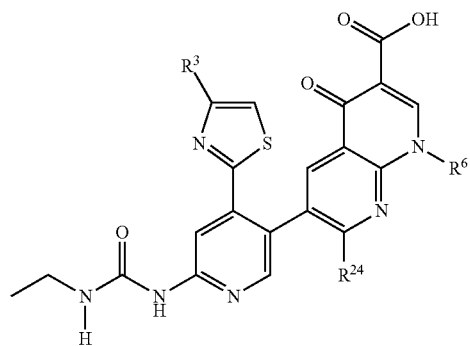

or a pharmaceutically acceptable salt thereof, wherein:
$R^3$ is $CF_3$, a cyclopropyl, or a phenyl that may be optionally substituted with halogen (e.g., F) or —OCH$_3$;
$R^6$ is $C_{1-6}$alkyl, or a 4-6 membered heterocyclyl-L-; wherein the $C_{1-6}$alkyl is optionally substituted on one or more carbon atoms with hydroxy or $C_{1-6}$alkoxy; and wherein if said heterocyclyl contains an —NH— moiety that nitrogen may be optionally substituted by a group selected from $C_{1-3}$alkyl, wherein the $C_{1-3}$alkyl may be optionally substituted with dimethylamino, diethylamino, morpholinyl, or piperazinyl, piperidinyl;
$R^{24}$ is selected from the group consisting of hydrogen, 5-6 membered heterocyclyl, or —NH—(CH$_2$)$_{1-2}$—R$_{25}$; wherein the heterocyclyl is optionally substituted on one or more carbon atoms with amino or —(CH$_2$)$_{1-2}$—NH$_2$; and wherein if said heterocyclyl contains an —NH— moiety that nitrogen may be optionally substituted by a group selected from $C_{1-3}$alkyl, wherein the $C_{1-3}$alkyl may be optionally substituted with dimethylamino, diethylamino, morpholinyl, or piperazinyl, piperidinyl;
$R^{25}$ is selected from N-($C_{1-6}$alkyl)amino or N,N-($C_{1-6}$alkyl)$_2$amino (e.g., dimethylamine or diethylamine);
L is a direct bond or a $C_{1-2}$alkyl. In a certain embodiments, $R^3$ is $CF_3$, a cyclopropyl, or a phenyl. In a particular embodiment, $R^3$ is $CF_3$. In a certain embodiments, $R^{24}$ is N-methylpiperazinyl. In a certain embodiments, $R^{24}$ is 2-(dimethylamino)ethylamino. In a certain embodiments, $R^{24}$ is hydrogen. In a certain embodiments, $R^6$ is ethyl. In a certain embodiments, $R^6$ is (1-ethylpyrrolidin-2-yl)methyl. In a certain embodiments, $R^6$ is 1-(2-morpholinoethyl)piperidin-3-yl.

In another embodiment, the invention provides compounds of formula (IA), or a pharmaceutically acceptable salts thereof represented by the following formula:

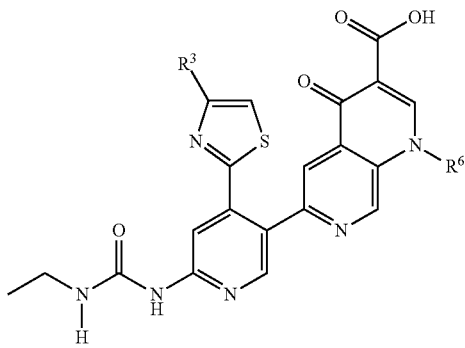

or a pharmaceutically acceptable salt thereof, wherein:
$R^3$ is $CF_3$, a cyclopropyl, or a phenyl that may be optionally substituted with halogen (e.g., F) or —$OCH_3$;
$R^6$ is $C_{1-6}$alkyl, or a 4-6 membered heterocyclyl-L-; wherein the $C_{1-6}$alkyl is optionally substituted on one or more carbon atoms with hydroxy or $C_{1-6}$alkoxy; and wherein if said heterocyclyl contains an —NH— moiety that nitrogen may be optionally substituted by a group selected from $C_{1-3}$alkyl, wherein the $C_{1-3}$alkyl may be optionally substituted with dimethylamino, diethylamino, morpholinyl, or piperazinyl, piperidinyl; and
L is a direct bond or a $C_{1-2}$alkylene. In a certain embodiments, $R^3$ is $CF_3$, a cyclopropyl, or a phenyl. In a particular embodiment, $R^3$ is $CF_3$. In a certain embodiments, $R^6$ is ethyl. In a certain embodiments, $R^6$ is (1-ethylpyrrolidin-2-yl)methyl. In a certain embodiments, $R^6$ is 1-(2-morpholinoethyl)piperidin-3-yl.

In a particular embodiment, the present invention provides compounds having a structural formula (I) or (IA), or a pharmaceutically acceptable salts thereof, as recited above wherein:
X is CH;
$R^1$ is $C_{1-4}$alkyl;
$R^2$ is hydrogen;
$R^3$ is trifluoromethyl;
$R^5$ is —OH or a $C_{1-6}$alkoxy which is optionally substituted on one or more carbon atoms with one or more $R^{14}$;
$R^6$ is a $C_{1-6}$alkyl which is optionally substituted on one or more carbon atom with one or more $R^{16}$;
$R^{14}$, for each occurrence, is independently selected from hydroxy, phosphonooxy, or [bis(benzyloxy)phosphoryl]oxy; and
$R^{16}$, for each occurrence, is independently selected from hydroxy, phosphonooxy, [(benzyloxy)(hydroxy)phosphoryl]oxy, [bis(benzyloxy)phosphoryl]oxy, N,N-($C_{1-6}$alkyl)$_2$amino, 1-methylpiperidinyl.

In a particular embodiment, the present invention provides compounds having a structural formula (I) or (IA), or a pharmaceutically acceptable salts thereof, as recited above wherein:
X is CH;
$R^1$ is $C_{1-4}$alkyl;
$R^2$ is hydrogen;
$R^3$ is trifluoromethyl;
$R^5$ is —OH or a $C_{1-6}$alkoxy which is optionally substituted on one or more carbon atoms with one or more $R^{14}$;
$R^6$ is a heterocyclyl which is optionally substituted on one or more carbon atom with one or more $R^{16}$;
$R^{14}$, for each occurrence, is independently selected from hydroxy, phosphonooxy, or [bis(benzyloxy)phosphoryl]oxy; and
$R^{16}$, for each occurrence, is independently selected from 2-morpholino-ethyl, or t-butoxycarbonyl.

Particular compounds of the invention are the compounds of the Examples, and pharmaceutically acceptable salts thereof, each of which provides a further independent aspect of the invention.

In another embodiment, the invention provides pharmaceutical compositions comprising a pharmaceutically acceptable excipient or carrier and a compound represented by formula (I) or (IA), or a pharmaceutically acceptable salt thereof.

In a further aspect the present invention provides a process for preparing a compound of formula (I) or (IA), or a pharmaceutically-acceptable salt thereof, wherein variable groups in the schemes below are as defined in formula (I) or (IA) unless otherwise specified. In general, the compounds of the invention can be prepared by a palladium catalyzed Suzuki coupling reaction of a boronic ester or acid derivative (i) and a halo derivative (ii), as shown in Schemes I. Typically, the coupling reaction is heated and is carried out in the presence of a base such as $Cs_2CO_3$.

Scheme I

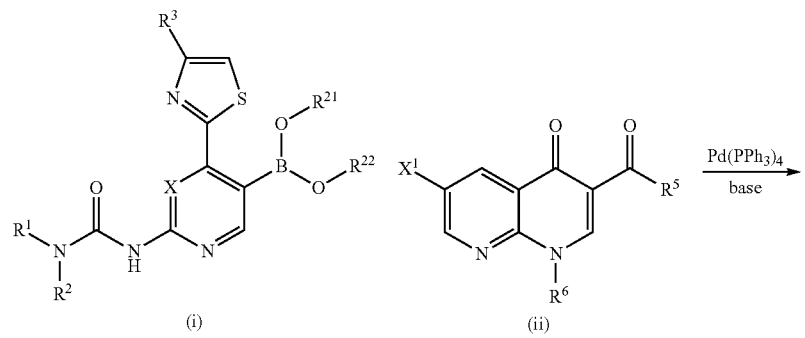

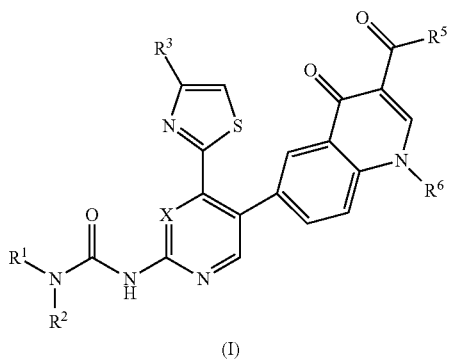

(I)

$X^2$ is a halo.
$R^{21}$ and $R^{22}$ are each independently hydrogen, an alkyl group or $R^{21}$ and $R^{22}$, together with —O—B—O—, can form a cyclic boronic ester such as 4,4,5,5,-tetramethyl-1,3,2-dioxaborolan-2-yl.

Boronic acids and ester derivatives can be prepared by treating an aryl halide derivative with a grignard reagent followed by a strong base such as n-butyl lithium, then adding a boron derivative such as 4,4,4',4',5,5,5',5'-octamethyl-2,2'-bi(1,3,2-dioxaborolane) or boron methoxide.

$R^5$ in Intermediate (ii) is typically an alkoxy group which is generally stable during the Suzuki coupling reaction. $R^5$ can be converted to an —OH group after the coupling reaction by treating the product with a strong base in a protic solvent such as water, an alcohol or a mixture of an alcohol and an organic solvent (e.g. THF/MeOH). $R^5$ can be converted to an amino, an N-alkylamino or an N,N-dialkylamino by treating the ester derivative an amino, an N-alkylamino or an N,N-dialkylamino in an alcohol.

The urea portion of the compounds of the invention can be prepared from an isocyanate derivative either before or after the Suzuki coupling reaction from an amine derivative. If the Suzuki coupling reaction is preformed before formation of the urea, the amine is protected with an amine protecting group. When forming the urea derivative, the isocyanate derivative (iv) is typically combined with the amine derivative (iii) in an organic solvent and heated, as shown in Scheme II. The solvent can be aqueous, organic or a mixture of an aqueous miscible organic solvent and water.

Scheme II

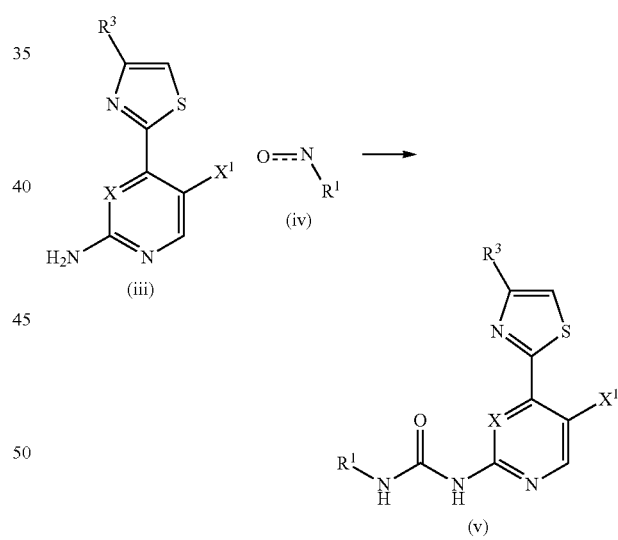

A Suzuki coupling reaction can be used to attach the thiazole ring to ring A as shown in Scheme III. Although Scheme III shows the coupling reaction of the thiazole ring occurring before the coupling reaction to link ring A to the 1,4-dihydro-1,8-naphthyridine ring, the reactions could be preformed in the alternative order. When the thiazole group is attached before the coupling reaction to attach 1,4-dihydroquinoline ring, ring A can be brominated by heating it with 1-bromopyrrolidine-2,5-dione to form a substrate for the Suzuki coupling reaction.

Scheme III

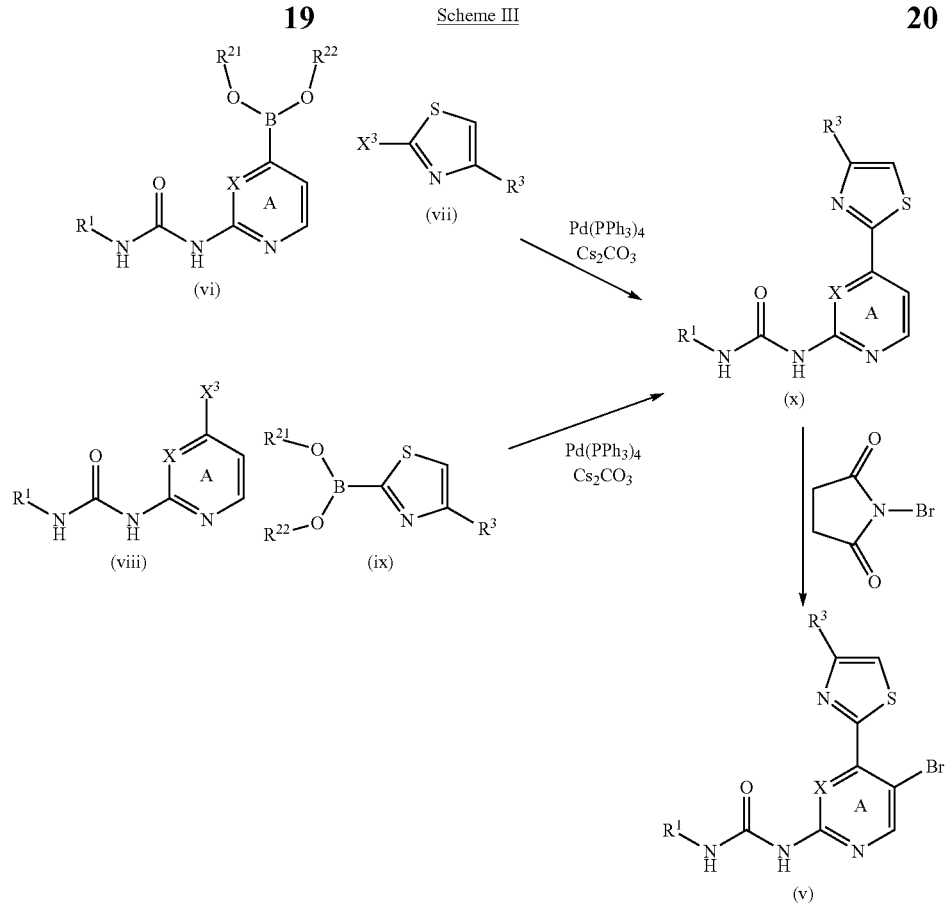

$X^3$ is a halo.

Alternatively, the thiazolyl ring can be prepared from an ester derivative either before or after coupling of the 1,4-dihydro-1,8-naphthyridine ring to ring A. For example, an ester derivative (xii) can be converted to an amide (xiii) by treating it with a solution of ammonia in an alcohol. The amide derivative (xiii) can then be converted to a thioamide (xiv) by treating the amide with Lawessons reagent. The thioamide (xiv) is then heated with an α-halo-ketone followed by treatment with an alkylsulfonyl chloride and a base to form the thiazole (v) (see Scheme V). Although the thiazole ring is prepared before the Suzuki coupling reaction to attach 1,4-dihydroquinoline ring in Scheme V, it could also be prepared after the coupling reaction of the ester derivative to the 1,4-dihydroquinoline ring.

-continued

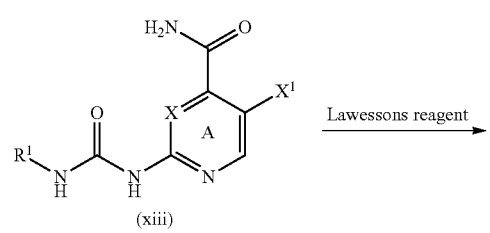

Scheme V

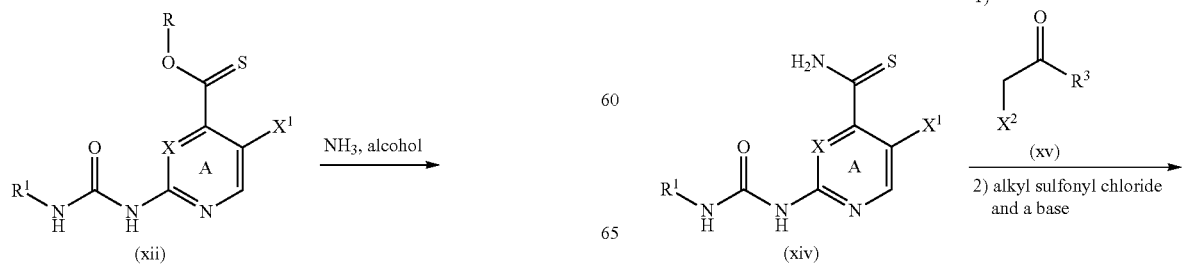

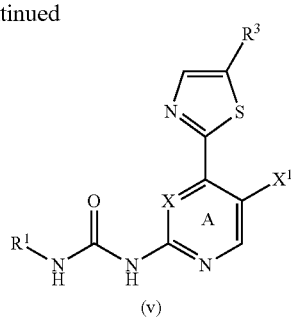

(v)

X² is a halo.
R is an alkyl.

The 1,4-dihydro-1,8-naphthyridine derivative (xvi) can be prepared from an alkyl 2-(5-bromo-2-fluoronicotinoyl)-3-(dimethylamino)acrylate by heating it with a primary amine (xvii) in the presence of a base as shown in Scheme VI.

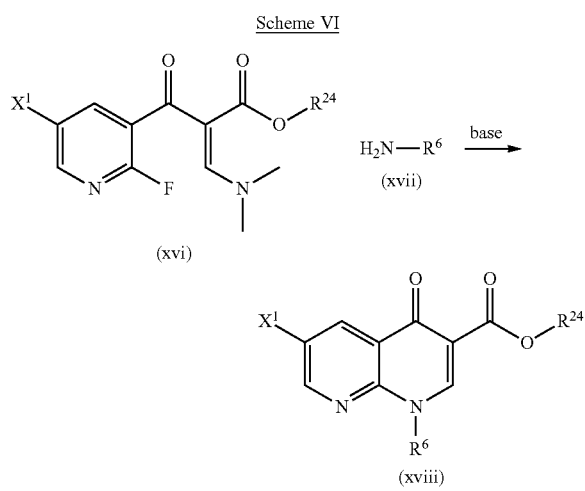

R²⁴ is an alkyl.

A hydroxy group of the compounds of the invention can be converted to phosphonooxy group by treating the hydroxy group triphenylphosphine and an oxidant such as diisopropyl azodicarboxylate followed by a protected hydrogen phosphate such as dibenzyl hydrogen phosphate to form a [bis(benzyloxy)phosphoryl]oxy group. The [bis(benzyloxy)phosphoryl]oxy can be deprotected to form a phosphonooxy group by, for example, treating it with a trimethylsilyl halide.

The formation of a pharmaceutically-acceptable salt is within the skill of an ordinary organic chemist using standard techniques.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. The reagents used to introduce such ring substituents are either commercially available or are made by processes known in the art.

Introduction of substituents into a ring may convert one compound of the formula (I) or (IA) into another compound of the formula (I) or (IA). Such reactions and modifications include, for example, introduction of a substituent by means of an aromatic substitution reaction, reduction of substituents, alkylation of substituents, oxidation of substituents, esterification of substituents, amidation of substituents, formation of heteroaryl rings. The reagents and reaction conditions for such procedures are well known in the chemical art. Particular examples of aromatic substitution reactions include the introduction of alkoxides, diazotization reactions followed by introduction of thiol group, alcohol group, halogen group. Examples of modifications include; oxidation of alkylthio to alkylsulphinyl or alkylsulphonyl.

The skilled organic chemist will be able to use and adapt the information contained and referenced within the above references, and accompanying Examples therein and also the Examples herein, to obtain necessary starting materials, and products. If not commercially available, the necessary starting materials for the procedures such as those described above may be made by procedures which are selected from standard organic chemical techniques, techniques which are analogous to the synthesis of known, structurally similar compounds, or techniques which are analogous to the above described procedure or the procedures described in the examples. It is noted that many of the starting materials for synthetic methods as described above are commercially available and/or widely reported in the scientific literature, or could be made from commercially available compounds using adaptations of processes reported in the scientific literature. The reader is further referred to Advanced Organic Chemistry, 4$^{th}$ Edition, by Jerry March, published by John Wiley & Sons 1992, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon, or for example, an allyl group which may be removed, for example, by use of a palladium catalyst such as palladium acetate.

The protecting groups may be removed at any convenient stage in the synthesis using conventional techniques well known in the chemical art, or they may be removed during a later reaction step or work-up.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

Enzyme Potency Testing Methods

*E. coli* GyrB ATPase Inhibition Activity: Compounds can be tested for inhibition of *E. coli* GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays can be performed in multiwell plates in 30 µl reactions containing: 50 mM Hepes buffer pH 7.5, 75 mM ammonium acetate, 8.0 mM magnesium chloride, 0.5 mM ethylenediaminetetraacetic acid, 5% glycerol, 1 mM 1,4-Dithio-DL-threitol, 200 nM bovine serum albumin, 1.6 µg/ml sheared salmon sperm DNA, 400 pM *E. coli* GyrA, 400 pM *E. coli* GyrB, 250 µM ATP, and compound in dimethylsulfoxide. Reactions can be quenched with 30 µl of ammonium molybdate/malachite green detection reagent containing 1.2 mM malachite green hydrochloride, 8.5 mM ammonium molybdate tetrahydrate, and 1 M hydrochloric acid. Plates can be read in an absorbance plate reader at 650 nm and percent inhibition values are calculated using dimethylsulfoxide (2%)-containing reactions as 0% inhibition and EDTA-containing (2.4 µM) reactions as 100% inhibition controls. An $IC_{50}$ measurement of compound potency for each compound can be determined from reactions performed in the presence of 10 different compound concentrations.

*E. coli* Topoisomerase IV ATPase Inhibition Activity: Compounds can be tested for inhibition of *E. coli* topoisomerase IV ATPase activity as described above for *E. coli* GyrB except the 30 µl reactions contained the following: 20 mM TRIS buffer pH 8, 50 mM ammonium acetate, 8 mM magnesium chloride, 5% glycerol, 5 mM 1,4-Dithio-DL-threitol, 0.005% Brij-35, 5 µg/ml sheared salmon sperm DNA, 500 pM *E. coli* ParC, 500 pM *E. coli* ParE, 160 µM ATP, and compound in dimethylsulfoxide. An $IC_{50}$ measurement of compound potency for each compound can be determined from reactions performed in the presence of 10 different compound concentrations.

Many of the compounds of the invention were tested in an assay substantially similar to the assays described above for measuring the inhibition of *E. coli* GyrB ATPase and *E. coli* Topoisomerase IV ATPase and had an $IC_{50}$ values of <200 µM in one or both assays.

*S. aureus* GyrB ATPase Inhibition Activity: Compounds may be tested for inhibition of *S. aureus* GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays can be performed in multiwell plates in 30 µl reactions containing: 50 mM Hepes buffer pH 7.5, 75 mM ammonium acetate, 8.0 mM magnesium chloride, 0.5 mM ethylenediaminetetraacetic acid, 5% glycerol, 1.0 mM 1,4-Dithio-DL-threitol, 200 nM bovine serum albumin, 1.0 µg/ml sheared salmon sperm DNA, 250 pM *E. coli* GyrA, 250 pM *S. aureus* GyrB, 250 µM ATP, and compound in dimethylsulfoxide. Reactions can be quenched with 30 µl of ammonium molybdate/malachite green detection reagent containing 1.2 mM malachite green hydrochloride, 8.5 mM ammonium molybdate tetrahydrate, and 1 M hydrochloric acid. Plates can be read in an absorbance plate reader at 650 nm and percent inhibition values can be calculated using dimethylsulfoxide (2%)-containing reactions as 0% inhibition and EDTA-containing (2.4 µM) reactions as 100% inhibition controls. An $IC_{50}$ measurement of compound potency for each compound can be determined from reactions performed in the presence of 10 different compound concentrations.

The compounds in the table below were tested in an assay substantially similar to the assay described above for measuring the inhibition of *S. aureus* GyrB ATPase and were found to have a percent inhibition of *S. aureus* GyrB ATPase as shown in the table.

| Example | Percent Inhibition (1 µM) |
| --- | --- |
| 1 | 107 |
| 2 | 123 |
| 3 | No data |
| 4 | No data |
| 5 | No data |
| 6 | No data |
| 7 | No data |
| 8 | 98 |
| 9 | 96 |
| 10 | 93 |
| 11 | 104 |
| 12 | 104 |
| 13 | No data |
| 14 | 103 |
| 15 | No data |
| 16 | 104 |
| 17 | 106 |
| 18 | 108 |
| 19 | No data |
| 20 | 104 |
| 21 | No data |
| 22 | 104 |
| 23 | No data |
| 24 | No data |

-continued

| Example | Percent Inhibition (1 µM) |
|---|---|
| 25 | 108 |
| 26 | No data |
| 27 | No data |
| 28 | No data |
| 29 | 105 |
| 30 | No data |
| 31 | 104 |
| 32 | 103 |
| 33 | 102 |
| 34 | 103 |
| 35 | 102 |
| 36 | 100 |
| 37 | 109 |
| 38 | 101 |
| 39 | 102 |
| 40 | 103 |
| 41 | 102 |
| 42 | 103 |
| 43 | 94 |
| 44 | 102 |
| 45 | 107 |
| 46 | 106 |
| 47 | 98 |
| 48 | 101 |
| 49 | 98 |
| 50 | 99 |
| 51 | 102 |
| 52 | 105 |
| 53 | 103 |
| 54 | 106 |
| 55 | 103 |
| 56 | 101 |
| 57 | 107 |
| 58 | 104 |
| 59 | 108 |
| 60 | 101 |
| 61 | 103 |
| 62 | No data |
| 63 | 105 |
| 64 | 100 |
| 65 | 98 |
| 66 | 106 |
| 67 | 93 |
| 68 | 110 |
| 69 | 103 |
| 70 | 102 |
| 71 | 103 |
| 72 | 105 |
| 73 | 108 |
| 74 | 100 |
| 75 | 108 |
| 76 | 109 |
| 77 | 105 |
| 78 | 98 |

Bacterial Susceptibility Testing Methods

Compounds may be tested for antimicrobial activity by susceptibility testing in liquid media. Compounds may be dissolved in dimethylsulfoxide and tested in 10 doubling dilutions in the susceptibility assays. The organisms used in the assay may be grown overnight on suitable agar media and then suspended in a liquid medium appropriate for the growth of the organism. The suspension can be a 0.5 McFarland and a further 1 in 10 dilution can be made into the same liquid medium to prepare the final organism suspension in 100 µL. Plates can be incubated under appropriate conditions at 37° C. for 24 hrs prior to reading. The Minimum Inhibitory Concentration (MIC) may be determined as the lowest drug concentration able to reduce growth by 80% or more.

In an assay comparable to the above, Example 10 had an MIC of 0.55 µM against *S. aureus*.

According to a further feature of the invention there is provided a compound of the formula (I) or (IA), or a pharmaceutically-acceptable salt thereof, for use in a method of treatment of the human or animal body by therapy.

In one embodiment, the invention provides a method of treating a bacterial infection in an animal, such as a human, comprising administering to the animal or human an effective amount of a compound of any one of formulas (I) or (IA), or a pharmaceutically acceptable salt thereof.

We have found that compounds of the present invention inhibit bacterial DNA gyrase and/or topoisomerase IV and are therefore of interest for their antibacterial effects. In one aspect of the invention the compounds of the invention inhibit bacterial DNA gyrase and are therefore of interest for their antibacterial effects. In one aspect of the invention, the compounds of the invention inhibit topoisomerase IV and are therefore of interest for their antibacterial effects. In one aspect of the invention, the compounds of the invention inhibit both DNA gyrase and topoisomerase IV and are therefore of interest for their antibacterial effects. Thus, the compounds of the invention are useful in treating or preventing bacterial infections.

In one aspect of the invention an "infection" or "bacterial infection" refers to an infection caused by *Acinetobacter baumanii*. In one aspect of the invention an "infection" or "bacterial infection" refers to an infection caused by *Acinetobacter haemolyticus*. In one aspect of the invention an "infection" or "bacterial infection" refers to an infection caused by *Acinetobacter junii*. In one aspect of the invention an "infection" or "bacterial infection" refers to an infection caused by *Acinetobacter johnsonii*. In one aspect of the invention an "infection" or "bacterial infection" refers to an infection caused by *Acinetobacter lwoffi*. In one aspect of the invention an "infection" or "bacterial infection" refers to an infection caused by *Bacteroides bivius*. In one aspect of the invention an "infection" or "bacterial infection" refers to an infection caused by *Bacteroides fragilis*. In one aspect of the invention an "infection" or "bacterial infection" refers to an infection caused by *Burkholderia cepacia*. In one aspect of the invention an "infection" or "bacterial infection" refers to an infection caused by *Campylobacter jejuni*. In one aspect of the invention an "infection" or "bacterial infection" refers to an infection caused by *Chlamydia pneumoniae*. In one aspect of the invention an "infection" or "bacterial infection" refers to an infection caused by *Chlamydia urealyticus*. In one aspect of the invention an "infection" or "bacterial infection" refers to an infection caused by *Chlamydophila pneumoniae*. In one aspect of the invention an "infection" or "bacterial infection" refers to an infection caused by *Clostridium difficile*. In one aspect of the invention an "infection" or "bacterial infection" refers to an infection caused by *Enterobacter aerogenes*. In one aspect of the invention an "infection" or "bacterial infection" refers to an infection caused by *Enterobacter cloacae*. In one aspect of the invention an "infection" or "bacterial infection" refers to an infection caused by *Enterococcus faecalis*. In one aspect of the invention an "infection" or "bacterial infection" refers to an infection caused by *Enterococcus faecium*. In one aspect of the invention an "infection" or "bacterial infection" refers to an infection caused by *Escherichia coli*. In one aspect of the invention an "infection" or "bacterial infection" refers to an infection caused by *Gardnerella vaginalis*. In one aspect of the invention an "infection" or "bacterial infection" refers to an infection caused by *Haemophilus parainfluenzae*. In one aspect of the invention an "infection" or "bacterial infection" refers to an infection caused by *Haemophilus influenzae*. In one aspect of the invention an "infection" or "bacterial infection" refers to an infection caused by *Helicobacter pylori*. In one aspect of the invention an "infection" or "bacterial infection" refers to an infection caused by *Klebsiella pneumoniae*. In one aspect of the invention an "infection" or "bacterial infection" refers to an infection caused by *Legionella pneumophila*. In one aspect of the invention an "infection" or "bacterial infection" refers to an infection caused by Methicillin-resistant *Staphylococcus aureus*. In one aspect of the invention an "infection" or "bacterial infection" refers to an infection caused by Methicillin-susceptible *Staphylococcus aureus*. In one aspect of the invention an "infection" or "bacterial infection" refers to an infection caused by *Moraxella catarrhalis*. In one aspect of the invention an "infection" or "bacterial infection" refers to an infection caused by *Morganella morganii*. In one aspect of the invention an "infection" or "bacterial infection" refers to an infection caused by *Mycoplasma pneumoniae*. In one aspect of the invention an "infection" or "bacterial infection" refers to an infection caused by *Neisseria gonorrhoeae*. In one aspect of the invention an "infection" or "bacterial infection" refers to an infection caused by Penicillin-resistant *Streptococcus pneumoniae*. In one aspect of the invention an "infection" or "bacterial infection" refers to an infection caused by Penicillin-susceptible *Streptococcus pneumoniae*. In one aspect of the invention an "infection" or "bacterial infection" refers to an infection caused by *Peptostreptococcus magnus*. In one aspect of the invention an "infection" or "bacterial infection" refers to an infection caused by *Peptostreptococcus micros*. In one aspect of the invention an "infection" or "bacterial infection" refers to an infection caused by *Peptostreptococcus anaerobius*. In one aspect of the invention an "infection" or "bacterial infection" refers to an infection caused by *Peptostreptococcus asaccharolyticus*. In one aspect of the invention an "infection" or "bacterial infection" refers to an infection caused by *Peptostreptococcus prevotii*. In one aspect of the invention an "infection" or "bacterial infection" refers to an infection caused by *Peptostreptococcus tetradius*. In one aspect of the invention an "infection" or "bacterial infection" refers to an infection caused by *Peptostreptococcus vaginalis*. In one aspect of the invention an "infection" or "bacterial infection" refers to an infection caused by *Proteus mirabilis*. In one aspect of the invention an "infection" or "bacterial infection" refers to an infection caused by *Pseudomonas aeruginosa*. In one aspect of the invention an "infection" or "bacterial infection" refers to an infection caused by Quinolone-Resistant *Staphylococcus aureus*. In one aspect of the invention an "infection" or "bacterial infection" refers to an infection caused by Quinolone-Resistant *Staphylococcus epidermis*. In one aspect of the invention an "infection" or "bacterial infection" refers to an infection caused by *Salmonella typhi*. In one aspect of the invention an "infection" or "bacterial infection" refers to an infection caused by *Salmonella paratyphi*. In one aspect of the invention an "infection" or "bacterial infection" refers to an infection caused by *Salmonella enteritidis*. In one aspect of the invention an "infection" or "bacterial infection" refers to an infection caused by *Salmonella typhimurium*. In one aspect of the invention an "infection" or "bacterial infection" refers to an infection caused by *Serratia marcescens*. In one aspect of the invention an "infection" or "bacterial infection" refers to an infection caused by *Staphylococcus aureus*. In one aspect of the invention an "infection" or "bacterial infection" refers to an infection caused by *Staphylococcus epidermidis*. In one aspect of the invention an "infection" or "bacterial infection" refers to an infection caused by *Staphylococcus saprophyticus*. In one aspect of the invention an "infection" or "bacterial infection" refers to an infection caused by *Streptoccocus agalactiae*. In one aspect of the invention an "infection" or "bacterial infection" refers to an infection caused by *Streptococcus pneumoniae*. In one aspect of the invention an "infection" or "bacterial infection" refers to an infection caused by *Streptococcus pyogenes*. In one aspect of the invention an "infection" or "bacterial infection" refers to an infection caused by *Stenotrophomonas maltophilia*. In one aspect of the invention an "infection" or "bacterial infection" refers to an infection caused by *Ureaplasma urealyticum*. In one aspect of the invention an "infection" or "bacterial infection" refers to an infection caused by Vancomycin-Resistant *Enterococcus faecium*. In one aspect of the invention an "infection" or "bacterial infection" refers to an infection caused by Vancomycin-Resistant *Enterococcus faecalis*. In one aspect of the invention an "infection" or "bacterial infection" refers to an infection caused by Vancomycin-Resistant *Staphylococcus aureus*. In one aspect of the invention an "infection" or "bacterial infection" refers to an infection caused by Vancomycin-Resistant *Staphylococcus epidermis*. In one aspect of the invention an "infection" or "bacterial infection" refers to an infection caused by *Mycobacterium tuberculosis*. In one aspect of the invention an "infection" or "bacterial infection" refers to an infection caused by *Clostridium perfringens*. In one aspect of the invention an "infection" or "bacterial infection" refers to an infection caused by *Klebsiella oxytoca*. In one aspect of the invention an "infection" or "bacterial infection" refers to an infection caused by *Neisseria miningitidis*. In one aspect of the invention an "infection" or "bacterial infection" refers to an infection caused by *Fusobacterium* spp. In one aspect of the invention an "infection" or "bacterial infection" refers to an infection caused by *Peptococcus* spp. In one aspect of the invention an "infection" or "bacterial infection" refers to an infection caused by *Proteus vulgaris*. In one aspect of the invention an "infection" or "bacterial infection" refers to an infection caused by Coagulase-negative *Staphylococcus* (including *Staphylococcus lugdunensis*, *Staphylococcus capitis*, *Staphylococcus hominis*, and *Staphylococcus saprophyticus*).

In one aspect of the invention an "infection" or "bacterial infection" refers to an infection caused by *Acinetobacter* spp. In one aspect of the invention an "infection" or "bacterial infection" refers to an infection caused by *Bacteroides* spp. In one aspect of the invention an "infection" or "bacterial infection" refers to an infection caused by *Burkholderia* spp. In one aspect of the invention an "infection" or "bacterial infection" refers to an infection caused by *Campylobacter* spp. In one aspect of the invention an "infection" or "bacterial infection" refers to an infection caused by *Chlamydia* spp. In one aspect of the invention an "infection" or "bacterial infection" refers to an infection caused by *Chlamydophila* spp. In one aspect of the invention an "infection" or "bacterial infection" refers to an infection caused by *Clostridium* spp. In one aspect of the invention an "infection" or "bacterial infection" refers to an infection caused by *Enterobacter* spp. In one aspect of the invention an "infection" or "bacterial infection" refers to an infection caused by *Enterococcus* spp. In one aspect of the invention an "infection" or "bacterial infection" refers to an infection caused by *Escherichia* spp. In one aspect of the invention an "infection" or "bacterial infection" refers to an infection caused by *Gardnerella* spp. In one aspect of the invention an "infection" or "bacterial infection" refers to an infection caused by *Haemophilus* spp. In one aspect of the invention an "infection" or "bacterial infection" refers to an infection caused by *Helicobacter* spp. In one aspect of the invention an "infection" or "bacterial infection" refers to an infection caused by *Klebsiella* spp. In one aspect of the invention an "infection" or "bacterial infection" refers to an infection caused by *Legionella* spp. In one aspect of the invention an "infection" or "bacterial infection" refers to an infection caused by *Moraxella* spp. In one aspect of the invention an "infection" or "bacterial infection" refers to an infection caused by *Morganella* spp. In one aspect of the invention an "infection" or "bacterial infection" refers to an infection caused by *Mycoplasma* spp. In one aspect of the invention an "infection" or "bacterial infection" refers to an infection caused by *Neisseria* spp. In one aspect of the invention an "infection" or "bacterial infection" refers to an infection caused by *Peptostreptococcus* spp. In one aspect of the invention an "infection" or "bacterial infection" refers to an infection caused by *Proteus* spp. In one aspect of the invention an "infection" or "bacterial infection" refers to an infection caused by *Pseudomonas* spp. In one aspect of the invention an "infection" or "bacterial infection" refers to an infection caused by *Salmonella* spp. In one aspect of the invention an "infection" or "bacterial infection" refers to an infection caused by *Serratia* spp. In one aspect of the invention an "infection" or "bacterial infection" refers to an infection caused by *Staphylococcus* spp. In one aspect of the invention an "infection" or "bacterial infection" refers to an infection caused by *Streptoccocus* spp. In one aspect of the invention an "infection" or "bacterial infection" refers to an infection caused by *Stenotrophomonas* spp. In one aspect of the invention an "infection" or "bacterial infection" refers to an infection caused by *Ureaplasma* spp. In one aspect of the invention an "infection" or "bacterial infection" refers to an infection caused by aerobes. In one aspect of the invention an "infection" or "bacterial infection" refers to an infection caused by obligate anaerobes. In one aspect of the invention an "infection" or "bacterial infection" refers to an infection caused by facultative anaerobes. In one aspect of the invention an "infection" or "bacterial infection" refers to an infection caused by gram-positive bacteria. In one aspect of the invention an "infection" or "bacterial infection" refers to an infection caused by gram-negative bacteria. In one aspect of the invention an "infection" or "bacterial infection" refers to an infection caused by gram-variable bacteria. In one aspect of the invention an "infection" or "bacterial infection" refers to an infection caused by atypical respiratory pathogens. In one aspect of the invention an "infection" or "bacterial infection" refers to an infection caused by Enterics. In one aspect of the invention an "infection" or "bacterial infection" refers to an infection caused by *Shigella* spp. In one aspect of the invention an "infection" or "bacterial infection" refers to an infection caused by *Citrobacter*.

In one aspect of the invention "infection" or "bacterial infection" refers to a gynecological infection. In one aspect of the invention "infection" or "bacterial infection" refers to a respiratory tract infection (RTI). In one aspect of the invention "infection" or "bacterial infection" refers to a sexually transmitted disease. In one aspect of the invention "infection" or "bacterial infection" refers to a urinary tract infection. In one aspect of the invention "infection" or "bacterial infection" refers to acute exacerbation of chronic bronchitis (ACEB). In one aspect of the invention "infection" or "bacterial infection" refers to acute otitis media. In one aspect of the invention "infection" or "bacterial infection" refers to acute sinusitis. In one aspect of the invention "infection" or "bacterial infection" refers to an infection caused by drug resistant bacteria. In one aspect of the invention "infection" or "bacterial infection" refers to catheter-related sepsis. In one aspect of the invention "infection" or "bacterial infection" refers to chancroid. In one aspect of the invention "infection" or "bacterial infection" refers to chlamydia. In one aspect of the invention "infection" or "bacterial infection" refers to community-acquired pneumonia (CAP). In one aspect of the invention "infection" or "bacterial infection" refers to complicated skin and skin structure infection. In one aspect of the invention "infection" or "bacterial infection" refers to uncomplicated skin and skin structure infection. In one aspect of the invention "infection" or "bacterial infection" refers to endocarditis. In one aspect of the invention "infection" or "bacterial infection" refers to febrile neutropenia. In one aspect of the invention "infection" or "bacterial infection" refers to gonococcal cervicitis. In one aspect of the invention "infection" or "bacterial infection" refers to gonococcal urethritis. In one aspect of the invention "infection" or "bacterial infection" refers to hospital-acquired pneumonia (HAP). In one aspect of the invention "infection" or "bacterial infection" refers to osteomyelitis. In one aspect of the invention "infection" or "bacterial infection" refers to sepsis. In one aspect of the invention "infection" or "bacterial infection" refers to syphilis. In one aspect of the invention "infection" or "bacterial infection" refers to ventilator-associated pneumonia. In one aspect of the invention "infection" or "bacterial infection" refers to intraabdominal infections. In one aspect of the invention "infection" or "bacterial infection" refers to gonorrhoeae. In one aspect of the invention "infection" or "bacterial infection" refers to meningitis. In one aspect of the invention "infection" or "bacterial infection" refers to tetanus. In one aspect of the invention "infection" or "bacterial infection" refers to tuberculosis.

In one embodiment, it is expected that the compounds of the present invention will be useful in treating bacterial infections including, but not limited to community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

According to a further feature of the invention there is provided a method for inhibition of bacterial DNA gyrase and/or topoisomerase IV in a warm-blooded animal, such as a human being, in need of such treatment which comprises administering to said animal an effective amount of a compound of formula (I) or (IA), or a pharmaceutically acceptable salt thereof as defined hereinbefore.

According to a further feature of the invention there is provided a method of treating a bacterial infection in a warm-blooded animal, such as a human being, in need of such treatment which comprises administering to said animal an effective amount of a compound of formula (I) or (IA), or a pharmaceutically acceptable salt thereof as defined hereinbefore.

According to a further feature of the invention there is provided a method of treating a bacterial infection selected from community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epider-* midis and Vancomycin-Resistant Enterococci in a warm-blooded animal, such as a human being, in need of such treatment which comprises administering to said animal an effective amount of a compound of formula (I) or (IA), or a pharmaceutically acceptable salt thereof as defined hereinbefore.

A further feature of the present invention is a compound of formula (I) or (IA), or a pharmaceutically acceptable salt thereof for use as a medicament. Suitably the medicament is an antibacterial agent.

According to a further aspect of the invention there is provided the use of a compound of formula (I) or (IA), or a pharmaceutically acceptable salt thereof in the manufacture of a medicament for use in the production of an anti-bacterial effect in a warm-blooded animal such as a human being.

According to a further aspect of the invention there is provided the use of a compound of formula (I) or (IA), or a pharmaceutically acceptable salt thereof, in the manufacture of a medicament for use in inhibition of bacterial DNA gyrase and/or topoisomerase IV in a warm-blooded animal such as a human being.

Thus according to a further aspect of the invention there is provided the use of a compound of formula (I) or (IA), or a pharmaceutically acceptable salt thereof, in the manufacture of a medicament for use in the treatment of a bacterial infection in a warm-blooded animal such as a human being.

Thus according to a further aspect of the invention there is provided the use of a compound of formula (I) or (IA), or a pharmaceutically acceptable salt thereof, in the manufacture of a medicament for use in the treatment of a bacterial infection selected from community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci in a warm-blooded animal such as a human being.

According to a further aspect of the invention there is provided a compound of formula (I) or (IA), or a pharmaceutically acceptable salt thereof, for use in the production of an anti-bacterial effect in a warm-blooded animal such as a human being.

According to a further aspect of the invention there is provided a compound of formula (I) or (IA), or a pharmaceutically acceptable salt thereof, for use in inhibition of bacterial DNA gyrase and/or topoisomerase IV in a warm-blooded animal such as a human being.

Thus according to a further aspect of the invention there is provided a compound of formula (I) or (IA), or a pharmaceutically acceptable salt thereof, for use in the treatment of a bacterial infection in a warm-blooded animal such as a human being.

Thus according to a further aspect of the invention there is provided a compound of formula (I) or (IA), or a pharmaceutically acceptable salt thereof, for use in the treatment of a bacterial infection selected from community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci in a warm-blooded animal such as a human being.

In order to use a compound of the formula (I) or (IA), or a pharmaceutically-acceptable salt thereof, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or (IA), or a pharmaceutically-acceptable salt thereof, and a pharmaceutically-acceptable diluent or carrier.

According to a further aspect of the invention there is provided a pharmaceutical composition which comprises a compound of formula (I) or (IA), as defined hereinbefore or a pharmaceutically acceptable salt thereof, in association with a pharmaceutically acceptable excipient or carrier for use in producing an anti-bacterial effect in an warm-blooded animal, such as a human being.

According to a further aspect of the invention there is provided a pharmaceutical composition which comprises a compound of formula (I) or (IA), as defined hereinbefore or a pharmaceutically acceptable salt thereof, in association with a pharmaceutically acceptable excipient or carrier for use in inhibition of bacterial DNA gyrase and/or topoisomerase IV in an warm-blooded animal, such as a human being.

According to a further aspect of the invention there is provided a pharmaceutical composition which comprises a compound of formula (I) or (IA), as defined hereinbefore or a pharmaceutically acceptable salt thereof, in association with a pharmaceutically acceptable excipient or carrier for use in the treatment of a bacterial infection in an warm-blooded animal, such as a human being.

According to a further aspect of the invention there is provided a pharmaceutical composition which comprises a compound of formula (I) or (IA), as defined hereinbefore or a pharmaceutically acceptable salt thereof, in association with a pharmaceutically acceptable excipient or carrier for use in the treatment of a bacterial infection selected from community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci in an warm-blooded animal, such as a human being.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compounds of the invention described herein may be applied as a sole therapy or may involve, in addition to a compound of the invention, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following:

i) other antibacterial agents for example macrolides e.g. erythromycin, azithromycin or clarithromycin; quinolones e.g. ciprofloxacin or levofloxacin; β-lactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or ii) anti-infective agents for example, an antifungal triazole e.g. or amphotericin; and/or iii) biological protein therapeutics for example antibodies, cytokines, bactericidal/permeability-increasing protein (BPI) products; and/or iv) efflux pump inhibitors.

Therefore, in a further aspect of the invention there is provided a compound of the formula (I) or (IA), or a pharmaceutically acceptable salt thereof, and a chemotherapeutic agent selected from:

i) one or more additional antibacterial agents; and/or ii) one or more anti-infective agents; and/or iii) biological protein therapeutics for example antibodies, cytokines, bactericidal/permeability-increasing protein (BPI) products; and/or iv) one or more efflux pump inhibitors.

In another embodiment, the invention relates to a method of treating a bacterial infection in an animal, such as a human, comprising administering to the animal an effective amount of a compound of formula (I) or (IA), or a pharmaceutically acceptable salt thereof, and a chemotherapeutic agent selected from:

i) one or more additional antibacterial agents; and/or ii) one or more anti-infective agents; and/or iii) biological protein therapeutics for example antibodies, cytokines, bactericidal/permeability-increasing protein (BPI) products; and/or iv) one or more efflux pump inhibitors.

As stated above the size of the dose required for the therapeutic or prophylactic treatment of a particular disease state will necessarily be varied depending on the host treated, the route of administration, the severity of the illness being treated, and whether or not an additional chemotherapeutic agent is administered in combination with a compound of the invention. Preferably a daily dose in the range of 1-50 mg/kg is employed. However the daily dose will necessarily be varied depending upon the host treated, the particular route of administration, the severity of the illness being treated, and whether or not an additional chemotherapeutic agent is administered in combination with a compound of the invention. Accordingly the optimum dosage may be determined by the practitioner who is treating any particular patient.

As noted above, one embodiment of the present invention is directed to treating or preventing diseases caused by bacterial infections, wherein the bacteria comprise a GyrB ATPase or topoisomerase IV ATPase enzyme. "Treating a subject with a disease caused by a bacterial infection" includes achieving, partially or substantially, one or more of the following: the reducing or amelioration of the progression, severity and/or duration of the infection, arresting the spread of an infection, ameliorating or improving a clinical symptom or indicator associated with a the infection (such as tissue or serum components), and preventing the reoccurrence of the infection.

As used herein, the terms "preventing a bacterial infection" refer to the reduction in the risk of acquiring the infection, or the reduction or inhibition of the recurrence of the infection. In a preferred embodiment, a compound of the invention is administered as a preventative measure to a patient, preferably a human, before a surgical procedure is preformed on the patient to prevent infection.

As used herein, the term "effective amount" refers to an amount of a compound of this invention for treating or preventing a bacterial infection is an amount which is sufficient to prevent the onset of an infection, reduce or ameliorate the severity, duration, or progression, of an infection, prevent the advancement of an infection, cause the regression of an infection, prevent the recurrence, development, onset or progression of a symptom associated with an infection, or enhance or improve the prophylactic or therapeutic effect(s) of another therapy.

In addition to its use in therapeutic medicine, compounds of formula (I) or (IA), and their pharmaceutically acceptable salts, are also useful as pharmacological tools in the development and standardization of in-vitro and in-vivo test systems for the evaluation of the effects of inhibitors of DNA gyrase and/or topoisomerase IV in laboratory animals such as cats, dogs, rabbits, monkeys, rats and mice, as part of the search for new therapeutic agents.

In the above other, pharmaceutical composition, process, method, use and medicament manufacture features, the alternative and particular embodiments of the compounds of the invention described herein also apply.

EXAMPLE

The invention is now illustrated but not limited by the following Example in which unless otherwise stated:—

(i) evaporations were carried out by rotary evaporation in-vacuo and work-up procedures were carried out after removal of residual solids by filtration;

(ii) operations were generally carried out at ambient temperature, that is typically in the range 18-26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable; the structure of the end-products of the invention were generally confirmed by NMR and mass spectral techniques; proton magnetic resonance spectra is quoted and was generally determined in DMSO-$d_6$ unless otherwise stated using a Bruker DRX-300 spectrometer operating at a field strength of 300 MHz. Chemical shifts are reported in parts per million downfield from tetramethysilane as an internal standard ($\delta$ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected or using Agilent 1100 series LC/MSD equipped with Sedex 75ELSD, run in atmospheric pressure chemical ionization mode and, where appropriate, either positive ion data or negative ion data were collected; mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported;

(vi) each intermediate was purified to the standard required for the subsequent stage and was characterized in sufficient detail to confirm that the assigned structure was correct; purity was assessed by high pressure liquid chromatography, thin layer chromatography, or NMR and identity was determined by infra-red spectroscopy (IR), mass spectroscopy or NMR spectroscopy as appropriate;

(vii) the following abbreviations may be used:
ACN is acetonitrile;
CDCl_3 is deuterated chloroform;
DBU is 1,8-diazabicyclo[5.4.0]undec-7-ene;
DCM is dichloromethane;
DIEA is diisopropyl ethylamine;
DMF is N,N-dimethylformamide;
DMSO is dimethylsulfoxide;
EDC is 1-ethyl-3-(3-dimethyllaminopropyl)carbodiimide;
EtOAc is ethyl acetate;
EtOH is ethanol;
HATU is N-[(dimethylamino)-1H,2,3-triazolo[4,5-b-]pyridin-1-ylmethylene]-N-methylmethanaminium hexafluorophosphate N-oxide;
HOBT is 1-hydroxybenzotriazole;
MeOH is methanol;
MS is mass spectroscopy;
RT or rt is room temperature;
SM is starting material;
TFA is trifluoroacetic acid;
TFAA is trifluoroacetic anhydride;
THF is tetrahydrofuran; and
(viii) temperatures are quoted as ° C.

Example 1

6-(6-(3-Ethylureido)-4-(4-(trifluoromethyl)thiazol-2-yl)pyridin-3-yl)-1-((1-methylpiperidin-4-yl)methyl)-4-oxo-1,4-dihydro-1,8-naphthyridine-3-carboxylic acid

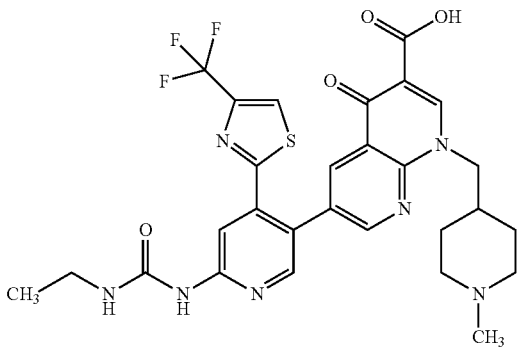 [SMILES: CCNC(=O)Nc1cc(-c2nc(C(F)(F)F)cs2)c(-c2cnc3c(c2)c(=O)c(C(=O)O)cn3CC2CCN(C)CC2)cn1]

To a solution of ethyl 6-iodo-1-((1-methylpiperidin-4-yl)methyl)-4-oxo-1,4-dihydro-1,8-naphthyridine-3-carboxylate (Intermediate 1, 952 mg, 2.32 mmol) and 6-(3-ethylureido)-4-(4-(trifluoromethyl)thiazol-2-yl)pyridin-3-ylboronic acid (Intermediate 9, 834 mg, 2.32 mmol) in 1,4-dioxane (7.5 mL) was added tetrakis(triphenylphosphine)palladium(0) (268 mg, 0.23 mmol) followed by a solution of cesium carbonate (1.51 g, 4.63 mmol) in water (2 mL). The reaction mixture was stirred at 100° C. for 2 h. 2 M lithium hydroxide (2.32 mL, 4.63 mmol) was then added and the mixture was stirred at 100° C. for 12 h. The reaction mixture was diluted with water, and the precipitate was washed with water and hexanes and then dried. The compound was purified via reverse phase HPLC (C18, 0-95% acetonitrile/water, gradient) and concentrated under reduced pressure to give 6-(6-(3-ethylureido)-4-(4-(trifluoromethyl)thiazol-2-yl)pyridin-3-yl)-1-((1-methylpiperidin-4-yl)methyl)-4-oxo-1,4-dihydro-1,8-naphthyridine-3-carboxylic acid as a light yellow solid (106.1 mg, 7%).

Calcd for $C_{28}H_{28}F_3N_7O_4S$ [M+H]$^+$: 616.17.

$^1$H NMR (d$_6$-DMSO) δ 9.54 (s, 1H), 8.92 (d, 1H), 8.66 (d, 1H), 8.59 (s, 1H), 8.45 (s, 1H), 8.24 (s, 1H), 8.17 (s, 1H), 7.54 (t, 1H), 4.6-4.55 (m, 2H), 3.26-3.17 (m, 2H), 2.17 (s, 3H), 1.92-1.75 (m, 4H), 1.49-1.3 (m, 5H), 1.11 (t, 3H).

Example 2

The following example was prepared according to procedure described for Example 1 from the indicated starting material.

| Ex | Compound | Data | SM |
|----|----------|------|----|
| 2 | 6-(6-(3-ethylureido)-4-(4-(trifluoromethyl)thiazol-2-yl)pyridin-3-yl)-1-(2-(1-methylpiperidin-4-yl)ethyl)-4-oxo-1,4-dihydro-1,8-naphthyridine-3-carboxylic acid | Calcd for $C_{29}H_{30}F_3N_7O_4S$ [M + H]$^+$: 630.24<br>$^1$H NMR (d$_6$-DMSO) δ 9.56 (s, 1H), 9.27 (s, 1H), 8.92 (s, 1H), 8.65 (d, 1H), 8.57 (s, 1H), 8.43 (s, 1H), 8.25 (s, 1H), 7.58 (s, 1H), 4.7-4.65 (m, 2H), 3.24-3.16 (m, 2H), 2.3 (s, 3H), 2.18-2.12 (m, 2H), 1.78-1.74 (m, 4H), 1.36-1.27 (m, 5H), 1.11 (d, 3H) | Intermediate 2 & Intermediate 9 |

Example 3

Ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

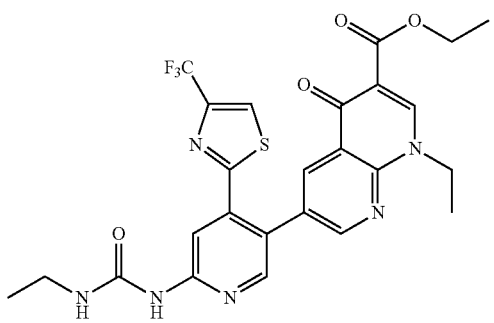 [SMILES: CCNC(=O)Nc1cc(-c2nc(C(F)(F)F)cs2)c(-c2cnc3c(c2)c(=O)c(C(=O)OCC)cn3CC)cn1]

In a round bottomed flask, ethyl 6-bromo-1-ethyl-4-oxo-1,4-dihydro-1,8-naphthyridine-3-carboxylate (Intermediate 15, 400 mg, 1.3 mmol), 6-(3-ethylureido)-4-(4-(trifluoromethyl)thiazol-2-yl)pyridin-3-ylboronic acid (Intermediate 9, 700 mg, 1.72 mmol) and cesium carbonate (3.78 g, 2.46 mmol) were combined and suspended in 10 mL of dioxane:water (8:2). The suspension was purged with argon for 15 min. then tetrakis (triphenylphosphine) palladium (140 mg, 0.2 mmol) was added under argon atmosphere and the reaction mixture was heated to 80-90° C. for 5 h. After completion of the reaction, the reaction mixture was cooled to room temperature and filtered through celite. The filtrate was concentrated under reduced pressure to a residue, to which acetonitrile was added. The precipitated solid was filtered and dried to afford 150 mg (25%) of ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate.

$^1$H NMR (400 MHz, DMSO-$d_6$): δ 1.07-1.11 (t, 3H), 1.26-1.29 (t, 3H), 1.34-1.38 (t, 3H), 3.18-3.21 (q, 2H), 4.50 (q, 2H), 7.55 (s, 1H), 8.21 (s, 1H), 8.38 (s, 1H), 8.42 (s, 1H), 8.51 (s, 1H), 8.74 (s, 1H), 8.87 (s, 1H), 9.46 (s, 1H).

LC-MS: m/z 561.32 (M+H).

Example 4

The following Example was prepared according to the procedure described for Example 3 from the starting material indicated in the table.

| Ex | Compound | Data | SM |
|---|---|---|---|
| 4 | Ethyl 6-{6-[(ethylcarbamoyl)amino]-4-[4-(trifluoromethyl)-1,3-thiazol-2-yl]pyridin-3-yl}-1-(2-hydroxyethyl)-4-oxo-1,4-dihydro-1,8-naphthyridine-3-carboxylate | $^1$H NMR (400 MHz, DMSO-$d_6$): δ 1.09-1.13 (t, 3H), 1.27-1.30 (t, 3H), 3.18-3.21 (m, 2H), 3.73-3.77 (q, 2H), 4.22-4.27 (q, 2H), 4.53-4.56 (t, 2H), 4.99-5.02 (t, 1H), 7.57 (br s, 1H), 8.23 (s, 1H), 8.39 (s, 1H), 8.45-8.46 (d, 1H), 8.53 (s, 1H), 8.75-8.77 (s, 2H), 9.48 (s, 1H). LC-MS: m/z 577 (M + H) | Intermediate 17 & Intermediate 9 |

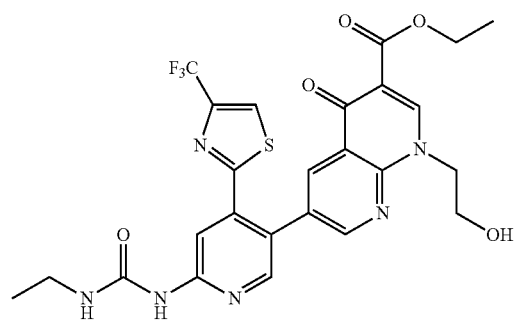 [SMILES: CCNC(=O)Nc1cc(-c2nc(C(F)(F)F)cs2)c(-c2cnc3c(c2)c(=O)c(C(=O)OCC)cn3CCO)cn1]

Example 5

Ethyl 1-cyclopropyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

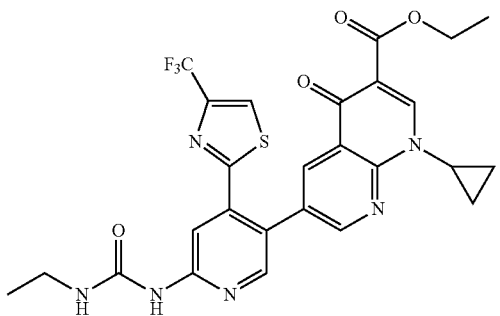 [SMILES: CCNC(=O)Nc1cc(-c2nc(C(F)(F)F)cs2)c(-c2cnc3c(c2)c(=O)c(C(=O)OCC)cn3C2CC2)cn1]

In a round bottomed flask, ethyl 6-bromo-1-cyclopropyl-4-oxo-1,4-dihydro-1,8-naphthyridine-3-carboxylate (Intermediate 16, 200 mg, 0.59 mmol), 6-(3-ethylureido)-4-(4-(trifluoromethyl)thiazol-2-yl)pyridin-3-ylboronic acid (Intermediate 9, 367 mg, 0.83 mmol) and sodium carbonate (125 mg, 1.18 mmol) were combined and suspended in dimethylformamide (10 mL). Argon gas was purged through the above suspension for 15 min. At the end of this period, tetrakis (triphenylphosphine) palladium (68 mg, 0.05 mM) was added under argon atmosphere and the reaction mixture was heated to 40° C. for 6 h. After completion of the reaction, the reaction mixture was cooled to room temperature and filtered through celite. The filtrate was poured into water and stirred for 30 min to obtain a solid which was filtered and washed with water and dried to afford 70 mg (20%) of ethyl 1-cyclopropyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate.

$^1$H NMR (400 MHz, DMSO-$d_6$): δ 1.05-1.09 (m, 2H), 1.11-1.16 (m, 2H), 1.18-1.21 (t, 3H), 1.25-1.28 (t, 3H), 3.18-3.21 (q, 2H), 3.72 (m, 1H), 4.20-4.25 (q, 2H), 7.58 (s, 1H), 8.22 (s, 1H), 8.37-8.40 (s, 2H), 8.52 (s, 1H), 8.61 (s, 1H), 8.79 (s, 1H), 9.48 (s, 1H).

LC-MS: m/z 573 (M+H).

Examples 6-7

The following Examples were prepared according to the procedure described for Example 5 from the indicated starting materials.

| Ex | Compound | Data | SM |
|---|---|---|---|
| 6 | Ethyl 6-{6-[(ethylcarbamoyl)amino]-4-[4-(trifluoromethyl)-1,3-thiazol-2-yl]pyridin-3-yl}-1-[(2S)-1-hydroxy-4-methylpentan-2-yl]-4-oxo-1,4-dihydro-1,8-naphthyridine-3-carboxylate | $^1$H NMR (400 MHz, DMSO-$d_6$): δ 0.87 (t, 6H), 1.16 (t, 3H), 1.25 (t, 3H), 1.28 (m, 1H), 1.43 (m, 1H), 1.68 (m, 1H), 3.13 (m, 2H), 3.68 (m, 2H), 4.25 (q, 2H), 5.16 (br s, 1H), 5.89 (br, 1H), 7.32 (d, 1H), 7.47 (m, 1H), 8.22 (s, 1H), 8.33 (s, 1H), 8.45 (d, 1H), 8.57 (s, 1H), 8.69 (m, 1H), 9.51 (d, 1H). LC-MS: m/z 633 (M + H) | Intermediate 18 & Intermediate 9 |
| 7 | Ethyl 6-{6-[(ethylcarbamoyl)amino]-4-[4-(trifluoromethyl)-1,3-thiazol-2-yl]pyridin-3-yl}-1-[(2S)-1-hydroxy-3,3-dimethylbutan-2-yl]-4-oxo-1,4-dihydro-1,8-naphthyridine-3-carboxylate | $^1$H NMR (400 MHz, DMSO-$d_6$): δ 0.98 (s, 9H), 1.15-1.19 (t, 3H), 1.23-1.29 (t, 3H), 3.21 (m, 2H), 4.05 (q, 2H), 4.25 (q, 2H), 5.85 (m, 1H), 7.64 (br s, 1H), 8.24 (s, 1H), 8.33 (s, 1H), 8.41 (s, 1H), 8.46 (s, 1H), 8.58 (s, 1H), 8.74 (s, 1H), 9.57 (s, 1H). LC-MS: m/z 633.29 (M + H) | Intermediate 9 and Intermediate 19 |

Example 8

1-Ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid

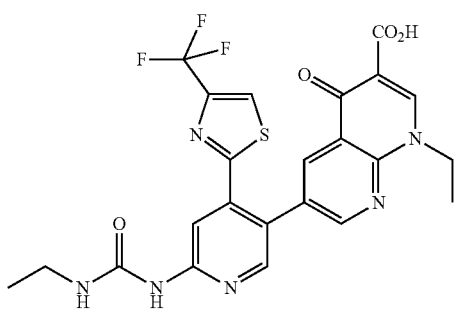 [SMILES: CCNC(=O)Nc1cc(-c2nc(C(F)(F)F)cs2)c(-c2cnc3c(c2)c(=O)c(C(=O)O)cn3CC)cn1]

To a stirred suspension of ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate (Example 3, 150 mg, 0.267 mmol) in ethanol (10 mL) 10% potassium hydroxide (0.56 mL) was added. The reaction mixture was heated to 90° C. for 1 h. After completion of the reaction, the reaction mixture was cooled to room temperature then concentrated under reduced pressure to a residue. The residue was diluted with water and acidified with 2N HCl up to pH 2-3 to obtain solid which was filtered, washed with water and dried to afford 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid 110 mg (77%).

$^1$H NMR (400 MHz, DMSO-$d_6$): δ 1.10 (t, 3H), 1.41-1.44 (t, 3H), 3.20-3.21 (m, 2H), 4.67-4.72 (q, 2H), 7.53-7.55 (t, 1H), 8.25 (s, 1H), 8.44 (s, 1H), 8.56 (s, 1H), 8.66-8.67 (d, 1H), 8.93-8.94 (d, 1H), 9.27 (s, 1H), 9.51 (s, 1H).

LC-MS: m/z 533.3 (M+H).

Examples 9-12

The following Examples were prepared according to the procedure described for Example 8 from the starting material indicated in the table.

| Ex | Compound | Data | SM |
|----|----------|------|-----|
| 9 | 1-Cyclopropyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid | $^1$H NMR (400 MHz, DMSO-$d_6$): δ 1.06-1.09 (m, 2H), 1.12 (m, 2H), 1.19-1.20 (t, 3H), 3.19-3.21 (q, 2H), 3.77 (m, 1H), 8.06 (br s, 1H), 8.38-8.40 (s, 2H), 8.53-8.59 (s, 2H), 8.68-8.78 (s, 2H), 10.01 (br s, 1H). LC-MS: m/z 545 (M + H) | Example 5 |
| 10 | 6-{6-[(ethylcarbamoyl)amino]-4-[4-(trifluoromethyl)-1,3-thiazol-2-yl]pyridin-3-yl}-1-(2-hydroxyethyl)-4-oxo-1,4-dihydro-1,8-naphthyridine-3-carboxylic acid | $^1$H NMR (400 MHz, DMSO-$d_6$): δ 1.09-1.13 (t, 3H), 3.20-3.21 (m, 2H), 3.80 (q, 2H), 4.71-4.73 (t, 2H), 5.02-5.04 (t, 1H), 7.54-7.55 (s, 1H), 8.24 (s, 1H), 8.44 (s, 1H), 8.56 (s, 1H), 8.68 (s, 1H0, 8.92 (s, 1H), 9.08 (s, 1H), 9.51 (s, 1H). LC-MS: m/z 549.0 (M + H). | Example 4 |

-continued

| Ex | Compound | Data | SM |
|---|---|---|---|
| 11 | 6-{6-[(ethylcarbamoyl)amino]-4-[4-(trifluoromethyl)-1,3-thiazol-2-yl]pyridin-3-yl}-1-[(2S)-1-hydroxy-4-methylpentan-2-yl]-4-oxo-1,4-dihydro-1,8-naphthyridine-3-carboxylic acid | $^1$H NMR (400 MHz, DMSO-$d_6$): δ 0.86 (d, 6H), 1.12 (t, 3H), 1.40 (m, 1H), 1.78 (m, 1H), 1.82 (br, 1H), 3.19 (t, 2H), 3.70 (m, 3H), 5.20 (s, 1H), 6.00 (s, 1H), 7.53 (s, 1H), 8.23 (s, 1H), 8.46 (s, 1H), 8.59 (s, 1H), 8.68 (s, 1H), 8.91 (s, 1H), 9.06 (s, 1H), 9.52 (s, 1H). LC-MS: m/z 605.3 (M + H). | Example 6 |
| 12 | 6-{6-[(ethylcarbamoyl)amino]-4-[4-(trifluoromethyl)-1,3-thiazol-2-yl]pyridin-3-yl}-1-[(2S)-1-hydroxy-3,3-dimethylbutan-2-yl]-4-oxo-1,4-dihydro-1,8-naphthyridine-3-carboxylic acid | $^1$H NMR (400 MHz, DMSO-$d_6$): δ 0.98 (s, 9H), 1.15 (t, 3H), 3.22 (m, 2H), 4.02 (q, 2H), 5.09 (t, 1H), 5.96 (m, 1H), 7.53 (br s, 1H), 8.23 (s, 1H), 8.46 (s, 1H), 8.59 (s, 1H), 8.69 (s, 1H), 8.92 (s, 1H), 9.00 (s, 1H), 9.52 (s, 1H). LC-MS: m/z 605.4 (M + H). | Example 7 |

Example 13

1-(2-{[bis(benzyloxy)phosphoryl]oxy}ethyl)-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid

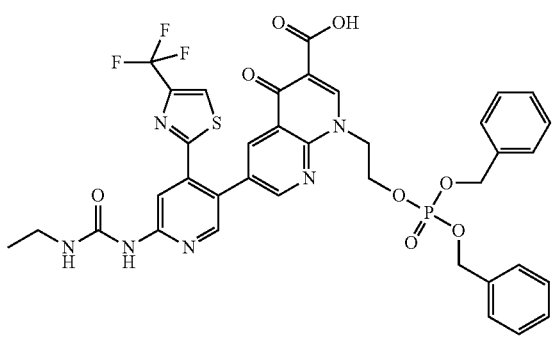 [SMILES: CCNC(=O)Nc1cc(-c2nc(C(F)(F)F)cs2)c(-c2cnc3c(c2)c(=O)c(C(=O)O)cn3CCOP(=O)(OCc2ccccc2)OCc2ccccc2)cn1]

To a stirred suspension of ethyl 1-(2-{[bis(benzyloxy)phosphoryl]oxy}ethyl)-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate (Example 30, 210 mg, 0.2511 mmol) in ethanol (20 mL), 10% potassium hydroxide (0.2 mL) was added. The reaction mixture was heated to 60° C. for 30 min. After completion of the reaction, the reaction mixture was cooled to room temperature and concentrated under reduced pressure to a residue. The residue was diluted with water and acidified with 2N hydrochloric acid solution to pH 4 to obtain solid which was filtered, washed with water and dried to afford 1-(2-{[bis(benzyloxy)phosphoryl]oxy}ethyl)-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid 150 mg (84%).

$^1$H NMR (400 MHz, DMSO-$d_6$): δ 1.14 (t, 3H), 3.21 (q, 2H), 4.41 (t, 2H), 4.88 (t, 2H), 4.93 (m, 4H), 7.15-7.38 (m, 10H), 7.56 (d, 1H), 8.21 (s, 1H), 8.39 (s, 1H), 8.50 (s, 1H), 8.62 (d, 1H), 8.91 (d, 1H), 9.22 (s, 1H), 9.54 (s, 1H).

LC-MS: m/z 809 (M+H).

Example 14

6-{6-[(ethylcarbamoyl)amino]-4-[4-(trifluoromethyl)-1,3-thiazol-2-yl]pyridin-3-yl}-4-oxo-1-[2-(phosphonooxy)ethyl]-1,4-dihydro-1,8-naphthyridine-3-carboxylic acid

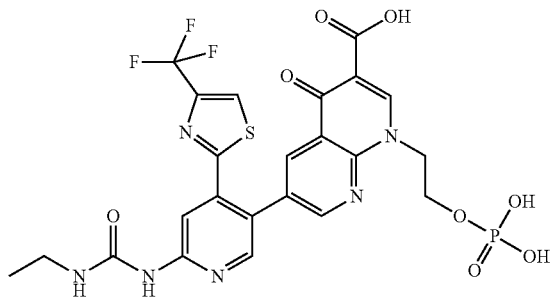 [SMILES: CCNC(=O)Nc1cc(-c2nc(C(F)(F)F)cs2)c(-c2cnc3c(c2)c(=O)c(C(=O)O)cn3CCOP(=O)(O)O)cn1]

1-(2-{[bis(benzyloxy)phosphoryl]oxy}ethyl)-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid (Example 13, 220 mg, 0.27 mmol) was dissolved in dry dichloromethane (30 mL), the reaction mixture was cooled to 0° C. Trimethylsilyl bromide (83.31 mg, 0.54 mmol) was added and the mixture was stirred for 2 h at room temperature. A solid formed on the walls of round bottom flask. The solvent was decanted and the solid was washed with ethyl acetate (20 mL) to give crude compound. The crude compound was dissolved in methanol (20 mL) and water (50 mL) was added to precipitate a solid compound which was filtered and dried to give crude compound. The crude compound was purified preparative HPLC to afford 45 mg (25.9%) of 6-{6-[(ethylcarbamoyl)amino]-4-[4-(trifluoromethyl)-1,3-thiazol-2-yl]pyridin-3-yl}-4-oxo-1-[2-(phosphonooxy)ethyl]-1,4-dihydro-1,8-naphthyridine-3-carboxylic acid.

$^1$H NMR (400 MHz, CH$_3$COOD): δ 1.32 (t, 3H), 3.48 (q, 2H), 4.47 (t, 2H), 5.00 (t, 2H), 7.91 (s, 1H), 8.19 (s, 1H), 8.49 (s, 1H), 8.94 (2s, 1H), 9.28 (s, 1H).

LC-MS: m/z 629 (M+H).

Example 15

Ethyl 1-[2-(dimethylamino)ethyl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

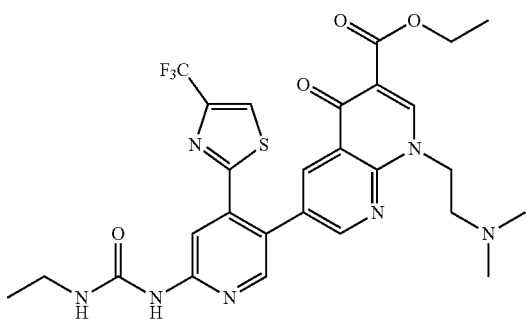 [SMILES: CCNC(=O)Nc1cc(-c2nc(C(F)(F)F)cs2)c(-c2cnc3c(c2)c(=O)c(C(=O)OCC)cn3CCN(C)C)cn1]

In a round bottomed flask ethyl 6-bromo-1-[2-(dimethylamino)ethyl]-4-oxo-1,4-dihydro-1,8-naphthyridine-3-carboxylate (Intermediate 21, 200 mg, 0.54 mmol), 6-(3-ethylureido)-4-(4-(trifluoromethyl)thiazol-2-yl)pyridin-3-ylboronic acid (Intermediate 9, 288 mg, 0.65 mmol) and sodium carbonate (115 mg, 1.08 mmol) were combined and suspended in dimethylformamide (10 mL) and purged with argon gas for 10 min. Tetrakis (triphenylphosphine) palladium (62 mg, 0.05 mmol) was added under argon atmosphere and the reaction mixture was heated to 90° C. for 2 h. After completion of the reaction, the reaction mixture was cooled to room temperature and filtered through celite. The filtrate was poured into water and was stirred for 20 min. The obtained solid was filtered and washed with water then dried to afford 110 mg (33%) of ethyl 1-[2-(dimethylamino)ethyl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate.

$^1$H NMR (400 MHz, DMSO-d$_6$): δ 1.09 (t, 3H), 1.27 (t, 3H), 2.19 (s, 6H), 2.68 (s, 2H), 3.23 (t, 2H), 4.23 (q, 2H), 4.62 (q, 2H), 7.57 (m, 1H), 8.21 (s, 1H), 8.41-8.44 (s, 2H), 8.55 (s, 1H), 8.74 (s, 1H), 8.81 (s, 1H), 9.50 (s, 1H).

LC-MS: m/z 604 (M+H).

Example 16

1-[2-(dimethylamino)ethyl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid

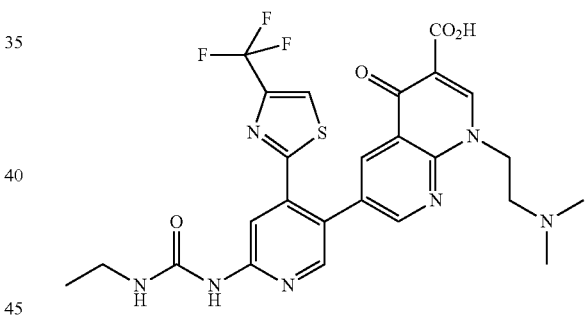

To a stirred suspension of ethyl 1-[2-(dimethylamino)ethyl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate (Example 15, 100 mg, 0.16 mmol) in ethanol (10 mL) 10% potassium hydroxide (0.3 mL) was added. The reaction mixture was heated to 90° C. for 1 h. After completion of the reaction, the reaction mixture was cooled to room temperature then concentrated under reduced pressure to a residue. The residue was diluted with water and acidified with 2N HCl to pH 2-3 to obtain a solid which was filtered, washed with water and dried to afford 50 mg of crude product. This was purified by preparative HPLC to give 15 mg (15%) of 1-[2-(dimethylamino)ethyl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid.

$^1$H NMR (400 MHz, DMSO-d$_6$): δ 1.09 (t, 3H), 2.51 (s, 6H), 2.68 (t, 2H), 3.20 (t, 2H), 4.77 (q, 2H), 7.55 (s, 1H), 8.14 (s, 1H), 8.25 (s, 1H), 8.46 (s, 1H), 8.59 (s, 2H), 8.67 (s, 1H), 8.92 (s, 1H), 9.15 (s, 1H), 9.54 (s, 1H).

LC-MS: m/z 576.2 (M+H).

Example 17

2-hydroxyethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

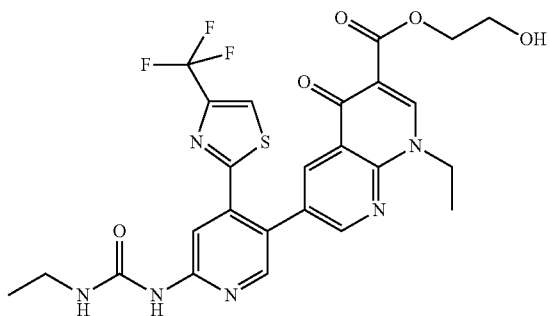 [SMILES: CCNC(=O)Nc1cc(-c2nc(C(F)(F)F)cs2)c(-c2cnc3c(c2)c(=O)c(C(=O)OCCO)cn3CC)cn1]

2-Hydroxyethyl 6-bromo-1-ethyl-4-oxo-1,4-dihydro-1,8-naphthyridine-3-carboxylate (Intermediate 23, 170 mg, 0.50 mmol) was dissolved in dimethylformamide (25 mL), purged with argon, tetrakis (triphenylphosphine) palladium (57 mg, 0.049 mmol) followed by 6-(3-ethylureido)-4-(4-(trifluoromethyl)thiazol-2-yl)pyridin-3-ylboronic acid (Intermediate 9, 264 mg, 0.598 mmol) was added and stirred for 20 min at room temperature, sodium carbonate solution (231 mg, 2 mmol) (dissolved in minimum amount of water) was added to reaction mixture and the mixture was heated to 90° C. for 3 h. The reaction mixture was passed through a celite bed and the celite was washed with dimethylformamide. The dimethylformamide layer was poured into water (100 mL) and a solid precipitate formed. The solid was filtered and dried then purified by flash column chromatography over silica gel (100-200 mesh) using MeOH (0-6%) in $CHCl_3$ as an eluent to afford 168 mg (60%) 2-hydroxyethyl 1-ethyl-6-{6-[(ethylcarbamoyl)amino]-4-[(trifluoromethyl)-1,3-thiazol-2-yl]pyridin-3-yl}-4-oxo-1,4-dihydro-1,8-naphthyridine-3-carboxylate as white solid.

$^1$-NMR (DMSO-$d_6$): δ 1.12 (t, 3H), 1.41 (t, 3H), 3.21 (q, 2H), 3.68 (q, 2H), 4.2 (q, 2H), 4.52 (q, 2H), 4.87 (t, 2H), 7.61 (d, 1H), 8.22 (s, 1H), 8.39 (s, 1H), 8.42 (s, 1H), 8.56 (s, 1H), 8.79 (s, 1H), 8.98 (s, 1H), 9.52 (s, 1H).

LC-MS: m/z 577.3 (M+H).

Example 18

3-hydroxypropyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

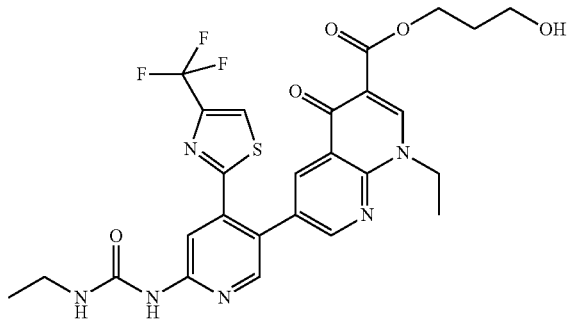 [SMILES: CCNC(=O)Nc1cc(-c2nc(C(F)(F)F)cs2)c(-c2cnc3c(c2)c(=O)c(C(=O)OCCCO)cn3CC)cn1]

3-Hydroxypropyl 6-bromo-1-ethyl-4-oxo-1,4-dihydro-1,8-naphthyridine-3-carboxylate (Intermediate 24, 400 mg, 1.46 mmol) was dissolved in dimethylformamide (35 mL) and the solution was purged with argon. Tetrakis (triphenylphosphine) palladium (167 mg, 0.14 mM) followed by 6-(3-ethylureido)-4-(4-(trifluoromethyl)thiazol-2-yl)pyridin-3-ylboronic acid (Intermediate 9, 775 mg, 1.75 mmol) was added and the mixture was stirred for 20 min at room temperature. Sodium carbonate solution (678 mg, 5.84 mmol) (dissolved in minimum amount of water) was added and the reaction mixture was heated to 90° C. for 3 h. The reaction mixture was passed through celite and the celite was washed with dimethylformamide. The dimethylformamide layer was poured into water (100 mL) and a precipitate formed. The precipitate was filtered and dried then purified by flash column chromatography over silica gel (100-200 mesh) using methanol (5%) in chloroform as eluent to afford 360 mg (65%) 3-hydroxypropyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate as white solid.

NMR (DMSO-$d_6$): δ 1.12 (t, 3H), 1.41 (t, 3H), 1.84 (q, 2H), 3.21 (q, 2H), 3.59 (m, 2H), 4.26 (t, 2H), 4.58 (q, 2H), 7.6 (m, 1H), 8.24 (s, 1H), 8.41 (s, 1H), 8.47 (d, 1H), 8.54 (s, 1H), 8.78 (d, 1H), 8.92 (s, 1H), 9.44 (s, 1H).

LC-MS: m/z 591.3 (M+H).

Example 19

2-{[bis(benzyloxy)phosphoryl]oxy}ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

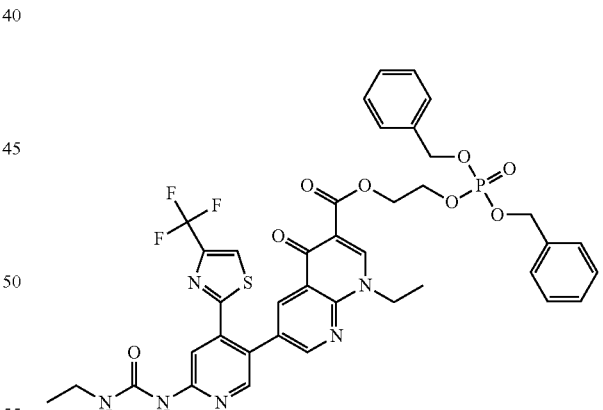

2-{[Bis(benzyloxy)phosphoryl]oxy}ethyl 6-bromo-1-ethyl-4-oxo-1,4-dihydro-1,8-naphthyridine-3-carboxylate (Intermediate 25, 80 mg, 0.133 mmol) was dissolved in dimethylformamide (15 mL), and the solution was purged with argon. Tetrakis (triphenylphosphine) palladium (15 mg, 0.013 mmol) and 6-(3-ethylureido)-4-(4-(trifluoromethyl)thiazol-2-yl)pyridin-3-ylboronic acid (Intermediate 9, 71 mg, 0.16 mmol) were added and the mixture was stirred for 20 min at room temperature. Sodium carbonate solution (57 mg, 0.53 mmol) (dissolved in minimum amount of water) was added, and the reaction mixture was heated to 90° C. for 3 h. The reaction mixture was passed through celite and the celite was washed with dimethylformamide. The dimethylformamide layer was poured into water (100 mL) and a precipitate formed. The solid was filtered and dried then purified by flash column chromatography over silica gel (0-8% MeOH/CHCl$_3$) to afford 70 mg (63%) of 2-{[bis(benzyloxy)phosphoryl]oxy}ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate as white solid.

NMR (DMSO-d$_6$) δ:: 1.14 (t, 3H), 1.38 (t, 3H), 3.21 (q, 2H), 4.21-4.51 (m, 6H), 5.06 (m, 1H), 7.27 (m, 10H), 7.61 (m, 1H), 8.24 (s, 1H), 8.39 (s, 1H), 8.42 (d, 1H), 8.54 (s, 1H), 8.78 (d, 1H), 8.97 (s, 1H), 9.56 (s, 1H).

Example 20

2-(phosphonooxy)ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

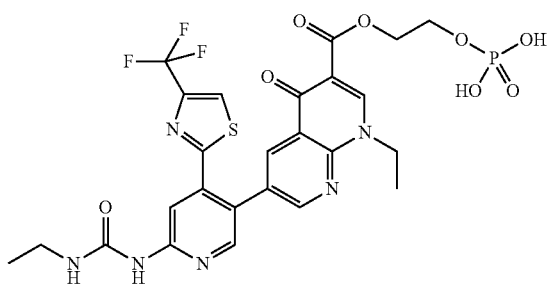 [SMILES: CCNC(=O)Nc1cc(-c2nc(C(F)(F)F)cs2)c(-c2cnc3c(c2)c(=O)c(C(=O)OCCOP(=O)(O)O)cn3CC)cn1]

2-{[Bis(benzyloxy)phosphoryl]oxy}ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate (Example 19, 390 mg, 0.46 mmol) was dissolved in dry dichloromethane (30 mL), and the reaction mixture was cooled to 0° C. Trimethylsilyl bromide (142 mg, 0.93 mmol) was added and the mixture was stirred for 16 h at room temperature to give a solid compound. The solvent was decanted and the solid was washed with ethyl acetate (30 mL). The solid was dissolved in methanol (20 mL) and water (30 mL) was added to precipitate a solid compound which was filtered and dried to afford 170 mg (34%) of 3-(phosphonooxy)propyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate.

NMR (DMSO-d$_6$): δ 1.14 (t, 3H), 1.41 (t, 3H), 3.17 (q, 2H), 4.13 (q, 2H), 4.29 (t, 2H), 4.53 (t, 2H), 7.59 (d, 1H), 8.23 (s, 1H), 8.40 (s, 1H), 8.46 (s, 1H), 8.54 (s, 1H), 8.78 (s, 1H), 9.03 (s, 1H), 9.52 (s, 1H).

LC-MS: m/z 657.2 (M+H).

Example 21

3-{[Bis(benzyloxy)phosphoryl]oxy}propyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

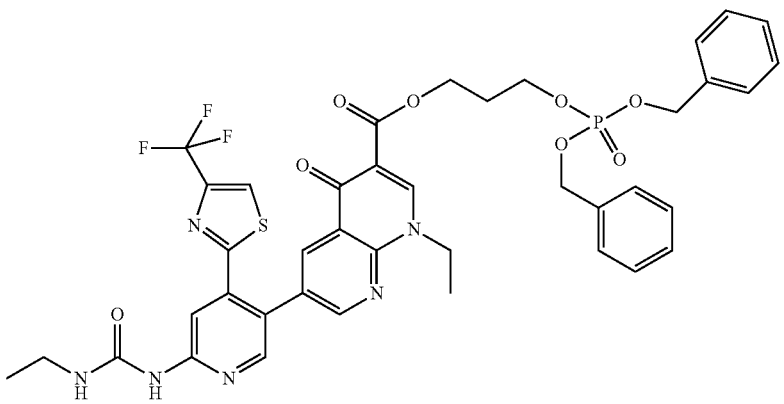 [SMILES: CCNC(=O)Nc1cc(-c2nc(C(F)(F)F)cs2)c(-c2cnc3c(c2)c(=O)c(C(=O)OCCCOP(=O)(OCc2ccccc2)OCc2ccccc2)cn3CC)cn1]

3-{[Bis(benzyloxy)phosphoryl]oxy}propyl 6-bromo-1-ethyl-4-oxo-1,4-dihydro-1,8-naphthyridine-3-carboxylate (Intermediate 26, 750 mg, 1.21 mmol) was dissolved in dimethylformamide (25 mL) and the solution was purged with argon. Tetrakis (triphenylphosphine) palladium (145 mg, 0.12 mmol) followed by 6-(3-ethylureido)-4-(4-(trifluoromethyl)thiazol-2-yl)pyridin-3-ylboronic acid (Intermediate 9, 645 mg, 1.46 mmol) was added and the mixture was stirred for 20 min at room temperature. Sodium carbonate solution (516 mg, 4.87 mmol) (dissolved in minimum amount of water) was added to reaction mixture and it was heated to 90° C. for 3 h. The reaction mixture was passed through celite bed and the celite was washed with dimethylformamide. The dimethylformamide layer was poured into water (100 mL) and a precipitate formed. The solid was filtered and dried then purified by flash column chromatography over silica gel (100-200 mesh). The product was eluted with gradient of MeOH/CHCl$_3$ (0-6%) to afford 650 mg (65%) 3-{[bis(benzyloxy)phosphoryl]oxy}propyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate as white solid.

NMR (DMSO-d$_6$): 1.11 (t, 3H), 1.37 (t, 3H), 1.99 (q, 2H), 3.23 (q, 2H), 4.18-4.27 (m, 4H), 4.47 (q, 2H), 5.04 (m, 4H), 7.27-7.44 (m, 10H), 7.58 (d, 1H), 8.24 (s, 1H), 8.39 (s, 1H), 8.44 (s, 1H), 8.53 (s, 1H), 8.76 (s, 1H), 8.90 (s, 1H), 9.51 (s, 1H).

Example 22

3-(Phosphonooxy)propyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

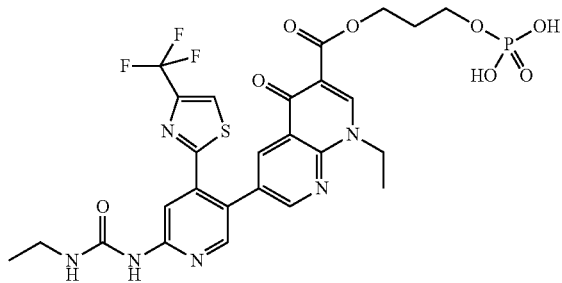 [SMILES: CCNC(=O)Nc1cc(-c2nc(C(F)(F)F)cs2)c(-c2cnc3c(c2)c(=O)c(C(=O)OCCCOP(=O)(O)O)cn3CC)cn1]

3-{[Bis(benzyloxy)phosphoryl]oxy}propyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate (Example 21, 700 mg, 0.82 mM) was dissolved in dry dichloromethane (40 mL), and the reaction mixture was cooled to 0° C. Trimethylsilyl bromide (251 mg, 1.64 mmol) was added and the mixture was stirred for 16 h at room temperature. A solid formed on the walls of round bottom flask. The solvent was decanted and the solid was washed with ethyl acetate (30 mL) to give crude compound. The crude compound was dissolved in methanol (20 mL) and water (30 mL) was added to precipitate the product which was filtered and dried to afford 230 mg (35%) of 3-(phosphonooxy)propyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate.

NMR (DMSO-d$_6$): δ 1.11 (t, 3H), 1.38 (t, 3H), 2.00 (q, 2H), 2.34 (q, 2H), 3.96 (t, 2H), 4.27 (t, 2H), 4.55 (t, 2H), 7.57 (s, 1H), 8.23 (s, 1H), 8.39 (s, 1H), 8.46 (s, 1H), 8.52 (s, 1H), 8.75 (s, 1H), 8.92 (s, 1H), 9.48 (s, 1H).

Example 23

Ethyl 1-[(2S)-1-{[(benzyloxy)(hydroxy)phosphoryl]oxy}-4-methylpentan-2-yl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate

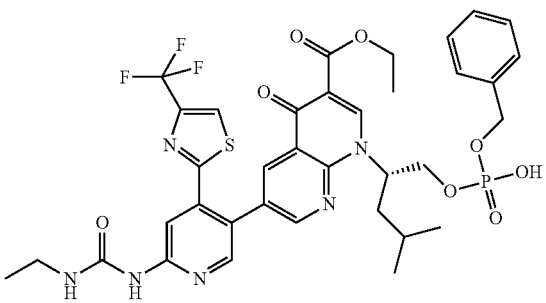 [SMILES: CCNC(=O)Nc1cc(-c2nc(C(F)(F)F)cs2)c(-c2cnc3c(c2)c(=O)c(C(=O)OCC)cn3[C@H](COP(=O)(O)OCc2ccccc2)CC(C)C)cn1]

In a round bottomed flask ethyl 1-[(2S)-1-{[bis(benzyloxy)phosphoryl]oxy}-4-methylpentan-2-yl]-6-bromo-4-oxo-1,4-dihydro-1,8-naphthyridine-3-carboxylate (Intermediate 28, 700 mg, 1.05 mmol), 6-(3-ethylureido)-4-(4-(trifluoromethyl)thiazol-2-yl)pyridin-3-ylboronic acid (Intermediate 9, 565 mg, 1.28 mmol) and aqueous sodium carbonate (125 mg, 1.18 mmol) were combined and suspended in dimethylformamide (10 mL). Argon gas was purged through the above suspension for 15 min. Tetrakis (triphenylphosphine) palladium (122 mg, 0.10 mmol) was added under argon atmosphere and the reaction mixture was heated to 80° C. for 3 h. After completion of the reaction, the reaction mixture was cooled to room temperature, filtered through celite, the filtrate was poured into water to give a solid. The solid was filtered and washed with water then dried to afford 330 mg (50%) of ethyl 1-[(2S)-1-{[(benzyloxy)(hydroxy)phosphoryl]oxy}-4-methylpentan-2-yl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate.

$^1$H NMR (400 MHz, DMSO-d$_6$): δ 0.95 (d, 6H), 1.12 (t, 3H), 1.28 (t, 3H), 1.39 (d, 1H), 1.72 (d, 1H), 1.86 (d, 1H), 3.21 (q, 2H), 4.01-4.21 (d, 2H), 4.23 (q, 2H), 4.63 (d, 2H), 6.01 (d, 1H), 7.24 (m, 5H), 8.24 (s, 1H), 8.38 (s, 1H), 8.45 (s, 1H), 8.52 (s, 1H), 8.73 (s, 1H), 8.78 (s, 1H), 9.56 (s, 1H).

LC-MS: m/z 803 (M+H).

Example 24

1-[(2S)-1-{[(benzyloxy)(hydroxy)phosphoryl]oxy}-4-methylpentan-2-yl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid

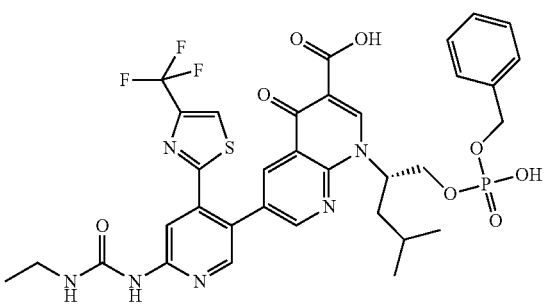 [SMILES: CCNC(=O)Nc1cc(-c2nc(C(F)(F)F)cs2)c(-c2cnc3c(c2)c(=O)c(C(=O)O)cn3[C@H](COP(=O)(O)OCc2ccccc2)CC(C)C)cn1]

To a stirred suspension of ethyl 1-[(2S)-1-{[(benzyloxy)(hydroxy)phosphoryl]oxy}-4-methylpentan-2-yl]-6-{6-[(ethylcarbamoyl)amino]-4-[4-(trifluoromethyl)-1,3-thiazol-2-yl]pyridin-3-yl}-4-oxo-1,4-dihydro-1,8- naphthyridine-3-carboxylate (Example 23, 330 mg, 0.41 mmol) in ethanol (20 mL) was added 10% potassium hydroxide (69 mg, 1.23 mmol). The reaction mixture was heated to 60-65° C. overnight. The reaction mixture was cooled and then washed with ethyl acetate (20 mL). The pH of the aqueous layer was adjusted to 4 with dilute hydrochloric acid (2N) solution to give a solid precipitate which was filtered and dried to afford 120 mg (30%) of 1-[(2S)-1-{[(benzyloxy)(hydroxy)phosphoryl]oxy}-4-methylpentan-2-yl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid.

$^1$H NMR (400 MHz, DMSO-$d_6$): δ 0.94 (d, 6H), 1.16 (t, 3H), 1.39 (d, 1H), 1.81 (d, 1H), 3.21 (q, 2H), 4.19 (d, 1H), 4.41 (d, 1H), 4.77 (d, 2H), 6.22 (d, 1H), 7.28 (m, 5H), 7.62 (d, 2H), 8.44 (s, 1H), 8.42 (s, 1H), 8.53 (s, 1H), 8.68 (s, 1H), 8.91 (s, 1H), 9.18 (s, 1H), 9.54 (s, 1H).

LC-MS: m/z 776 (M+H).

Example 25

6-{6-[(ethylcarbamoyl)amino]-4-[4-(trifluoromethyl)-1,3-thiazol-2-yl]pyridin-3-yl}-1-[(2S)-4-methyl-1-(phosphonooxy)pentan-2-yl]-4-oxo-1,4-dihydro-1,8-naphthyridine-3-carboxylic acid

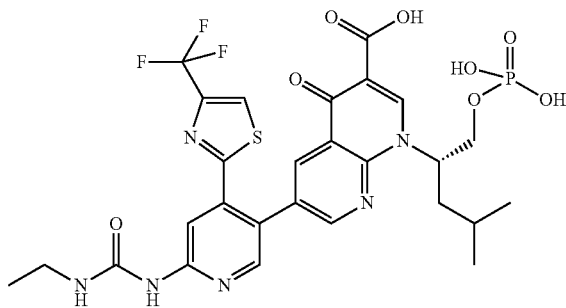 [SMILES: CCNC(=O)Nc1cc(-c2nc(C(F)(F)F)cs2)c(-c2cnc3c(c2)c(=O)c(C(=O)O)cn3[C@H](COP(=O)(O)O)CC(C)C)cn1]

1-[(2S)-1-{[(Benzyloxy)(hydroxy)phosphoryl]oxy}-4-methylpentan-2-yl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid (Example 24, 700 mg, 0.90 mmol) was dissolved in dry dichloromethane (30 mL), then the reaction mixture was cooled to 0° C. Trimethylsilyl bromide (TMS-Br) (0.55 g, 3.61 mmol) was added and the mixture was stirred for 2 h at room temperature. A solid formed on the walls of the round bottom flask, and the solvent was decanted. The solid was washed with ethyl acetate (20 mL) then dissolved in methanol (20 mL) and water (50 mL) was added to precipitate a solid which was filtered and dried to give crude compound (380 mg). The crude compound was purified by preparative HPLC to afford 220 mg (25.9%) of 6-{6-[(ethylcarbamoyl)amino]-4-[4-(trifluoromethyl)-1,3-thiazol-2-yl]pyridin-3-yl}-1-[(2S)-4-methyl-1-(phosphonooxy)pentan-2-yl]-4-oxo-1,4-dihydro-1,8-naphthyridine-3-carboxylic acid.

$^1$H NMR (400 MHz, DMSO-$d_6$): δ 0.86 (d, 6H), 1.12 (t, 3H), 1.23 (d, 1H), 1.80 (d, 1H), 1.95 (d, 1H), 3.24 (q, 2H), 4.08 (2d, 2H), 6.11 (d, 1H), 7.13 (s, 2H), 7.65 (s, 1H), 8.26 (s, 1H), 8.38 (s, 1H), 8.56 (s, 1H), 8.62 (s, 1H), 8.90 (s, 1H), 8.99 (s, 1H), 9.59 (s, 1H).

LC-MS: m/z 685.3 (M+H).

Example 26

The following Example was prepared according to the procedure described for Example 23 from the starting material indicated.

| Ex | Compound | Data | SM |
|---|---|---|---|
| 26 | (R)-ethyl 1-(1-(tert-butoxycarbonyl)piperidin-3-yl)-6-(6-(3-ethylureido)-4-(4-(trifluoromethyl)thiazol-2-yl)pyridin-3-yl)-4-oxo-1,4-dihydro-1,8-naphthyridine-3-carboxylate | MS (ES) (M + H)$^+$: 716 for $C_{33}H_{36}F_3N_7O_6S$ | Intermediate 9 and Intermediate 30 |

Example 27

(R)-ethyl 6-(6-(3-ethylureido)-4-(4-(trifluoromethyl)thiazol-2-yl)pyridin-3-yl)-4-oxo-1-(piperidin-3-yl)-1,4-dihydro-1,8-naphthyridine-3-carboxylate

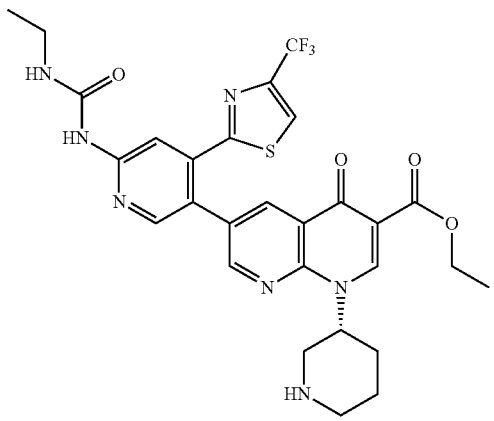 [SMILES: CCNC(=O)Nc1cc(-c2nc(C(F)(F)F)cs2)c(-c2cnc3c(c2)c(=O)c(C(=O)OCC)cn3[C@@H]2CCCNC2)cn1]

To a solution of (R)-ethyl 1-(1-(tert-butoxycarbonyl)piperidin-3-yl)-6-(6-(3-ethylureido)-4-(4-(trifluoromethyl)thiazol-2-yl)pyridin-3-yl)-4-oxo-1,4-dihydro-1,8-naphthyridine-3-carboxylate (300 mg) in dioxane (3 mL) was added 4 N HCl in dioxane (2 eq). The reaction mixture was stirred at room temperature overnight and the solid that formed was collected by filtration to provide the desired product.

MS (ES)(M+H)$^+$: 716 for $C_{33}H_{36}F_3N_7O_6S$.

Example 28

(R)-ethyl 6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydro-1,8-naphthyridine-3-carboxylate

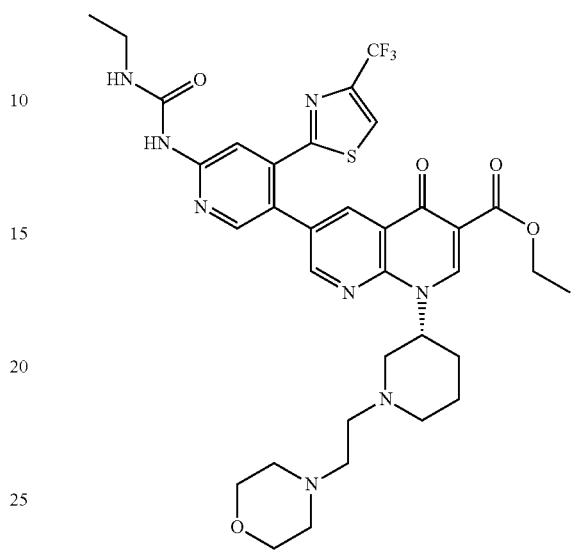

(R)-ethyl 6-(6-(3-ethylureido)-4-(4-(trifluoromethyl)thiazol-2-yl)pyridin-3-yl)-4-oxo-1-(piperidin-3-yl)-1,4-dihydro-1,8-naphthyridine-3-carboxylate (Example 27, 0.050 g, 0.08 mmol) was taken up in THF (2 mL) and 2-morpholinoacetaldehyde 2,2,2-trifluoroacetate (0.024 g, 0.10 mmol) and DIEA (0.043 mL, 0.24 mmol) were added. The mixture was stirred at RT for 15 min. then sodium triacetoxyborohydride (0.078 g, 0.37 mmol) was added and reaction was stirred at RT for 6 hrs. The reaction was then quenched with NaHCO$_3$ and extracted with DCM three times. Organics were combined and dried over Na$_2$SO$_4$ then the solvent was removed in vacuo. The residue was purified by flash column chromatography on silica gel using (dichloromethane-methanol) to give (R)-ethyl 6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydro-1,8-naphthyridine-3-carboxylate (0.026 mg, 44%).

MS (ES)(M+H)$^+$: 729 for $C_{34}H_{39}F_3N_8O_5S$.

Example 29

The following Example was prepared according to the procedure described for Example 16 from the starting materials indicated.

| Ex | Compound | Data | SM |
|---|---|---|---|
| 29 | (R)-ethyl 6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydroquinoline-3-carboxylic acid 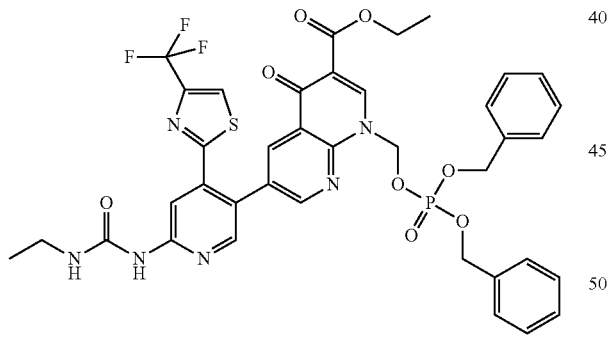 | MS (ES) (M + H)$^+$: 701 for $C_{32}H_{35}F_3N_8O_5S$<br>$^1$H NMR (300 MHz, DMSO-$d_6$) δ 14.25-14.65 (m, 1 H), 9.70 (br. s., 1 H), 9.60 (br. s., 1 H), 8.93 (s, 1 H), 8.67 (s, 1 H), 8.58 (s, 1 H), 8.43 (s, 1 H), 8.29 (s, 1 H), 7.71 (br. s., 1 H), 5.60 (br. s., 1 H), 3.53 (br. s., 4 H), 3.16-3.26 (m, 2 H), 2.82-3.02 (m, 2 H), 2.60 (br. s., 2 H), 2.37 (br. s., 4 H), 1.97 (br. s., 2 H), 1.67 (d, J = 15.07 Hz, 2 H), 1.11 (t, J = 7.16 Hz, 3 H). | Example 28 |

Example 30

Ethyl 1-(2-{[bis(benzyloxy)phosphoryl]oxy}ethyl)-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate Ethyl 6-{6-[(ethylcarbamoyl)amino]-4-[4-(trifluoromethyl)-1,3-thiazol-2-yl]pyridin-3-yl}-1-(2-hydroxyethyl)-4-oxo-1,4-dihydro-1,8-naphthyridine-3-carboxylate (Example 4, 880 mg, 1.52 mmol) and triphenylphosphine (1.66 g, 6.35 mmol) was dissolved in tetrahydrofuran (100 mL). Diisopropyl azodicarboxylate [DIAD] (1.27 g, 6.35 mmol) was added and the mixture was stirred for 4 h at room temperature. The mixture was concentrated under reduced pressure to give a crude compound which was purified by flash column chromatography over silica gel (20-100% ethyl acetate/pet ether) to afford 600 mg (65%) of ethyl 1-(2-{[bis(benzyloxy)phosphoryl]oxy}ethyl)-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate.

$^1$H NMR (400 MHz, DMSO-$d_6$): δ 1.08 (t, 3H), 1.21 (t, 3H), 3.21 (q, 2H), 4.19 (q, 2H), 4.35 (t, 2H), 4.79 (t, 2H), 4.89 (m, 4H), 7.18-7.40 (m, 10H), 7.56 (d, 1H), 8.22 (s, 1H), 8.36 (s, 1H), 8.44 (2s, 2H), 8.75 (s, 1H), 8.86 (s, 1H), 9.51 (s, 1H). MASS (APCI+ve Scan): m/z 837 (M+H).

Example 31

S)-6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydro-1,8-naphthyridine-3-carboxylic acid

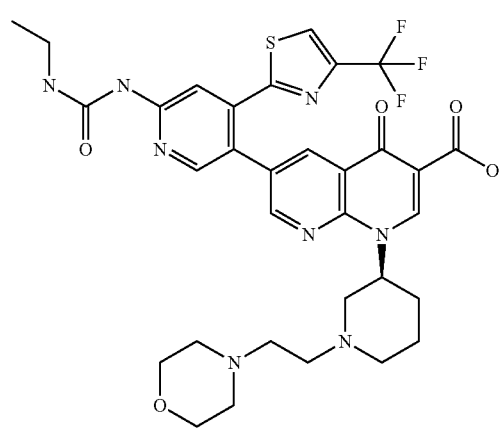 [SMILES: CCNC(=O)Nc1cc(-c2nc(C(F)(F)F)cs2)c(-c2cnc3c(c2)c(=O)c(C(=O)O)cn3[C@H]2CCCN(CCN3CCOCC3)C2)cn1]

6-(3-ethylureido)-4-(4-(trifluoromethyl)thiazol-2-yl)pyridin-3-ylboronic acid (Intermediate 9, 0.350 g, 0.97 mmol)

and (S)-ethyl 6-bromo-1-(1-(2-morpholinoethyl)piperidin-3-yl)-4-oxo-1,4-dihydro-1,8-naphthyridine-3-carboxylate (Intermediate 34, 0.480 g, 0.97 mmol) were taken up in dioxane (4 mL), $Cs_2CO_3$ (0.633 g, 1.94 mmol) in water (1.000 mL) was added followed by $Pd(PPh_3)_4$ (0.112 g, 0.10 mmol). The reaction mixture was heated to 100° C. for 2 h, then 2 ml of 2N LiOH were added and stirred at 100° C. for an additional 30 min. The reaction mixture was cooled to room temperature and solvent evaporated. The resulting residue was taken back up in DMSO (2 ml) and filtered. DMSO solution was purified on an ISCO C18 column using water and acetonitrile. (S)-6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydro-1,8-naphthyridine-3-carboxylic acid (0.080 g, 12%) is recovered as a pale yellow solid.

MS (ES)(M+H)$^+$: 701 for $C_{32}H_{35}F_3N_8O_5S$.

$^1$H NMR δ ppm 9.80 (br. s., 1 H), 8.63 (s, 2 H), 8.55 (s, 1 H), 8.48 (s, 1 H), 8.36 (d, J=7.54 Hz, 2 H), 7.92 (br. s., 1 H), 5.42-5.62 (m, 1 H), 3.44-3.57 (m, 4 H), 3.20 (dd, J=13.19, 6.40 Hz, 3 H), 3.00 (br. s., 1 H), 2.87 (d, J=11.30 Hz, 1 H), 2.32-2.45 (m, 8 H), 2.15 (br.s., 1 H), 1.82 (d, J=10.55 Hz, 3 H), 1.67 (br. s., 1 H), 1.11 (t, J=7.16 Hz, 3 H).

Examples 32-35

The following Examples were prepared by the procedure described for Example 31 from the starting materials (SM) indicated.

| Ex | Compound | Data | SM |
|---|---|---|---|
| 32 | S)-1-((1-ethylpyrrolidin-2-yl)methyl)-6-(6-(3-ethylureido)-4-(4-(trifluoromethyl)thiazol-2-yl)pyridin-3-yl)-4-oxo-1,4-dihydro-1,8-naphthyridine-3-carboxylic acid | MS (ES) (M + H)$^+$: 616 for $C_{28}H_{28}F_3N_7O_4S$ $^1$H NMR δ ppm 10.10 (br. s., 1 H), 8.80 (s, 1 H), 8.65 (s, 1 H), 8.54 (s, 1 H), 8.48 (s, 1 H), 8.38 (d, J = 11.30 Hz, 2 H), 7.99 (br. s., 1 H), 4.38 (d, J = 5.27 Hz, 2 H), 3.15-3.25 (m, 3 H), 3.04-3.11 (m, 1 H) 2.89-2.98 (m, 1 H), 2.12-2.28 (m, 2 H), 1.58-1.79 (m, 3 H), 1.44-1.56 (m, 1 H), 1.11 (t, J = 7.16 Hz, 3 H), 0.90 (t, J = 7.16 Hz, 3 H). | Intermediate 31 and Intermediate 9 |
| 33 | R)-1-((1-ethylpyrrolidin-2-yl)methyl)-6-(6-(3-ethylureido)-4-(4-(trifluoromethyl)thiazol-2-yl)pyridin-3-yl)-4-oxo-1,4-dihydro-1,8-naphthyridine-3-carboxylic acid | MS (ES) (M + H)$^+$: 616 for $C_{28}H_{28}F_3N_7O_4S$ $^1$H NMR δ ppm 9.96-10.18 (m, 1 H), 8.66 (d, J = 18.08 Hz, 2 H), 8.44-8.57 (m, 2 H), 8.30-8.44 (m, 2 H), 8.03 (br. s., 1 H), 4.36 (d, J = 3.77 Hz, 2 H), 3.15-3.25 (m, 2 H), 3.02-3.13 (m, 1 H), 2.93 (d, J = 6.78 Hz, 1 H), 2.09-2.31 (m, 2 H), 1.58-1.83 (m, 2 H), 1.44-1.57 (m, 2 H), 1.11 (t, J = 7.16 Hz, 3 H), 0.91 (t, J = 7.16 Hz, 3 H). | Intermediate 32 and Intermediate 9 |

| Ex | Compound | Data | SM |
|---|---|---|---|
| 34 | (S)-1-(1-(2-(diethylamino)ethyl)piperidin-3-yl)-6-(6-(3-ethylureido)-4-(4-isobutylthiazol-2-yl)pyridin-3-yl)-4-oxo-1,4-dihydro-1,8-naphthyridine-3-carboxylic acid | MS (ES) (M + H)$^+$: 675 for $C_{35}H_{46}N_8O_4S$<br>$^1$H NMR δ ppm 9.46 (s, 1 H), 9.37 (br. s., 1 H), 8.93 (s, 1 H), 8.61 (s, 1 H), 8.37 (s, 1 H), 8.12 (s, 1 H), 7.58-7.70 (m, 1 H), 7.40 (s, 1 H), 5.69 (br. s., 1 H), 3.11-3.35 (m, 8 H), 2.73 (br. s., 3 H), 2.39 (d, J = 6.78 Hz, 3 H), 2.27 (br. s., 1 H), 2.04 (d, J = 3.77 Hz, 2 H), 1.80 (br. s., 2 H), 1.52 (ddd, J = 13.00, 6.78, 6.59 Hz, 1 H), 1.21 (t, J = 7.16 Hz, 6 H), 1.11 (t, J = 7.16 Hz, 3 H), 0.60 (d, J = 3.77 Hz, 6 H). | Intermediate 36 and Intermediate 46 |
| 35 | S)-1-(1-(2-(diethylamino)ethyl)piperidin-3-yl)-6-(6-(3-ethylureido)-4-(4-phenylthiazol-2-yl)pyridin-3-yl)-4-oxo-1,4-dihydro-1,8-naphthyridine-3-carboxylic acid | MS (ES) (M + H)$^+$: 695 for $C_{37}H_{42}N_8O_4S$<br>$^1$H NMR δ ppm 9.50 (s, 1 H), 9.38 (br. s., 1 H), 8.97 (s, 1 H), 8.83 (s, 1 H), 8.42 (s, 1 H), 8.16-8.35 (m, 2 H), 7.58 (d, J = 3.77 Hz, 3 H), 7.29 (d, J = 3.77 Hz, 3 H), 3.67 (br. s., 5 H), 3.01-3.30 (m, 8 H), 2.73 (br. s., 2 H), 2.28 (br. s., 1 H), 2.01 (br. s., 2 H), 1.76 (br. s., 2 H), 1.03-1.22 (m, 9 H). | Intermediate 36 and 1-(5-bromo-4-(4-phenylthiazol-2-yl)pyridin-2-yl)-3-ethylurea (WO2009106885) |

Examples 36-38

The following Examples were prepared by the procedure described for Example 31 from the starting materials (SM) indicated

| Ex | Compound | Data | SM |
|---|---|---|---|
| 36 | 7-(2-(dimethylamino)ethylamino)-1-(((S)-1-ethylpyrrolidin-2-yl)methyl)-6-(6-(3-ethylureido)-4-(4-(trifluoromethyl)thiazol-2-yl)pyridin-3-yl)-4-oxo-1,4-dihydro-1,8-naphthyridine-3-carboxylic acid | MS (ES) (M + H)$^+$: 702 for $C_{32}H_{38}F_3N_9O_4S$ $^1$H NMR δ ppm 9.48 (br. s., 1 H), 8.62-8.85 (m, 2 H), 8.49 (br. s., 1 H), 8.20-8.36 (m, 3 H), 8.09 (br. s., 1 H), 7.73 (br. s., 1 H), 4.15-4.63 (m, 2 H), 3.56 (br. s., 1 H), 3.16-3.27 (m, 3 H), 2.91-3.14 (m, 3 H), 2.08-2.29 (m, 3 H), 2.02 (d, J = 4.52 Hz, 6 H), 1.61-1.84 (m, 3 H), 1.52 (br. s., 1 H), 1.11 (t, J = 7.16 Hz, 3 H), 0.91 (t, J = 7.16 Hz, 3 H). | Intermediate 43 and Intermediate 9 |
| 37 | 7-(2-(dimethylamino)ethylamino)-1-ethyl-6-(6-(3-ethylureido)-4-(4-(trifluoromethyl)thiazol-2-yl)pyridin-3-yl)-4-oxo-1,4-dihydro-1,8-naphthyridine-3-carboxylic acid | MS (ES) (M + H)$^+$: 619 for $C_{27}H_{29}F_3N_8O_4S$ $^1$H NMR δ ppm 9.70 (br. s., 1 H), 9.51 (s, 1 H), 9.01 (s, 1 H), 8.48 (s, 1 H), 8.38 (s, 1 H), 8.26 (s, 1 H), 8.14 (s, 1 H), 7.67 (br. s., 1 H), 7.33 (t, J = 5.27 Hz, 1 H), 4.60 (d, J = 6.78 Hz, 1 H), 3.59-3.68 (m, 1 H), 3.38 (q, J = 7.03 Hz, 3 H), 3.16-3.29 (m, 2 H), 3.02 (dd, J = 11.68, 5.65 Hz, 2 H), 2.67-2.81 (m, 3 H), 1.44 (t, J = 7.16 Hz, 2 H), 1.00-1.17 (m, 6 H). | Intermediate 44 and Intermediate 9 |
| 38 | 1-ethyl-6-(6-(3-ethylureido)-4-(4-(trifluoromethyl)thiazol-2-yl)pyridin-3-yl)-7-(4-methylpiperazin-1-yl)-4-oxo-1,4-dihydro-1,8-naphthyridine-3-carboxylic acid | MS (ES) (M + H)$^+$: 631 for $C_{28}H_{29}F_3N_8O_4S$ $^1$H NMR δ ppm 9.60 (br. s., 1 H), 9.02 (br. s., 1 H), 8.48 (d, J = 8.29 Hz, 2 H), 8.31 (s, 1 H), 8.22 (s, 1 H), 7.66 (br. s., 1 H), 4.43-4.59 (m, 2 H), 2.93-3.25 (m, 6 H), 2.10-2.23 (m, 2 H), 2.04 (s, 3 H), 1.84-1.97 (m, 2 H), 1.33-1.46 (m, 3 H), 1.12 (t, J = 6.78 Hz, 3 H). | Intermediate 45 and Intermediate 9 |

Example 39

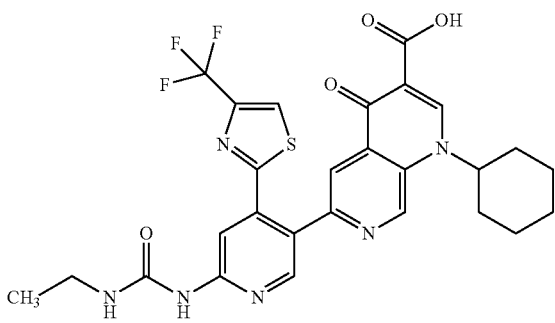 [SMILES: CCNC(=O)Nc1cc(-c2nc(C(F)(F)F)cs2)c(-c2cc3c(=O)c(C(=O)O)cn(C4CCCCC4)c3cn2)cn1]

To a solution of ethyl 6-bromo-1-cyclohexyl-4-oxo-1,4-dihydro-1,7-naphthyridine-3-carboxylate (Intermediate 47, 208 mg, 0.5 mmol, 1 equiv.) and 6-(3-ethylureido)-4-(4-(trifluoromethyl)thiazole-2-yl)pyridine-3-ylboronic acid (180 mg, 0.5 mmol, 1 equiv., WO2009106885) in 1,4-dioxane (3 mL) was added tetrakis(triphenylphosphino)palladium(0) (58 mg, 0.05 mmol, 0.1 equiv.) followed by a solution of cesium carbonate (326 mg, 1.0 mmol, 2 equiv.) in water (1 mL). This reaction mixture was stirred at 100° C. for 2 h. 2 M lithium hydroxide (0.5 mL) was added. The reaction mixture was stirred at 100° C. for 9 h, cooled to room temperature, and diluted with water. To this was added 1 N HCl was added until pH 3-4 was reached. The precipitate was collected by filtration, washed with water and hexanes and dried under high pressure. The compound was purified (HPLC) and concentrated to provide 1-cyclohexyl-6-(6-(3-ethylureido)-4-(4-(trifluoromethyl)thiazol-2-yl)pyridin-3-yl)-4-oxo-1,4-dihydro-1,7-naphthyridine-3-carboxylic acid as a solid (46.4 mg, 15%). Calcd for $C_{27}H_{25}F_3N_6O_4S$ $[M+H]^+$: 587.09.

NMR (d$_6$-DMSO) δ 9.61 (s, 1H), 9.54 (s, 1H), 8.96 (s, 1H), 8.53 (s, 1H), 8.52 (s, 1H), 8.28 (1, 1H), 8.17 (s, 1H), 7.68 (t, 1H), 4.99 (m, 1H), 4.26-4.17 (m, 2H), 2.08-2.05 (m, 2H), 1.92-1.82 (m, 4H), 1.72-1.60 (m, 3H), 1.38-1.33 (m, 1H), 1.1 (t, 3H).

Example 40-50

The following examples were prepared by the procedure described in Example 39 from the indicated starting material

| Ex | Compound | Data | SM |
|---|---|---|---|
| 40 | 1-(3,3-dimethylbutyl)-6-(6-(3-ethylureido)-4-(4-(trifluoromethyl)thiazol-2-yl)pyridin-3-yl)-4-oxo-1,4-dihydro-1,7-naphthyridin-3-carboxylic acid | Calcd for $C_{27}H_{27}F_3N_6O_4S$ $[M + H]^+$: 589.15. H$^1$NMR (d$_6$-DMSO) δ 13.79 (s, 1H), 9.57 (s, 1H), 9.23 (s, 1H), 9.09 (s, 1H), 8.57 (s, 1H), 8.56 (s, 1H), 8.27 (s, 1H), 8.15 (s, 1H), 7.61 (t, 1H), 4.7-4.63 (m, 2H), 3.26-3.17 (m, 2H), 1.76-1.7 (m, 2H), 1.12 (t, 3H), 1.01 (s, 9H) | Intermediate 48 & 6-(3-ethylureido)-4-(4-(trifluoromethyl)thiazole-2-yl)pyridine-3-ylboronic acid (WO2009106885) |
| 41 | (R)-1-((1-ethylpyrrolidin-2-yl)methyl)-6-(6-(3-ethylureido)-4-(4-(trifluoromethyl)thiazol-2-yl)pyridin-3-yl)-4-oxo-1,4-dihydro-1,7-naphthyridin-3-carboxylic acid | Calcd for $C_{28}H_{28}F_3N_7O_4S$ $[M + H]^+$: 616.17. H$^1$NMR (d$_6$-DMSO) δ 14.47 (s, 1H), 9.56 (s, 1H), 9.48 (s , 1H), 8.96 (s, 1H), 8.58 (d, 2H), 8.24 (s, 1H), 8.14 (s, 1H), 7.60 (t, 1H), 4.73-4.65 (m, 1H), 4.43-4.36 (m, 1H), 3.26-3.17 (m, 2H), 3.07-2.94 (m, 2H), 2.23-2.03 (m, 3H), 1.83-1.75 (m, 1H), 1.69-1.61 (m, 2H), 1.53-1.47 (m, 1H), 1.12 (t, 3H), 0.7 (t, 3H) | Intermediate 49 & 6-(3-ethylureido)-4-(4-(trifluoromethyl)thiazole-2-yl)pyridine-3-ylboronic acid (WO2009106885) |

-continued

| Ex | Compound | Data | SM |
|---|---|---|---|
| 42 | (S)-1-((1-ethylpyrrolidin-2-yl)methyl)-6-(6-(3-ethylureido)-4-(4-(trifluoromethyl)thiazol-2-yl)pyridin-3-yl)-4-oxo-1,4-dihydro-1,7-naphthyridin-3-carboxylic acid | Calcd for $C_{28}H_{28}F_3N_7O_4S$ [M + H]$^+$: 616.04. H$^1$NMR (d$_6$-DMSO) δ 14.48 (s, 1H), 9.55 (s, 1H), 9.45 (s, 1H), 8.94 (s, 1H), 8.57 (d, 2H), 8.23 (s, 1H), 8.14 (s, 1H), 7.62 (t, 1H), 4.72-4.65 (m, 1H), 4.41-4.34 (m, 1H), 3.26-3.17 (m, 2H), 3.07-2.94 (m, 2H), 2.25-2.08 (m, 3H), 1.90-1.83 (m, 1H), 1.71-1.63 (m, 2H), 1.50-1.46 (m, 1H), 1.12 (t, 3H), 0.7 (t, 3H) | Intermediate 50 & 6-(3-ethylureido)-4-(4-(trifluoromethyl)thiazole-2-yl)pyridine-3-ylboronic acid (WO2009106885) |
| 43 | 6-(6-(3-ethylureido)-4-(4-(trifluoromethyl)thiazol-2-yl)pyridin-3-yl)-1-(2-morpholinopropyl)-4-oxo-1,4-dihydro-1,7-naphthyridine-3-carboxylic acid | Calcd for $C_{28}H_{28}F_3N_7O_5S$ [M + H]$^+$: 632.02. H$^1$NMR (d$_6$-DMSO) δ 14.34 (s, 1H), 9.54 (s, 1H), 9.48 (s, 1H), 8.86 (s, 1H), 8.57 (d, 2H), 8.26 (s, 1H), 8.14 (s, 1H), 7.59 (t, 1H), 4.76-4.68 (m, 1H), 4.50-4.42 (m, 1H), 3.46-3.37 (m, 3H), 3.26-3.17 (m, 2H), 2.83-2.73 (m, 3H), 2.16-2.08 (m, 2H), 1.12 (t, 3H), 1.11 (t, 3H) | Intermediate 51 & 6-(3-ethylureido)-4-(4-(trifluoromethyl)thiazole-2-yl)pyridine-3-ylboronic acid (WO2009106885) |
| 44 | 1-(1,3-dimethoxypropan-2-yl)-6-(6-(3-ethylureido)-4-(4-(trifluoromethyl)thiazol-2-yl)pyridin-3-yl)-4-oxo-1,4-dihydro-1,7-naphthyridine-3-carboxylic acid | Calcd for $C_{26}H_{25}F_3N_6O_6S$ [M + H]$^+$: 607.03. H$^1$NMR (d$_6$-DMSO) δ 14.41 (s, 1H), 9.61 (s, 1H), 9.56 (s, 1H), 9.04 (s, 1H), 8.59 (s, 2H), 8.30 (s, 1H), 8.12 (s, 1H), 7.58 (t, 1H), 5.79-5.70 (m, 1H), 3.98-3.82 (m, 4H), 3.26-3.17 (m, 2H), 3.25 (s, 6H), 1.11 (t, 3H) | Intermediate 52 & 6-(3-ethylureido)-4-(4-(trifluoromethyl)thiazole-2-yl)pyridine-3-ylboronic acid (WO2009106885) |
| 45 | (S)-6-(6-(3-ethylureido)-4-(4-(trifluoromethyl)thiazol-2-yl)pyridin-3-yl)-1-(1-hydroxy-4-methylpentan-2-yl)-4-oxo-1,4-dihydro-1,7-naphthyridine-3-carboxylic acid | Calcd for $C_{27}H_{27}F_3N_6O_5S$ [M + H]$^+$: 605.22. H$^1$NMR (d$_6$-DMSO) δ 14.55 (s, 1H), 9.67 (s, 1H), 9.55 (s, 1H), 8.94 (s, 1H), 8.60 (s, 1H), 8.59 (d, 1H), 8.32 (s, 1H), 8.12 (s, 1H), 7.58 (t, 1H), 5.46-5.32 (m, 1H), 3.90-3.74 (m, 2H), 3.26-3.17 (m, 2H), 2.01-1.79 (m, 2H), 1.54-1.43 (m, 1H), 1.11 (t, 3H), 0.91 (d, 3H), 0.87 (d, 3H) | Intermediate 57 & 6-(3-ethylureido)-4-(4-(trifluoromethyl)thiazole-2-yl)pyridine-3-ylboronic acid (WO2009106885) |

| Ex | Compound | Data | SM |
|---|---|---|---|
| 46 | 6-(6-(3-ethylureido)-4-(4-(trifluoromethyl)thiazol-2-yl)pyridin-3-yl)-1-(2-methoxyethyl)-4-oxo-1,4-dihydro-1,7-naphthyridine-3-carboxylic acid | Calcd for $C_{24}H_{21}F_3N_6O_5S$ [M + H]$^+$: 563.11. H$^1$NMR (d$_6$-DMSO) δ 13.75 (s, 1H), 9.61 (s, 1H), 9.47 (s, 1H), 8.98 (s, 1H), 8.58 (s, 2H), 8.29 (s, 1H), 8.14 (s, 1H), 7.64 (t, 1H), 4.90-4.86 (m, 2H), 3.73-3.70 (m, 2H), 3.26-3.17 (m, 2H), 3.22 (s, 3H), 1.11 (t, 3H) | Intermediate 58 & 6-(3-ethylureido)-4-(4-(trifluoromethyl 2-yl)pyridine-3-ylboronic acid (WO2009106885) |
| 47 | 1-(2-(dimethylamino)ethyl)-6-(6-(3-ethylureido)-4-(4-(trifluoromethyl)thiazol-2-yl)pyridin-3-yl)-4-oxo-1,4-dihydro-1,7-naphthyridine-3-carboxylic acid | Calcd for $C_{25}H_{24}F_3N_7O_4S$ [M + H]$^+$: 576.14. H$^1$NMR (d$_6$-DMSO) δ 14.49 (s, 1H), 9.55 (s, 1H), 9.45 (s, 1H), 9.04 (s, 1H), 8.59 (s, 2H), 8.29 (s, 1H), 8.13 (s, 2H), 7.58 (t, 1H), 4.89-4.77 (m, 2H), 3.26-3.17 (m, 2H), 3.89-3.74 (m, 2H), 2.34 (s, 6H), 1.11 (t, 3H) | Intermediate 59 & 6-(3-ethylureido)-4-(4-(trifluoromethyl) thiazole-2-yl)pyridine-3-ylboronic acid (WO2009106885) |
| 48 | (S)-6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydro-1,7-naphthyridine-3-carboxylic acid | Calcd for $C_{32}H_{35}F_3N_8O_5S$ [M + H]$^+$: 701.32. H$^1$NMR (d$_6$-DMSO) 14.24 (s, 1H), 9.71 (s, 1H), 9.46 (s, 1H), 8.57 (s, 1H), 8.56 (s, 1H), 8.30 (s, 1H), 8.16 (s, 1H), 7.71 (t, 1H), 5.22-5.16 (m, 1H), 3.55-3.52 (m, 4H), 3.50-3.41 (m, 2H), 3.29-3.17 (m, 2H), 2.93-2.89 (m, 1H), 2.73-3.67 (m, 1H), 2.41-2.37 (m, 4H), 2.01-1.96 (m, 2H), 1.67-1.62 (m, 2H), 1.11 (t, 3H) | Intermediate 57 & 6-(3-ethylureido)-4-(4-(trifluoromethyl) thiazole-2-yl)pyridine-3-ylboronic acid (WO2009106885) |
| 49 | (R)-6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydro-1,7-naphthyridine-3-carboxylic acid | Calcd for $C_{32}H_{35}F_3N_8O_5S$ [M + H]$^+$: 701.22. H$^1$NMR (d$_6$-DMSO) δ 14.49 (s, 1H), 9.84 (s, 1H), 9.56 (s, 1H), 9.47 (s, 1H), 8.58 (s, 2H), 8.32 (s, 1H), 8.13 (s, 1H), 7.59 (t, 1H), 5.24-5.19 (m, 1H), 3.55-3.52 (m, 4H), 3.40-3.32 (m, 2H), 3.29-3.17 (m, 2H), 2.93-2.89 (m, 1H), 2.73-3.67 (m, 1H), 2.41-2.37 (m, 4H), 2.01-1.96 (m, 2H), 1.67-1.62 (m, 2H), 1.11 (t, 3H) | Intermediate 61 & 6-(3-ethylureido)-4-(4-(trifluoromethyl) thiazole-2-yl)pyridine-3-ylboronic acid (WO2009106885) |

| Ex | Compound | Data | SM |
|---|---|---|---|
| 50 | 6-(6-(3-ethylureido)-4-(4-(trifluoromethyl)thiazol-2-yl)pyridin-3-yl)-1-((1-methyl-1H-imidazol-4-yl)methyl)-4-oxo-1,4-dihydro-1,7-naphthyridine-3-carboxylic acid 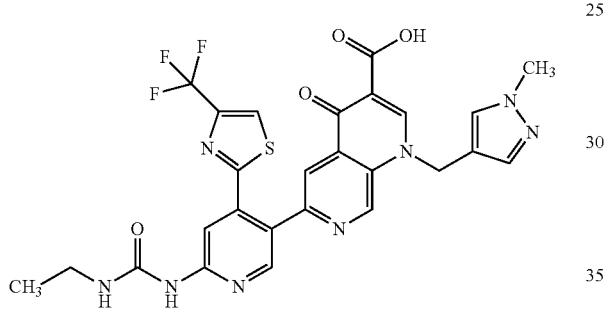 | Calcd for $C_{26}H_{21}F_3N_8O_4S$ $[M + H]^+$: 599.17. $H^1$NMR ($d_6$-DMSO) δ 14.31 (s, 1H), 9.53 (s, 1H), 9.5 (s, 1H), 9.27 (s, 1H), 8.57 (s, 1H), 8.56 (s, 1H), 8.37 (s, 1H), 8.26 (s, 1H), 8.13 (s, 1H), 7.62 (s, 1H), 7.56 (t, 1H), 5.92 (s, 2H), 3.7 (s, 3H), 3.25-3.16 (m, 2H), 1.11 (t, 3H) | Intermediate 53 & 6-(3-ethylureido)-4-(4-(trifluoromethyl)thiazole-2-yl)pyridine-3-ylboronic acid (WO2009106885) |

Example 51

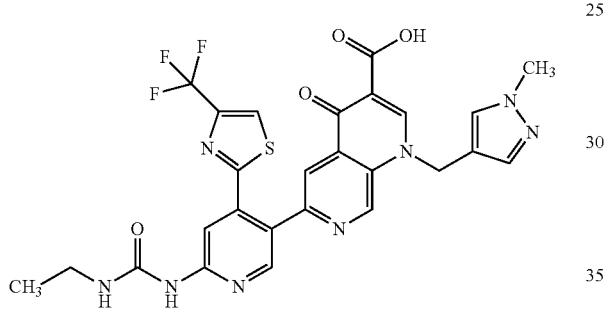

To a solution of palladium (II) acetate (22.95 mg, 0.10 mmol, 0.1 equiv.) and 1,1'-bis(di-t-butylphosphino)ferrocene (48.5 mg, 0.10 mmol, 0.1 equiv.) in acetonitrile (3 mL) was added ethyl 6-bromo-1-((1-methyl-1H-pyrazol-4-yl)methyl)-4-oxo-1,4-dihydro-1,7-naphthyridine-3-carboxylate (Intermediate 52, 400 mg, 1.02 mmol, 1 equiv.), followed by 6-(3-ethylureido)-4-(4-(trifluoromethyl)thiazol-2-yl)pyridine-3-ylboronic acid (WO2009106885, 372 mg, 1.03 mmol, 1.01 equiv.) and a solution of potassium carbonate (212 mg, 1.53 mmol, 1.5 equiv.) in water (1 mL). The reaction mixture was stirred at 60° C. for 9 h. The reaction mixture was concentrated under reduced pressure and resuspended in 1,4-dioxane (3 mL). 2 M Lithium Hydroxide (1.02 mL) was added, and the reaction mixture as stirred at 100° C. for 4 h. The reaction mixture was cooled to room temperature and diluted with water. 1 N HCl was added until pH 3-4 was reached. The precipitate was washed with water and hexanes and dried. The compound was purified (silica gel chromatography) and concentrated to provide 6-(6-(3-ethylureido)-4-(4-(trifluoromethyl)thiazol-2-yl)pyridin-3-yl)-1-((1-methyl-1H-pyrazol-4-yl)methyl)-4-oxo-1,4-dihydro-1,7-naphthyridine-3-carboxylic acid (90.7 mg, 15%). Calcd for $C_{26}H_{21}F_3N_8O_4S$ $[M+H]^+$: 599.16. $H^1$NMR ($d_6$-DMSO) δ 14.42 (s, 1H), 9.54 (s, 1H), 9.52 (s, 1H), 9.25 (s, 1H), 8.55 (s, 1H), 8.54 (s, 1H), 8.25 (s, 1H), 8.13 (s, 1H), 7.82 (s, 1H), 7.58 (t, 1H), 7.53 (s, 1H), 5.75 (s, 2H), 3.76 (s, 3H), 3.26-3.17 (m, 2H), 1.11 (t, 3H).

Example 52

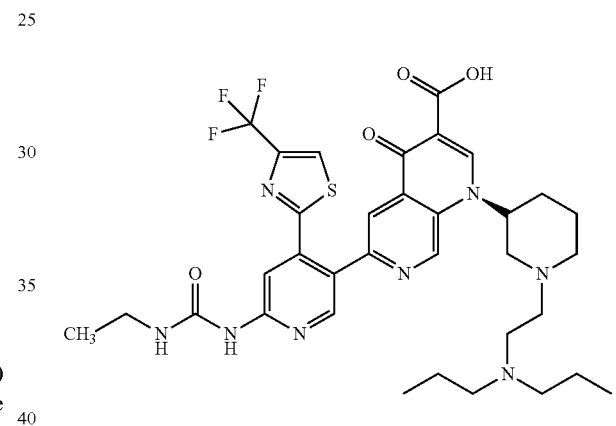

To a solution of (S)-ethyl 6-bromo-1-(1-(2-(diethylamino)ethyl)piperidin-3-yl)-4-oxo-1,4-dihydro-1,7-naphthyridine-3-carboxylate (Intermediate 63, 461 mg, 0.96 mmol, 1 equiv.) and 6-(3-ethylureido)-4-(4-(trifluoromethyl)thiazol-2-yl)pyridine-3-ylboronic acid (WO2009106885, 519 mg, 1.44 mmol, 1.5 equiv.) in 1,4-dioxane (4 mL) was added tetrakis(triphenylphosphino)palladium(0) (111 mg, 0.1 mmol, 0.1 equiv.) followed by a solution of cesium carbonate (627 mg, 1.92 mmol, 2.0 equiv.) in water (1.3 mL). This reaction mixture was stirred at 100° C. for 2 h. 2 M Lithium hydroxide (0.96 mL) was added. The reaction mixture was stirred at 100° C. for 9 h, cooled to room temperature, and diluted with water. 1 N HCl was added until pH 3-4 was reached. The precipitate was washed with water and hexanes and dried. The compound was purified (C18 silica gel chromatography) and concentrated to provide (S)-1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydro-1,7-naphthyridine-3-carboxylic acid as a solid (193 mg, 30%). Calcd for $C_{32}H_{37}F_3N_8O_4S$ $[M+H]^+$: 687.23.

$^1$NMR ($d_6$-DMSO) δ 14.08 (s, 1H), 9.87 (s, 1H), 9.54 (s, 1H), 9.46 (s, 1H), 8.57 (s, 2H), 8.31 (s, 1H), 8.14 (s, 1H), 7.58 (t, 1H), 5.20 (m, 1H), 3.26-3.17 (m, 2H), 2.91-2.88 (m, 1H), 2.75-2.69 (s, 1H), 2.66-2.63 (m, 2H), 1.98-1.96 (m, 2H), 1.65-1.60 (m, 2H), 1.12 (t, 3H), 0.95 (t, 3H).

Example 53

The following example was prepared by the procedure described in Example 52 from the indicated starting material.

| Ex | Compound | Data | SM |
|---|---|---|---|
| 53 | (R)-1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydro-1,7-naphthyridine-3-carboxylic acid | Calcd for $C_{32}H_{37}F_3N_8O_4S$ [M + H]$^+$: 687.20. H$^1$NMR (d$_6$-DMSO) δ 14.03 (s, 1H), 9.86 (s, 1H), 9.53 (s, 1H), 9.46 (s, 1H), 8.57 (s, 2H), 8.31 (s, 1H), 8.14 (s, 1H), 7.58 (t, 1H), 5.21 (m, 1H), 3.26-3.17 (m, 2H), 2.92-2.89 (m, 1H), 2.75-2.69 (s, 1H), 2.69-2.64 (m, 2H), 1.99-1.97 (m, 2H), 1.66-1.61 (m, 2H), 1.12 (t, 3H), 0.95 (t, 3H) | Intermediate 64 & 6-(3-ethylureido)-4-(4-(trifluoromethyl)thiazole-2-yl)pyridine-3-ylboronic acid (WO2009106885) |

Example 54-57

The following example was prepared by the procedure described in Example 16 from the indicated starting material.

| Ex | Compound | Data | SM |
|---|---|---|---|
| 54 | (R)-1-(1-(2-(diethylamino)ethyl)piperidin-3-yl)-6-(R)-1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydro-1,8-naphthyridine-3-carboxylic acid | Calcd for $C_{32}H_{37}F_3N_8O_4S$ [M + H]$^+$: 687 $^1$H NMR (d$_6$-DMSO) δ 9.49 (s, 2 H), 8.55 (s, 1 H), 8.37 (s, 2 H), 8.23 (s, 1 H), 8.17 (d, 1 H), 7.89 (d, 1 H), 7.59 (br. s., 1 H), 5.07 (br. s., 1 H), 3.56 (br. s., 7 H), 3.09-3.31 (m, 8 H), 2.92-3.11 (m, 1 H), 2.73 (br. s., 2 H), 2.06 (br. s., 2 H), 1.74 (br. s., 1 H), 1.22 (t, 6 H), 1.12 (t, 4 H). | Intermediate 67 |

-continued

| Ex | Compound | Data | SM |
|---|---|---|---|
| 55 | 1-(1,3-dimethoxypropan-2-yl)-6-(6-3-ethylureido)-4-(4-(trifluoromethyl) thiazol-2-yl)pyridin-3-yl)-4-oxo-1,4-dihydro-1,8-naphthyridine-3-carboxylic acid 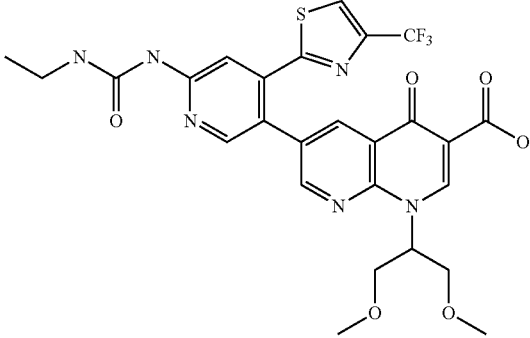 | Calcd for $C_{26}H_{25}F_3N_6O_6S$ $[M + H]^+$: 607 $^1$H NMR ($d_6$-DMSO) δ 14.53 (s, 1H), 9.54 (s, 1 H), 9.12 (s, 1 H), 8.93 (s, 1 H), 8.69 (s, 1 H), 8.59 (s, 1 H), 8.46 (s, 1H), 8.24 (s, 1 H), 7.54 (br. s., 1 H), 6.14 (br. s., 1 H), 3.91-4.05 (m, 2 H), 3.81 (dd, 4.14 Hz, 2 H), 3.17-3.28 (m, 8 H), 1.11 (t, 3 H). | Intermediate 73 |
| 56 | 6-(6-(3-ethylureido)-4-(4-(trifluoromethyl)thiazol-2-yl)pyridin-3-yl)-1-(2-morpholinoethyl)-4-oxo-1,4-dihydro-1,8-naphthyridine-3-carboxylic acid 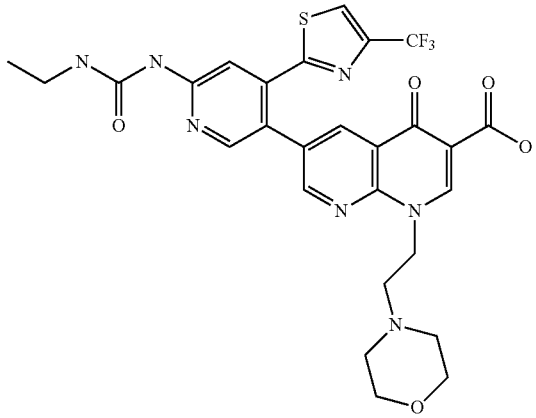 | Calcd for $C_{31}H_{36}F_3N_9O_5S$ $[M + H]^+$: 607 $^1$H NMR ($d_6$-DMSO) δ 9.55 (s, 1 H), 9.06 (br. s., 1 H), 8.86 (br. s., 1 H), 8.51-8.69 (m, 2 H), 8.43 (s, 1 H), 8.26 (s, 1 H), 7.53-7.68 (m, 1 H), 4.74 (br. s., 2 H), 3.50 (br. s., 4 H), 3.15-3.25 (m, 2 H), 2.63-2.74 (m, 2 H), 2.44 (br. s., 4 H), 1.12 (t, 3H). | Intermediate 72 |
| 57 | ethyl 6-(6-(3-ethylureido)-4-(4-(trifluoromethyl)thiazol-2-yl)pyridin-3-yl)-1-(1-methylazetidin-3-yl)-4-oxo-1,4-dihydro-1,8-naphthyridine-3-carboxylate 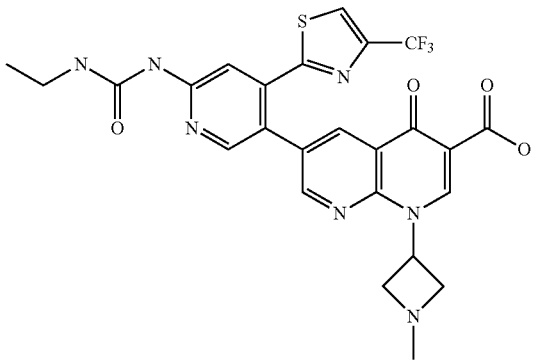 | Calcd for $C_{25}H_{22}F_3N_7O_4S$ $[M + H]^+$: 574 $^1$H NMR ($d_6$-DMSO) δ 9.55 (s, 1 H), 9.06 (br. s., 1 H), 8.86 (br. s., 1 H), 8.51-8.69 (m, 2 H), 8.43 (s, 1 H), 8.26 (s, 1 H), 7.53-7.68 (m, 1 H), 4.74 (br. s., 2 H), 3.50 (br. s., 4 H), 3.15-3.25 (m, 2 H), 2.63-2.74 (m, 2 H), 2.44 (br. s., 4 H), 1.12 (t, 3 H). | Intermediate 71 |

Example 58

The following example was prepared by the procedure described in Example 31 from the indicated starting material.

| 58 | (S)-1-((1-ethylpyrrolidin-2-yl)methyl)-6-(6-(3-ethylureido)-4-(4-(trifluoromethyl)thiazol-2-yl)pyridin-3-yl)-7-(4-methylpiperazin-1-yl)-4-oxo-1,4-dihydro-1,8-naphthyridine-3-carboxylic acid 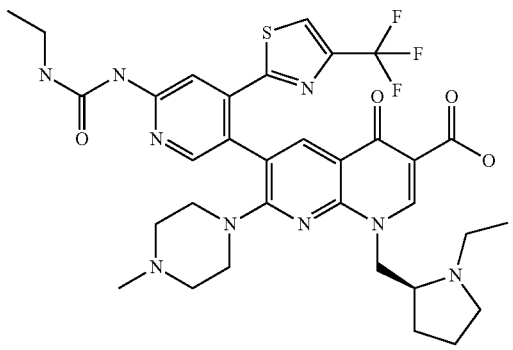 | Calcd for $C_{33}H_{38}F_3N_9O_4S$ <br> $[M + H]^+$: 714 <br> $^1H$ NMR ($d_6$-DMSO) δ 9.54 (s, 1 H), 9.20 (br. s., 1 H), 8.53-8.59 (m, 1 H), 8.48 (s, 1 H), 8.35-8.45 (m, 1 H), 8.22 (s, 1 H), 7.51 (br. s., 1 H), 4.87 (br. s., 2 H), 4.25 (s, 1 H), 3.99 (br. s., 2 H), 3.67 (br. s., 4 H), 3.29-3.59 (m, 5 H), 3.15-3.28 (m, 3 H), 3.00-3.13 (m, 1 H), 2.79-2.91 (m, 1 H), 2.73 (br. s., 3 H), 2.27 (s, 1 H), 2.01 (d, 2 H), 1.19 (d, 3 H), 1.12 (t, 3 H). | Intermediate 75 and Intermediate 9 |

Example 59

(S)-6-(6-(3-ethylureido)-4-(4-(trifluoromethyl)thiazol-2-yl)pyridin-3-yl)-1-(1-hydroxy-3,3-dimethylbutan-2-yl)-7-(4-methylpiperazin-1-yl)-4-oxo-1,4-dihydro-1,8-naphthyridine-3-carboxylic acid To a solution of (S)-ethyl 6-(6-(3-ethylureido)-4-(4-(trifluoromethyl)thiazol-2-yl)pyridin-3-yl)-7-fluoro-1-(1-hydroxy-3,3-dimethylbutan-2-yl)-4-oxo-1,4-dihydro-1,8-naphthyridine-3-carboxylate Intermediate 76 (200 mg, 0.31 mmol, 1 equiv.) in THF (1.2 mL) was added 1-methylpiperazine (0.041 mL, 0.37 mmol, 1.2 equiv.). This reaction was stirred at 50° C. for 10 h. 2 M lithium hydroxide (0.307 mL) was added. The reaction was stirred at 50° C. for 2 h, cooled to room temperature, and diluted with water. 10% wt. sol. of methanesulfonic acid was added until pH 5-6 was reached. The precipitate was discarded. The solution was partitioned

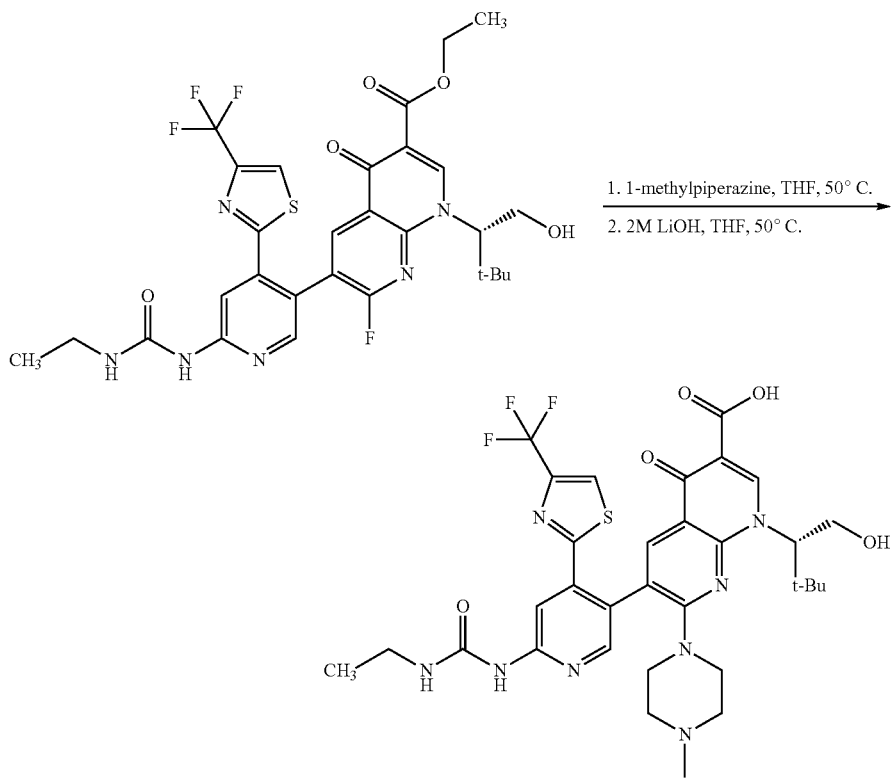

between water (10 mL) and ethyl acetate (10 mL). The aqueous layer was extracted with ethyl acetate (2×20 mL), and the aqueous layer was concentrated. The compound was purified (HPLC) and concentrated to provide (S)-6-(6-(3-ethylureido)-4-(4-(trifluoromethyl)thiazol-2-yl)pyridin-3-yl)-1-(1-hydroxy-3,3-dimethylbutan-2-yl)-7-(4-methylpiperazin-1-yl)-4-oxo-1,4-dihydro-1,8-naphthyridine-3-carboxylic acid as a solid (52.8 mg, 22%). Calcd for $C_{32}H_{37}F_3N_8O_5S$ [M+H]$^+$: 703.2. H$^1$NMR (d$_6$-DMSO) δ 15.18 (s, 1H), 9.51 (s, 1H), 8.8 (d, 1H), 8.51 (s, 1H), 8.48 (s, 1H), 8.36 (s, 1H), 8.2 (s, 1H), 7.6 (m, 1H), 5.71-5.68 (m, 1H), 5.09-5.02 (m, 1H), 4.09-4.0 (m, 2H), 3.29-3.27 (m, 2H), 3.21-3.19 (m, 2H), 3.15-3.04 (m, 2H), 2.18-2.14 (m, 2H), 2.05 (s, 3H), 1.95-1.91 (m, 2H), 1.12 (t, 3H), 0.95 (s, 9H).

Examples 60-61

The following examples were prepared by the procedure described in 59 from the indicated starting material.

| Ex | Compound | Data | SM |
| --- | --- | --- | --- |
| 60 | (S)-7-(3-(aminomethyl)pyrrolidin-1-yl)-6-(6-(3-ethylureido)-4-(4-(trifluoromethyl)thiazol-2-yl)pyridin-3-yl)-1-(2-(4-methylpiperazin-1-yl)ethyl)-4-oxo-1,4-dihydro-1,8-naphthyridine-3-carboxylic acid | Calcd for $C_{33}H_{39}F_3N_{10}O_4S$ [M + H]$^+$: 729.3. H$^1$NMR (d$_6$-DMSO) δ 15.39 (s, 1H), 9.47 (s, 1H), 8.89 (d, 1H), 8.55 (d, 1H), 8.45 (dd, 1H), 8.29 (dd, 1H), 8.11 (d, 1H), 7.71 (s, 2H), 7.54 (t, 1H), 4.65-4.58 (m, 2H), 3.43-3.39 (m, 2H), 3.26-3.17 (m, 4H), 3.10-3.04 (m, 4H), 2.89-2.72 (m, 5H) 2.72-2.65 (m, 4H), 1.93-1.74 (m, 2H), 1.12 (t, 3H). | Intermediate 77 and (R)-tert-butyl pyrrolidin-3-ylmethyl-carbamate |
| 61 | (S)-7-(3-(aminopyrrolidin-1-yl)-6-(6-(3-ethylureido)-4-(4-(trifluoromethyl)thiazol-2-yl)pyridin-3-yl)-1-(2-(4-methylpiperazin-1-yl)ethyl)-4-oxo-1,4-dihydro-1,8-naphthyridine-3-carboxylic acid | Calcd for $C_{32}H_{37}F_3N_{10}O_4S$ [M + H]$^+$: 715.4. H$^1$NMR (d$_6$-DMSO) 15.31 (s, 1H), 9.49 (s, 1H), 8.93 (d, 1H), 8.55 (d, 1H), 8.40 (d, 1H), 8.36 (d, 1H), 8.13 (s, 1H), 7.91 (s, 2H), 7.53 (t, 1H), 4.65-4.58 (m, 2H), 3.75-3.39 (m, 4H), 3.26-3.17 (m, 4H), 2.89-2.72 (m, 4H) 2.72-2.65 (m, 3H), 2.12-1.74 (m, 2H), 1.12 (t, 3H). | Intermediate 77 and (S)-tert-butyl pyrrolidin-3-ylcarbamate |

Example 62

(R)-1-(1-(2-(diethylamino)ethyl)piperidin-3-yl)-6-(6-(3-ethylureido)-4-(4-phenylthiazol-2-yl)pyridin-3-yl)-4-oxo-1,4-dihydro-1,7-naphthyridine-3-carboxylic acid

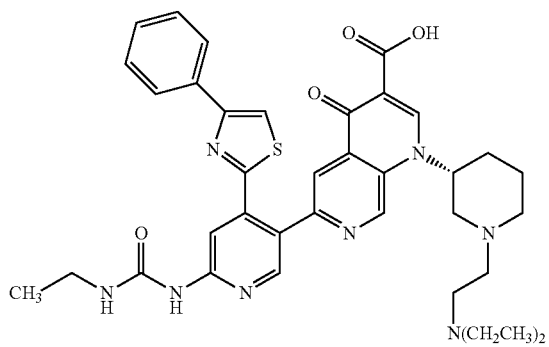

To a solution of 6-(3-ethylureido)-4-(4-phenylthiazol-2-yl)pyridine-3-ylboronic acid (WO2009106885) (624 mg, 1.69, 1 equiv.) and (R)-ethyl 6-bromo-1-(1-(2-(diethylamino)ethyl)piperidin-3-yl)-4-oxo-1,4-dihydro-1,7-naphthyridine-3-carboxylate Intermediate 65 (765 mg, 1.69 mmol, 1 equiv.) in 1,4-dioxane (7 mL) was added tetrakis(triphenylphosphino)palladium(0) (196 mg, 0.17 mmol, 0.1 equiv.) followed by a solution of cesium carbonate (828 mg, 2.54 mmol, 2.0 equiv.) in water (1.7 mL). This reaction mixture was stirred at 100° C. for 2 h. 2 M Lithium hydroxide (0.96 mL) was added. The reaction mixture was stirred at 100° C. for 9 h, cooled to room temperature, and diluted with water. 1 N HCl was added until pH 3-4 was reached, and the reaction was concentrated. The compound was purified (C18 silica gel chromatography) and concentrated to provide (R)-1-(1-(2-(diethylamino)ethyl)piperidin-3-yl)-6-(6-(3-ethylureido)-4-(4-phenylthiazol-2-yl)pyridin-3-yl)-4-oxo-1,4-dihydro-1,7-naphthyridine-3-carboxylic acid (422.1 mg, 36%). Calcd for $C_{37}H_{42}N_8O_4S$ $[M+H]^+$: 695.3.

$H^1$NMR ($d_6$-DMSO) δ 9.92 (s, 1H), 9.49 (s, 2H), 8.51 (s, 1H), 8.36 (s, 1H), 8.20 (s, 1H), 8.19 (s, 1H), 7.64 (t, 1H), 7.62-7.58 (m, 2H), 7.31-7.28 (m, 3H), 5.19 (m, 1H), 3.3-3.14 (m, 4H), 2.89-2.87 (m, 2H), 2.73-2.7 (m, 4H), 2.7-2.57 (m, 4H), 1.93-1.90 (m, 2H), 1.62-1.58 (m, 2H), 1.13 (t, 3H), 0.99 (t, 6H).

Examples 63-65

The following examples were prepared by the procedure described in Example 62 with the indicated starting material.

| Ex | Compound | Data | SM |
|---|---|---|---|
| 63 | (S)-6-(6-(3-ethylureido)-4-(4-phenylthiazol-2-yl)pyridin-3-yl)-1-(1-(2-morpholinoethyl)piperidin-3-yl)-4-oxo-1,4-dihydro-1,7-naphthyridine-3-carboxylic acid | Calcd for $C_{37}H_{40}N_8O_5S$ $[M + H]^+$: 709.3. $H^1$NMR ($d_6$-DMSO) δ 14.48 (s, 1H), 9.55 (s, 1H), 9.49 (s, 1H), 9.46 (s, 1H), 8.51 (s, 1H), 8.38 (s, 1H), 8.2 (s, 2H), 7.64 (t, 1H), 7.64-7.62 (m, 2H), 7.32-7.29 (m, 3H), 5.27 (m, 1H), 3.80-3.77 (m, 6H), 3.26-3.15 (m, 6H), 2.76-2.75 (m, 2H), 2.75-2.71 (m, 4H), 2.02-1.98 (m, 2H), 1.75-1.71 (m, 2H), 1.13 (t, 3H). | 6-(3-ethylureido)-4-(4-([phenyl]thiazole-2-yl)pyridine-3-ylboronic acid (WO2009106885) & Intermediate 60 |

-continued

| Ex | Compound | Data | SM |
|---|---|---|---|
| 64 | (R)-6-(6-(3-ethylureido)-4-(4-phenylthiazol-2-yl)pyridin-3-yl)-1-(1-(2-morpholinoethyl)piperidin-3-yl)-4-oxo-1,4-dihydro-1,7-naphthyridine-3-carboxylic acid | Calcd for $C_{37}H_{40}N_8O_5S$ [M + H]$^+$: 709.3. $H^1$NMR (d$_6$-DMSO) δ 9.84 (s, 1H), 9.5 (s, 1H), 9.48 (s, 1H), 8.51 (s, 1H), 8.36 (s, 1H), 8.21 (s, 1H), 8.2 (s, 1H), 8.19 (s, 1H), 7.67 (t, 1H), 7.65-7.57 (m, 2H), 7.29-7.27 (m, 3H), 5.18 (m, 1H), 3.99-3.96 (m, 2H), 3.78-3.75 (m, 2H), 3.53 (m, 2H), 3.28-3.19 (m, 2H), 3.2-3.17 (m, 2H), 2.9-2.73 (m, 2H), 2.73-2.68 (m, 2H), 2.47-2.44 (m, 2H), 2.38-2.34 (m, 2H), 1.92-1.89 (m, 2H), 1.60-1.57 (m, 2H), 1.13 (t, 3H). | 6-(3-ethylureido)-4-(4-([phenyl)thiazole-2-yl)pyridine-3-ylboronic acid (WO2009106885) & Intermediate 61 |
| 65 | 6-(6-(3-ethylureido)-4-(4-phenylthiazol-2-yl)pyridin-3-yl)-1-((1-methyl-1H-imidazol-4-yl)methyl)-4-oxo-1,4-dihydro-1,7-naphthyridine-3-carboxylic acid | Calcd for $C_{31}H_{26}N_8O_4S$ [M + H]$^+$: 607.2. $H^1$NMR (d$_6$-DMSO) δ 14.46 (s, 1H), 9.69 (s, 1H), 9.47 (s, 1H), 9.25 (s, 1H), 8.48 (s, 1H), 8.27 (s, 1H), 8.18 (s, 1H), 8.17 (s, 1H), 7.62 (t, 1H), 7.63-7.59 (m, 2H), 7.59 (s, 1H), 7.49-7.29 (m, 3H), 5.78 (s, 2H), 3.55 (s, 3H), 3.26-3.18 (s, 2H), 1.12 (t, 3H). | 6-(3-ethylureido)-4-(4-([phenyl)thiazole-2-yl)pyridine-3-ylboronic acid (WO2009106885) & Intermediate 53 |

Examples 66-75

The following examples were prepared by the procedure described in Example 39 with the indicated starting material.

| Ex | Compound | Data | SM |
|---|---|---|---|
| 66 | 1-tert-butyl-6-(6-(3-ethylureido)-4-(4-(trifluoromethyl)thiazol-2-yl)pyridin-3-yl)-4-oxo-1,4-dihydro-1,7-naphthyridine-3-carboxylic acid | Calcd for $C_{25}H_{23}F_3N_6O_4S$ [M + H]$^+$: 561. $H^1$NMR (d$_6$-DMSO) δ 9.68 (s, 1H), 9.59 (s, 1H), 9.08 (s, 1H), 8.58 (s, 1H), 8.56 (s, 1H), 8.34 (s, 1H), 8.18 (s, 1H), 7.62 (s, 1H), 3.26-3.17 (m, 2H), 1.88 (s, 9H), 1.12 (t, 3H). | Intermediate 9 & Intermediate 82 |

| Ex | Compound | Data | SM |
|---|---|---|---|
| 67 | 6-(6-(3-ethylureido)-4-(4-(trifluoromethyl)thiazol-2-yl)pyridin-3-yl)-4-oxo-1-(2-(pyrrolidin-1-yl)ethyl)-1,4-dihydro-1,7-naphthyridine-3-carboxylic acid | Calcd for $C_{27}H_{26}F_3N_7O_4S$ [M + H]$^+$: 602.23. H$^1$NMR (d$_6$-DMSO) δ 14.47 (s, 1H), 9.55 (s, 1H), 9.46 (s, 1H), 9.06 (s, 1H), 8.59 (s, 2H), 8.29 (s, 1H), 8.13 (s, 1H), 7.58 (t, 1H), 4.86 (m, 2H), 3.29-3.17 (m, 4H), 2.75-2.72 (m, 4H), 1.75-1.72 (m, 4H), 1.11 (t, 3H). | Intermediate 9 & Intermediate 83 |
| 68 | 1-ethyl-6-(6-(3-ethylureido)-4-(4-(trifluoromethyl)thiazol-2-yl)pyridin-3-yl)-4-oxo-1,4-dihydro-1,7-naphthyridine-3-carboxylic acid | Calcd for $C_{23}H_{19}F_3N_6O_4S$ [M + H]$^+$: 533.1. H$^1$NMR (d$_6$-DMSO) δ 14.53 (s, 1H), 9.58 (s, 1H), 9.44 (s, 1H), 9.11 (s, 1H), 8.57 (s, 2H), 8.29 (s, 1H), 8.14 (s, 1H), 7.61 (t, 1H), 4.71-4.68 (m, 2H), 3.26-3.17 (m, 2H), 1.43 (t, 3H), 1.11 (t, 3H). | Intermediate 9 & Intermediate 84 |
| 69 | 6-(6-(3-ethylureido)-4-(4-(trifluoromethyl)thiazol-2-yl)pyridin-3-yl)-1-(2-morpholinoethyl)-4-oxo-1,4-dihydro-1,7-naphthyridine-3-carboxylic acid | Calcd for $C_{27}H_{26}F_3N_7O_5S$ [M + H]$^+$: 618.15. H$^1$NMR (d$_6$-DMSO) δ 14.53 (s, 1H), 9.55 (s, 1H), 9.48 (s, 1H), 9.0 (s, 1H), 8.58 (s, 2H), 8.28 (s, 1H), 8.12 (s, 1H), 7.58 (t, 1H), 4.79 (m, 2H), 3.5-3.43 (m, 4H), 3.26-3.17 (m, 2H), 2.72-2.66 (m, 2H), 2.45-2.41 (m, 4H), 1.11 (t, 3H). | Intermediate 9 & Intermediate 85 |
| 70 | 6-(6-(3-ethylureido)-4-(4-(trifluoromethyl)thiazol-2-yl)pyridin-3-yl)-1-(1-methylazetidin-3-yl)-4-oxo-1,4-dihydro-1,7-naphthyridine-3-carboxylic acid | Calcd for $C_{25}H_{22}F_3N_7O_4S$ [M + H]$^+$: 574.07. H$^1$NMR (d$_6$-DMSO) δ 14.26 (s, 1H), 9.56 (s, 1H), 9.26 (s, 1H), 9.0 (s, 1H), 8.59 (s, 1H), 8.57 (s, 1H), 8.29 (s, 1H), 8.14 (s, 1H), 7.58 (s, 1H), 5.62-5.51 (m, 1H), 4.06-3.92 (m, 2H), 3.74-3.62 (m, 2H), 3.26-3.17 (m, 2H), 2.43 (s, 3H), 1.11 (t, 3H). | Intermediate 9 & Intermediate 91 |

-continued

| Ex | Compound | Data | SM |
|---|---|---|---|
| 71 | S)-6-(6-(3-ethylureido)-4-(4-(trifluoromethyl)thiazol-2-yl)pyridin-3-yl)-1-(1-hydroxy-3,3-dimethylbutan-2-yl)-4-oxo-1,4-dihydro-1,7-naphthyridine-3-carboxylic acid 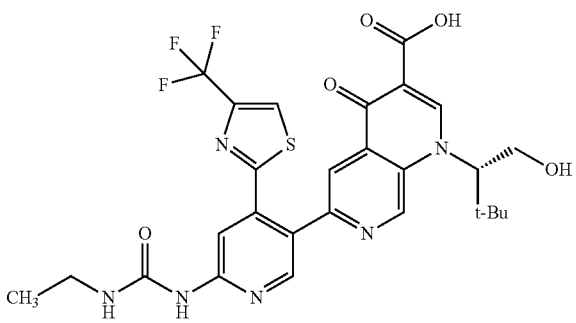 | Calcd for $C_{27}H_{27}F_3N_6O_5S$ $[M + H]^+$: 605.12. $H^1$NMR ($d_6$-DMSO) δ 14.14 (s, 1H), 9.77 (s, 1H), 9.6 (s, 1H), 8.9 (s, 1H), 8.58 (s, 2H), 8.32 (s, 1H), 8.13 (s, 1H), 7.63 (t, 1H), 5.3-5.2 (m, 2H), 4.15-4.02 (m, 2H), 3.26-3.17 (m, 2H), 1.11 (t, 3H), 0.98 (s, 9H). | Intermediate 9 & Intermediate 86 |
| 72 | 6-(6-(3-ethylureido)-4-(4-(trifluoromethyl)thiazol-2-yl)pyridin-3-yl)-4-oxo-1-(pyridin-4-ylmethyl)-1,4-dihydro-1,7-naphthyridine-3-carboxylic acid 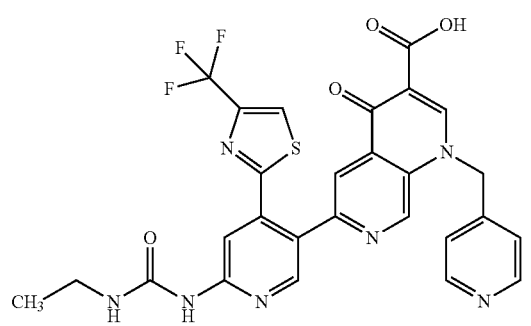 | Calcd for $C_{27}H_{20}F_3N_7O_4S$ $[M + H]^+$: 596.02. $H^1$NMR ($d_6$-DMSO) δ 14.36 (s, 1H), 9.54 (s, 1H), 9.34 (s, 1H), 9.1 (s, 1H), 8.54 (s, 2H), 8.53 (s, 1H), 8.52 (s, 1H), 8.3 (s, 1H), 8.1 (s, 1H), 7.56 (t, 1H), 7.27 (s, 1H), 7.25 (s, 1H), 6.03 (s, 2H), 3.25-3.16 (m, 2H), 1.1 (t, 3H). | Intermediate 9 & Intermediate 87 |
| 73 | (S)-6-(6-(3-ethylureido)-4-(4-(trifluoromethyl)thiazol-2-yl)pyridin-3-yl)-4-oxo-1-((1-propylpyrrolidin-3-yl)methyl)-1,4-dihydro-1,7-naphthyridine-3-carboxylic acid 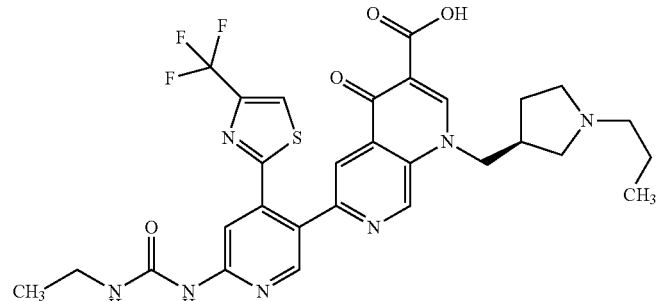 | Calcd for $C_{29}H_{30}F_3N_7O_4S$ $[M + H]^+$: 630.19. $H^1$NMR ($d_6$-DMSO) δ 8.53 (s, 1H), 9.5 (s, 1H), 9.1 (s, 1H), 8.58 (s, 1H), 8.29 (s, 1H), 8.17 (s, 1H), 8.13 (s, 1H), 7.57 (t, 3H), 4.67-4.64 (m, 1H), 3.26-3.17 (m, 2H), 2.72-2.62 (m, 4H), 2.36-2.26 (m, 4H), 1.87-1.84 (m, 1H), 1.51-1.46 (m, 1H), 1.44-1.36 (m, 2H), 1.12 (t, 3H), 0.85 (t, 3H). | Intermediate 9 & Intermediate 92 |

| Ex | Compound | Data | SM |
|---|---|---|---|
| 74 | (R)-1-((1-ethylpyrrolidin-3-yl)methyl)-6-(6-(3-ethylureido)-4-(4-(trifluoromethyl)thiazol-2-yl)pyridin-3-yl)-4-oxo-1,4-dihydro-1,7-naphthyridine-3-carboxylic acid | Calcd for $C_{28}H_{28}F_3N_7O_4S$ $[M + H]^+$: 616.16. $H^1$NMR ($d_6$-DMSO) δ 14.31 (s, 1H), 9.69 (s, 1H), 9.43 (s, 1H), 8.97 (s, 1H), 8.55 (s, 2H), 8.27 (s, 1H), 8.17 (s, 1H), 7.72 (t, 1H), 4.70-4.67 (m, 1H), 4.59-4.57 (m, 2H), 3.26-3.17 (m, 2H), 2.73-2.62 (m, 2H), 2.46-2.23 (m, 2H), 1.87-1.79 (m, 2H), 1.51-1.47 (m, 1H), 1.26-1.23 (m, 1H), 1.12 (t, 3H), 0.97 (t, 3H). | Intermediate 9 & Intermediate 93 |
| 75 | 1-cyclopropyl-6-(6-(3-ethylureido)-4-(4-(1-methyl-1H-pyrazol-4-yl)thiazol-2-yl)pyridin-3-yl)-4-oxo-1,4-dihydro-1,7-naphthyridine-3-carboxylic acid | Calcd for $C_{27}H_{24}N_8O_4S$ $[M + H]^+$: 557.1. $H^1$NMR ($d_6$-DMSO) δ 9.69 (s, 1H), 9.55 (s, 1H), 8.81 (s, 1H), 8.38 (s, 1H), 8.18 (s, 2H), 7.87 (s, 2H), 7.66 (s, 1H), 7.56 (s, 1H), 3.7-3.65 (m, 1H), 3.26-3.17 (m, 2H), 3.21 (s, 3H), 1.31-1.25 (m, 2H), 1.11 (t, 3H), 0.99 (m, 2H). | Intermediate 98 & Intermediate 88 |

Example 76

6-(6-(3-ethylureido)-4-(4-(1-methyl-1H-pyrazol-4-yl)thiazol-2-yl)pyridin-3-yl)-1-((1-methyl-1H-imidazol-4-yl)methyl)-4-oxo-1,4-dihydro-1,7-naphthyridine-3-carboxylic acid

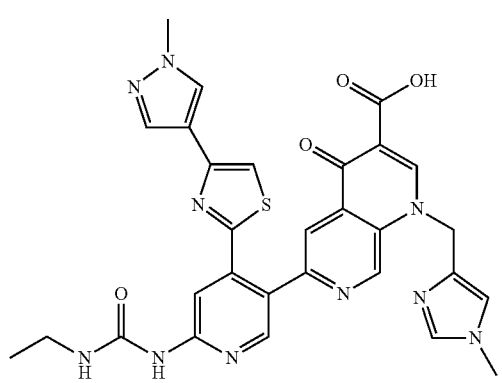 [SMILES: CCNC(=O)Nc1cc(-c2nc(-c3cnn(C)c3)cs2)c(-c2cc3c(=O)c(C(=O)O)cn(Cc4cn(C)cn4)c3cn2)cn1]

2N LiOH (1 mL) was added to a mixture of ethyl 6-(6-(3-ethylureido)-4-(4-(1-methyl-1H-pyrazol-4-yl)thiazol-2-yl)pyridin-3-yl)-1-((1-methyl-1H-imidazol-4-yl)methyl)-4-oxo-1,4-dihydro-1,7-naphthyridine-3-carboxylate, 86.3 mg, 0.14 mmol) in MeOH (imp and THF (1 mL). The resulting solution was stirred at room temperature for two hours. The solvent was removed and the residue was diluted with water and acidified with 1N HCl. The precipitated product was collected by filtration and washed with water and dried (60 mg).

LC/MS (ES$^+$)[(M+H)$^+$]: 611 for $C_{29}H_{26}N_{10}O_4S$. $^1$H NMR (300 MHz, $d_6$-DMSO): 1.12 (t, 3H), 3.22 (m, 2H), 3.58 (s, 3H), 3.8 (s, 3H), 5.77 (s, 2H), 7.35 (s, 1H), 7.5 (s, 1H), 7.6 (s, 1H), 7.62 (m, 1H), 7.72 (s, 1H), 7.84 (s, 1H), 8.12 (s, 1H), 8.25 (s, 1H), 8.46 (s, 1H), 9.23 (s, 1H), 9.46 (s, 1H), 9.86 (s, 1H), 14.46 (s, 1H).

Example 77

The following Example was prepared in accordance to the procedure described for example 76 using the starting materials indicated in the table.

| Ex | Compound | Data | SM |
|---|---|---|---|
| 77 | 7-(3-aminopyrrolidin-1-yl)-1-ethyl-6-(6-(3-ethylureido)-4-(4-(trifluoromethyl)thiazol-2-yl)pyridin-3-yl)-4-oxo-1,4-dihydro-1,8-naphthyridine-3-carboxylic acid 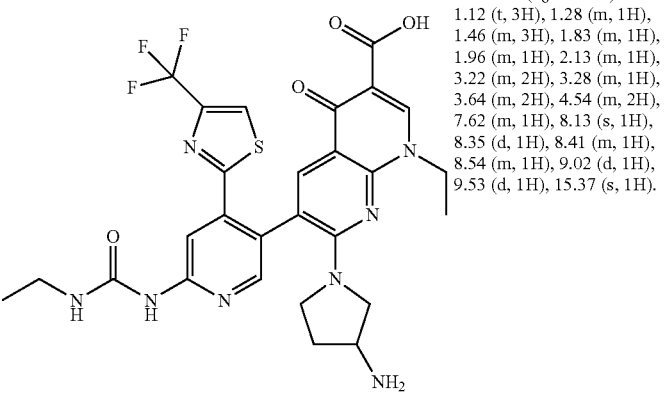 | Calcd for $C_{27}H_{27}F_3N_8O_4S$ $[M + H]^+$: 617 $^1$H NMR (d$_6$-DMSO): δ 1.12 (t, 3H), 1.28 (m, 1H), 1.46 (m, 3H), 1.83 (m, 1H), 1.96 (m, 1H), 2.13 (m, 1H), 3.22 (m, 2H), 3.28 (m, 1H), 3.64 (m, 2H), 4.54 (m, 2H), 7.62 (m, 1H), 8.13 (s, 1H), 8.35 (d, 1H), 8.41 (m, 1H), 8.54 (m, 1H), 9.02 (d, 1H), 9.53 (d, 1H), 15.37 (s, 1H). | Intermediate 101 LiOH, HCl |

Example 78

7-(3-aminopyrrolidin-1-yl)-6-(6-(3-ethylureido)-4-(4-(trifluoromethyl)thiazol-2-yl)pyridin-3-yl)-1-((S)-1-hydroxy-3,3-dimethylbutan-2-yl)-4-oxo-1,4-dihydro-1,8-naphthyridine-3-carboxylic acid

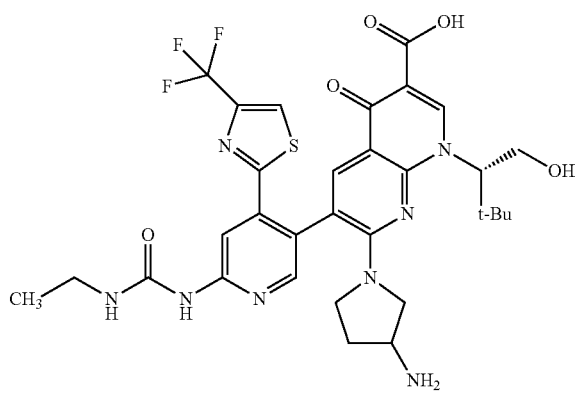 [SMILES: CCNC(=O)Nc1cc(-c2nc(C(F)(F)F)cs2)c(-c2cc3c(=O)c(C(=O)O)cn([C@H](CO)C(C)(C)C)c3nc2N2CCC(N)C2)cn1]

To a solution of 7-(3-(tert-butoxycarbonylamino)pyrrolidin-1-yl)-6-(6-(3-ethylureido)-4-(4-(trifluoromethyl)thiazol-2-yl)pyridin-3-yl)-1-((S)-1-hydroxy-3,3-dimethylbutan-2-yl)-4-oxo-1,4-dihydro-1,8-naphthyridine-3-carboxylic acid (Intermediate 105) (290 mg, 0.37 mmol, 1 equiv.) in dichloromethane (2 mL) was added methanesulfonic acid (0.048 mL, 0.73 mmol, 2 equiv.). The reaction was stirred at 23° C. for 2 h. The reaction was concentrated and re-suspended in water. The precipitate was discarded, and the filtrate was concentrated. The compound was purified via C18 silica gel chromatography and concentrated to afford 7-(3-aminopyrrolidin-1-yl)-6-(6-(3-ethylureido)-4-(4-(trifluoromethyl)thiazol-2-yl)pyridin-3-yl)-1-((S)-1-hydroxy-3,3-dimethylbutan-2-yl)-4-oxo-1,4-dihydro-1,8-naphthyridine-3-carboxylic acid (28.7 mg, 11%).

Calcd for $C_{31}H_{35}F_3N_8O_5S$ [M+H]$^+$: 689.2. H$^1$NMR (d$_6$-DMSO) δ 9.48 (s, 1H), 8.74 (d, 1H), 8.54 (s, 1H), 8.44 (s, 1H), 8.24 (s, 1H), 8.15 (s, 1H), 8.14 (s, 1H), 7.58 (s, 1H), 5.78-5.74 (m, 1H), 5.07-5.03 (m, 1H), 4.08-4.01 (m, 2H), 3.48-3.24 (m, 2H), 3.22-3.117 (m, 2H), 2.28-2.25 (m, 1H), 1.95-1.91 (m, 1H), 1.65-1.54 (m, 2H), 1.12 (t, 3H), 0.98 (s, 9H).

The following compounds were prepared in a similar manner to those described above using the appropriate starting materials and reaction conditions; in certain cases, with minor modification of the experimentals described above within the scope of the ordinarily skilled artisan (i.e., in light of the description/experimental provided herein). Moreover, the compounds in the table below were tested in an assay substantially similar to the assay described above for measuring the inhibition of S. aureus GyrB ATPase and were found to have a percent inhibition of S. aureus GyrB ATPase of similar magnitude to those compounds shown above.

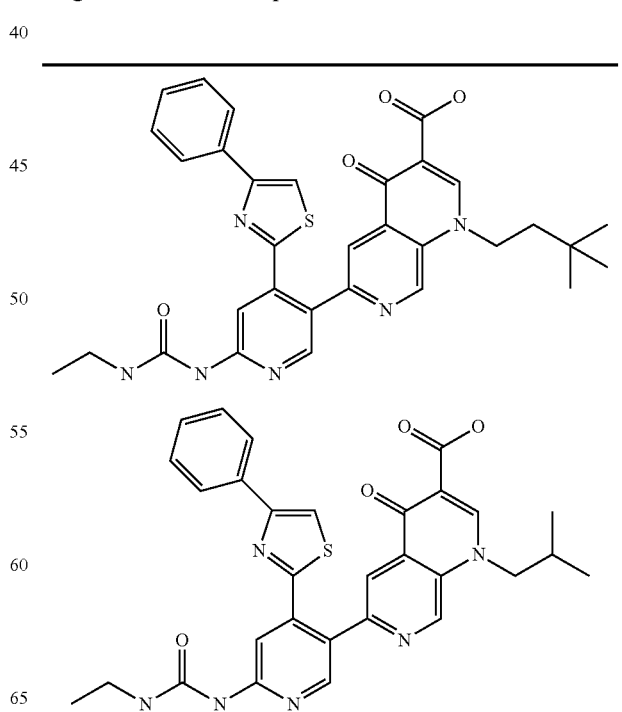

-continued
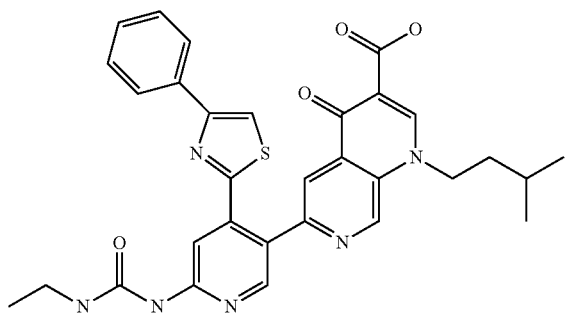 [SMILES: CCNC(=O)Nc1cc(-c2nc(-c3ccccc3)cs2)c(-c2cc3c(=O)c(C(=O)O)cn(CCC(C)C)c3cn2)cn1]
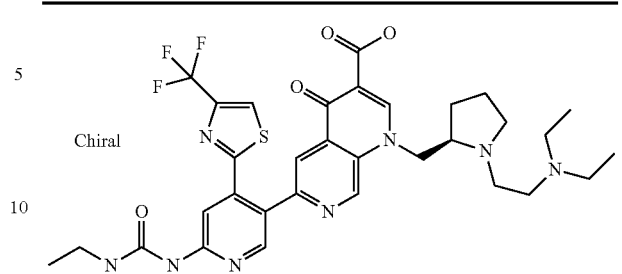
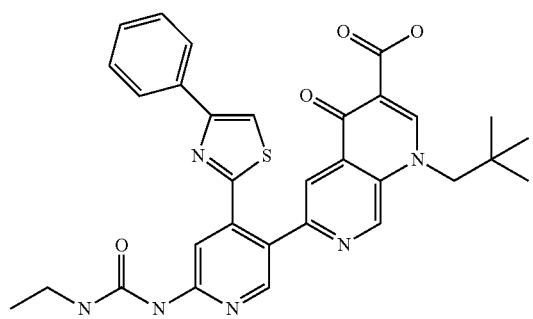 [SMILES: CCNC(=O)Nc1cc(-c2nc(-c3ccccc3)cs2)c(-c2cc3c(=O)c(C(=O)O)cn(CC(C)(C)C)c3cn2)cn1]
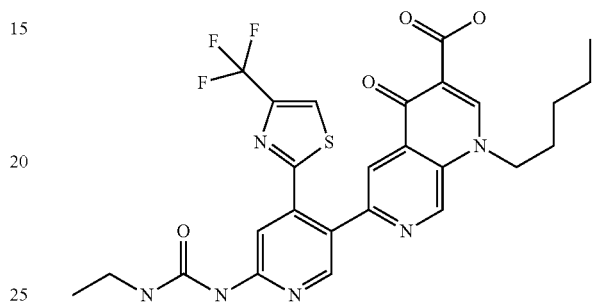
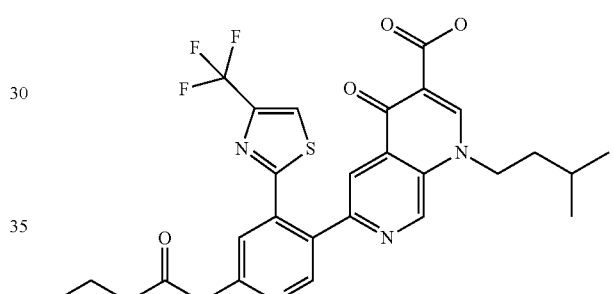
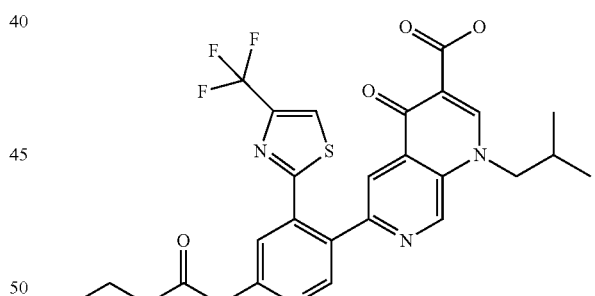
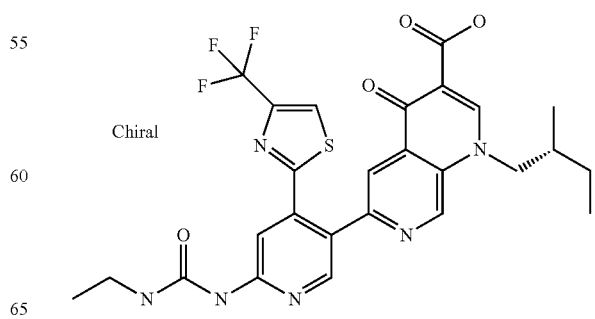

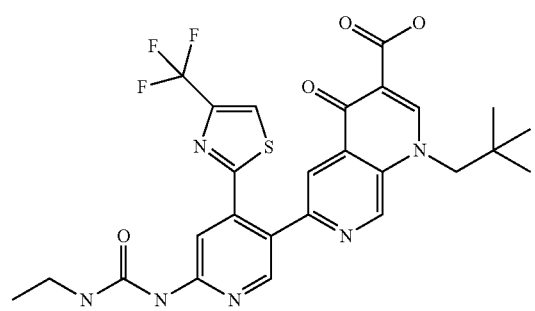 [SMILES: CCNC(=O)Nc1cc(-c2nc(C(F)(F)F)cs2)c(-c2cc3c(=O)c(C(=O)O)cn(CC(C)(C)C)c3cn2)cn1]

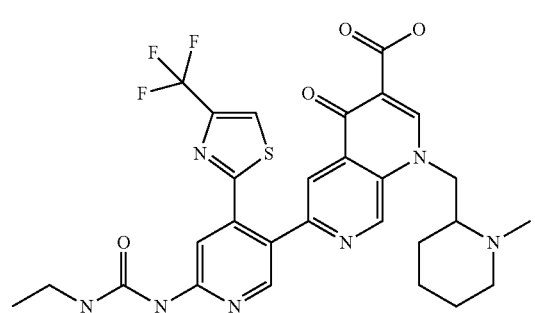 [SMILES: CCNC(=O)Nc1cc(-c2nc(C(F)(F)F)cs2)c(-c2cc3c(=O)c(C(=O)O)cn(CC4CCCCN4C)c3cn2)cn1]

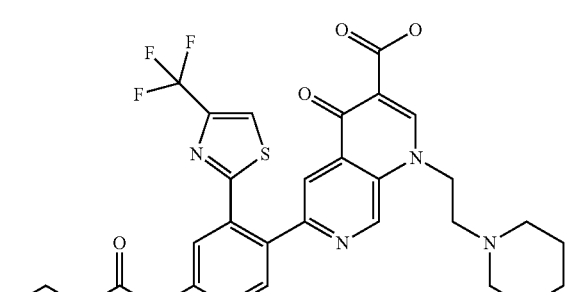

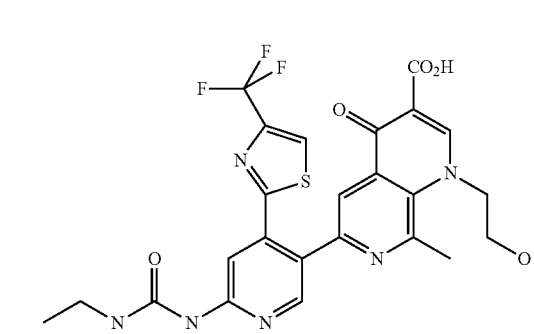 [SMILES: CCNC(=O)Nc1cc(-c2nc(C(F)(F)F)cs2)c(-c2cc3c(=O)c(C(=O)O)cn(CCO)c3c(C)n2)cn1]

Chiral

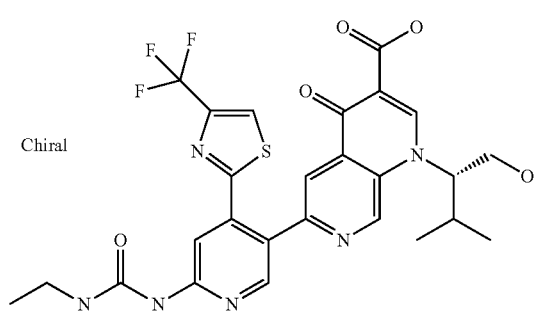 [SMILES: CCNC(=O)Nc1cc(-c2nc(C(F)(F)F)cs2)c(-c2cc3c(=O)c(C(=O)O)cn([C@H](CO)C(C)C)c3cn2)cn1]

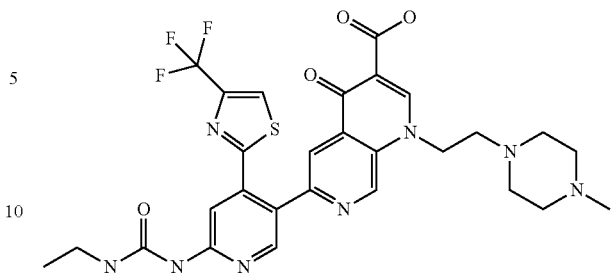

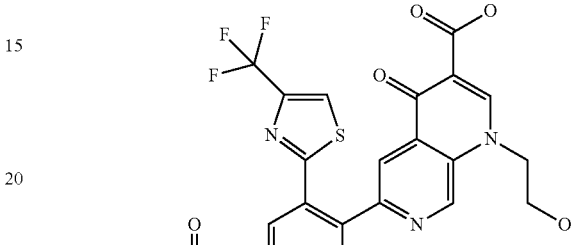

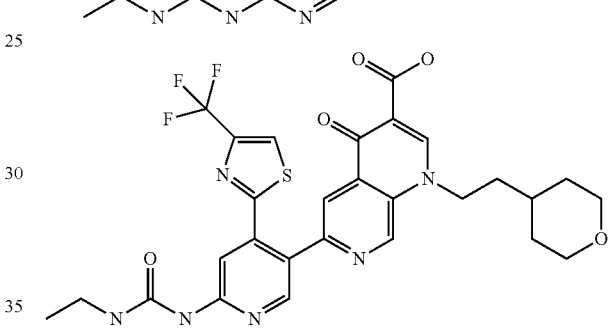

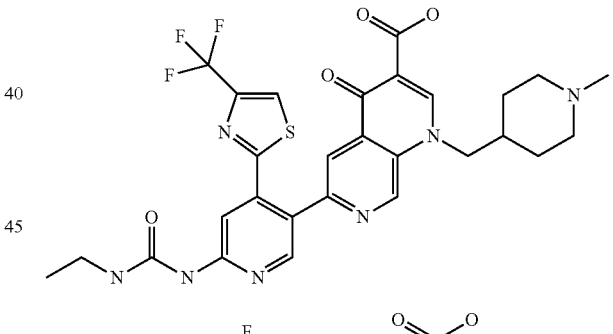

The following compounds were prepared in a similar manner to those described above using the appropriate starting materials and reaction conditions; in certain cases, with minor modification of the experimentals described above within the scope of the ordinarily skilled artisan (i.e., in light of the description/experimental provided herein). Moreover, the compounds in the table below were tested in an assay substantially similar to the assay described above for measuring the inhibition of *S. aureus* GyrB ATPase and were found to have a percent inhibition of *S. aureus* GyrB ATPase of similar magnitude to those compounds shown above.
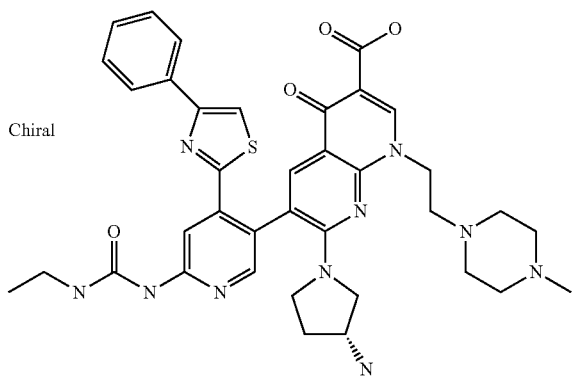 [SMILES: CCNC(=O)Nc1cc(-c2nc(-c3ccccc3)cs2)c(-c2cc3c(=O)c(C(=O)O)cn(CCN4CCN(C)CC4)c3nc2N2CC[C@@H](N)C2)cn1]
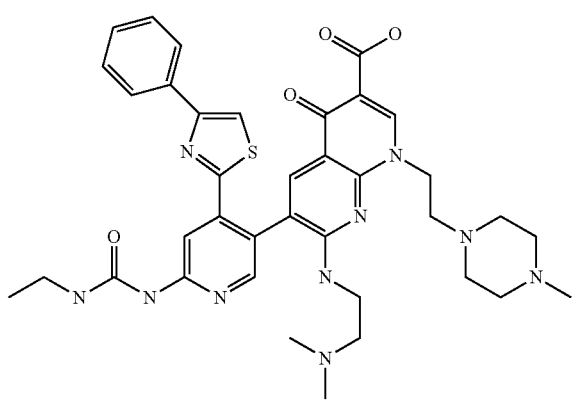 [SMILES: CCNC(=O)Nc1cc(-c2nc(-c3ccccc3)cs2)c(-c2cc3c(=O)c(C(=O)O)cn(CCN4CCN(C)CC4)c3nc2NCCN(C)C)cn1]
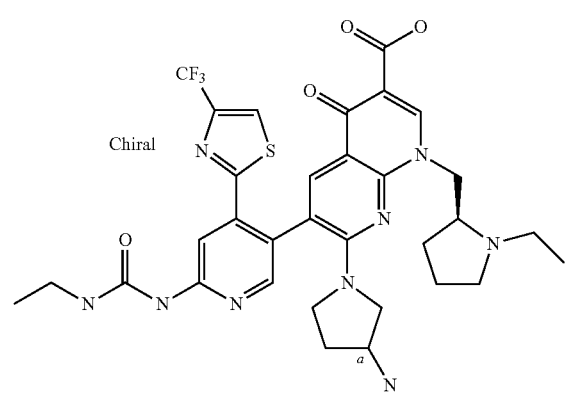
a = 1:1
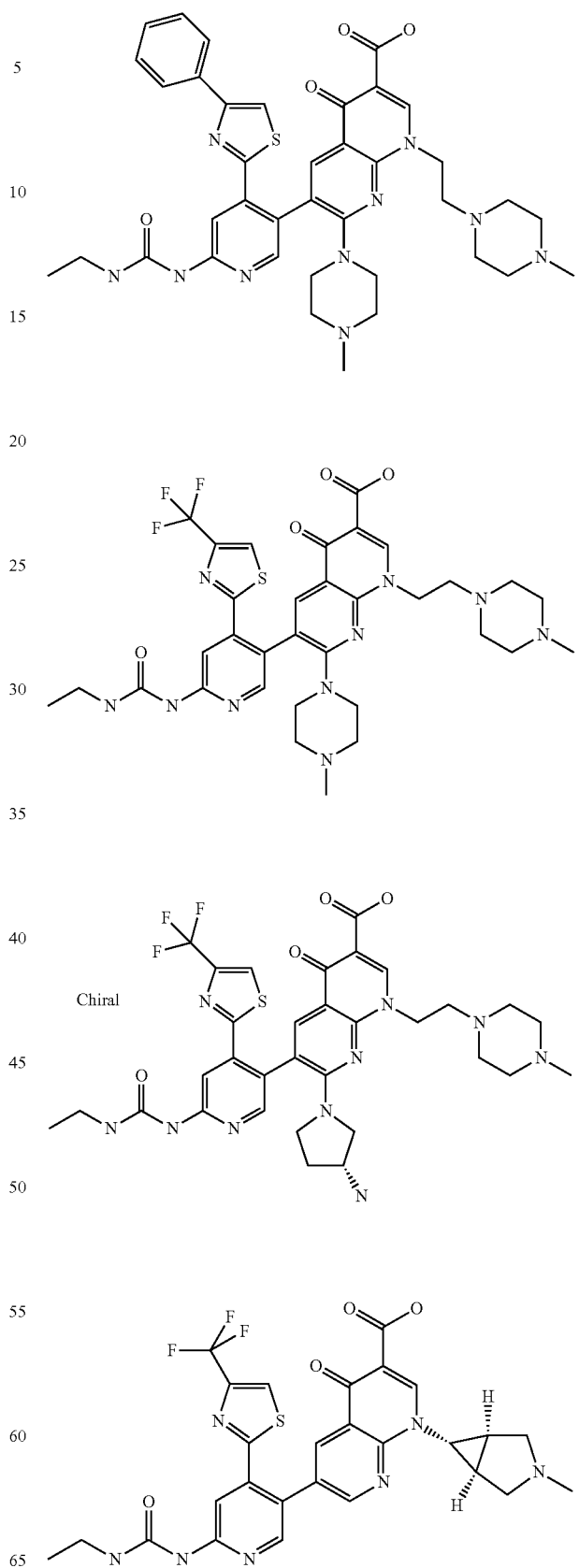

101
-continued
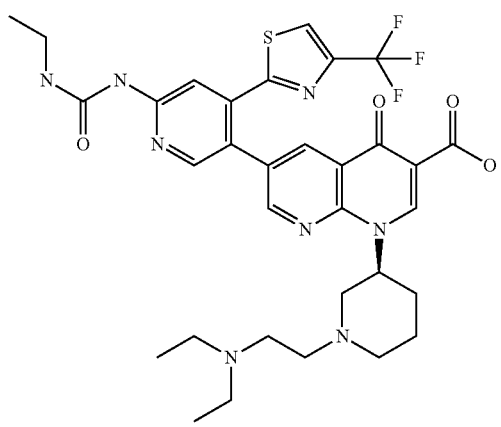
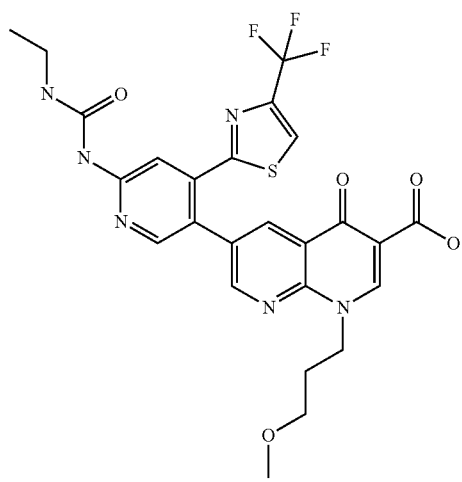 [SMILES: CCNC(=O)Nc1cc(-c2nc(C(F)(F)F)cs2)c(-c2cnc3c(c2)c(=O)c(C(=O)O)cn3CCCOC)cn1]
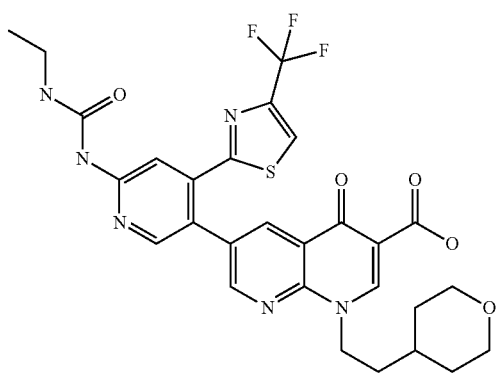 [SMILES: CCNC(=O)Nc1cc(-c2nc(C(F)(F)F)cs2)c(-c2cnc3c(c2)c(=O)c(C(=O)O)cn3CCC2CCOCC2)cn1]
102
-continued
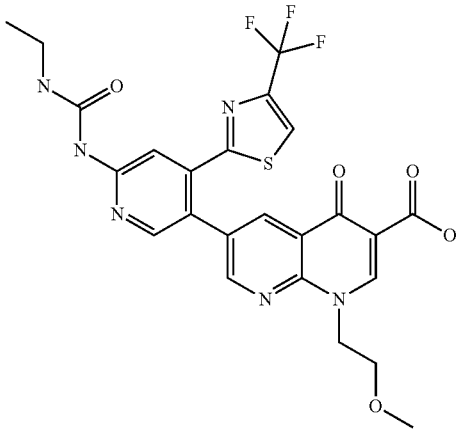 [SMILES: CCNC(=O)Nc1cc(-c2nc(C(F)(F)F)cs2)c(-c2cnc3c(c2)c(=O)c(C(=O)O)cn3CCOC)cn1]
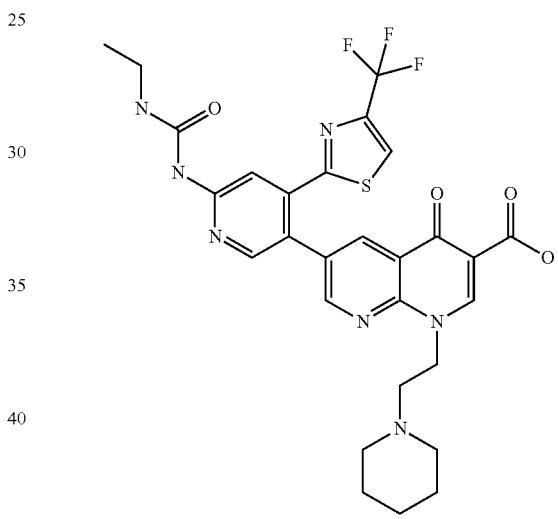
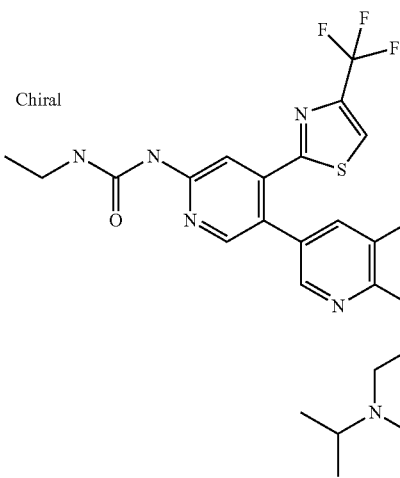

103
-continued
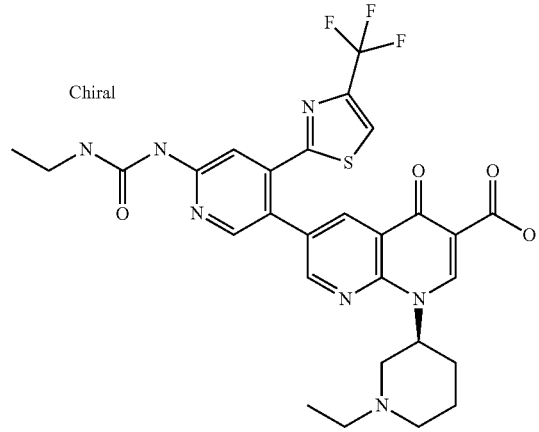 [SMILES: CCNC(=O)Nc1cc(-c2nc(C(F)(F)F)cs2)c(-c2cnc3c(c2)c(=O)c(C(=O)O)cn3[C@H]2CCCN(CC)C2)cn1]
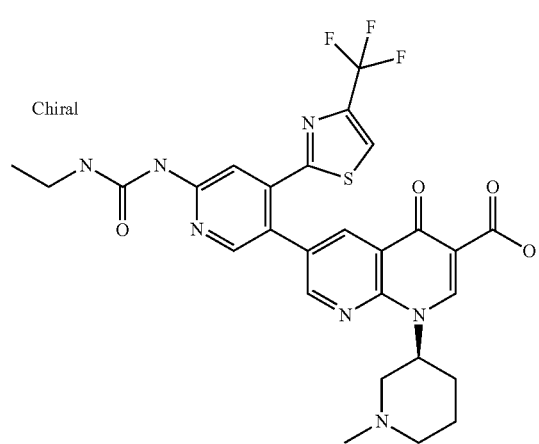 [SMILES: CCNC(=O)Nc1cc(-c2nc(C(F)(F)F)cs2)c(-c2cnc3c(c2)c(=O)c(C(=O)O)cn3[C@H]2CCCN(C)C2)cn1]
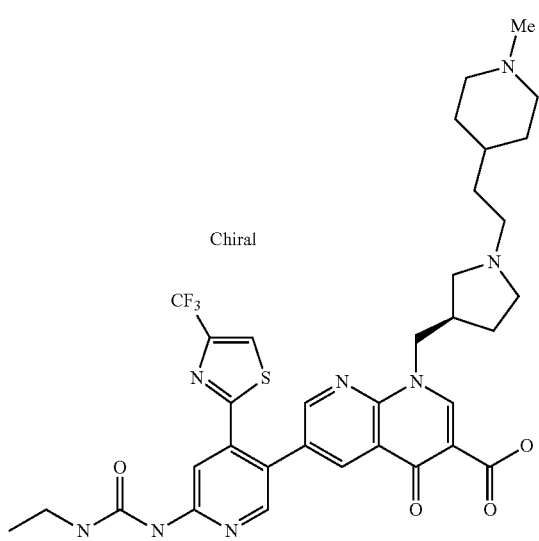 [SMILES: CCNC(=O)Nc1cc(-c2nc(C(F)(F)F)cs2)c(-c2cnc3c(c2)c(=O)c(C(=O)O)cn3C[C@@H]2CCN(CCC3CCN(C)CC3)C2)cn1]
104
-continued
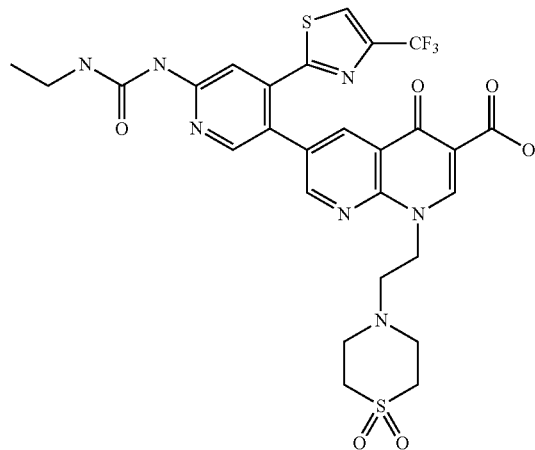 [SMILES: CCNC(=O)Nc1cc(-c2nc(C(F)(F)F)cs2)c(-c2cnc3c(c2)c(=O)c(C(=O)O)cn3CCN2CCS(=O)(=O)CC2)cn1]
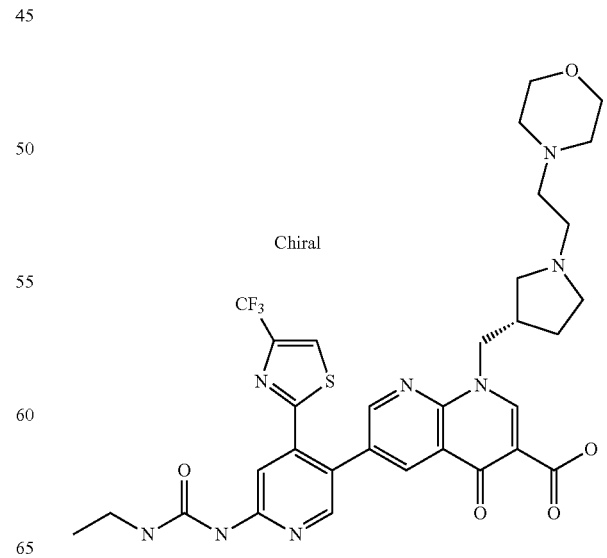

Intermediate 1

6-bromo-1-((1-methylpiperidin-4-yl)methyl)-4-oxo-1,4-dihydro-1,8-naphthyridine-3-carboxylate

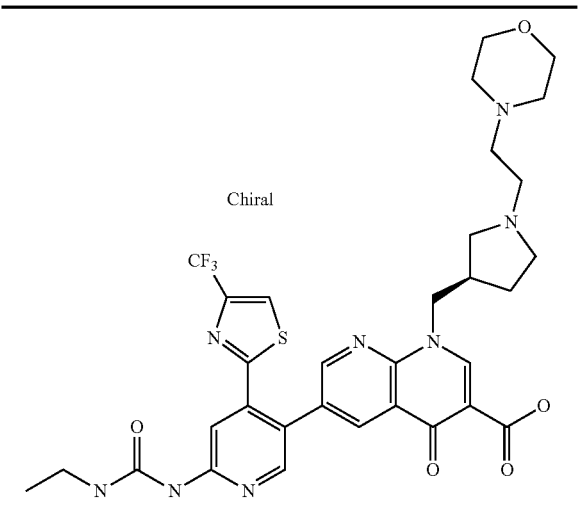

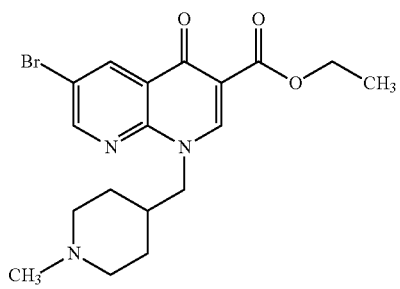 [SMILES: CCOC(=O)c1cn(CC2CCN(C)CC2)c2ncc(Br)cc2c1=O]

To a solution of ethyl 2-(5-bromo-2-fluoronicotinoyl)-3-(dimethylamino)acrylate (Intermediate 3, 784 mg, 2.27 mmol) dissolved in THF (12 mL) was added (1-methylpiperidin-4-yl)methanamine (291 mg, 2.27 mmol). The reaction mixture was stirred at 60° C. for 2 h, then cooled to room temperature, concentrated under reduced pressure, and the resulting residue was resuspended in DMF (12 mL). Potassium carbonate was added (942 mg, 6.81 mmol, 3 equiv.) to the suspension, and the reaction was stirred at 70° C. for 18 h. The reaction mixture was cooled to room temperature then quenched with 1 N HCl. The reaction mixture was partitioned between water (15 mL) and dichloromethane (15 mL) and the layers were separated. The aqueous layer was extracted with dichloromethane (2×15 mL), and the combined organic layers were concentrated to provide ethyl 6-bromo-1-((1-methylpiperidin-4-yl)methyl)-4-oxo-1,4-dihydro-1,8-naphthyridine-3-carboxylate (945 mg, >99%).

Calcd for $C_{18}H_{22}BrN_3O_3$ $[M+H]^+$: 409.9.

Intermediate 2

The following intermediate was prepared according to the procedure described for Intermediate 1 from the indicated starting material.

| Int | Compound | Data | SM |
|---|---|---|---|
| 2 | Ethyl 6-bromo-1-(2-(1-methylpiperidin-4-yl)ethyl)-4-oxo-1,4-dihydro-1,8-naphthyridine-3-carboxylate | Calcd for $C_{19}H_{24}BrN_3O_3$ $[M + H]^+$: 424.1<br>$^1$NMR ($d_6$-DMSO) δ 8.89 (d, 1H), 8.87 (s, 1H), 8.63 (d, 1H), 4.49-4.44 (m, 2H), 4.28-4.21 (m, 2H), 2.74-2.68 (m, 2H), 2.2 (s, 3H), 1.81-1.64 (m, 4H), 1.29 (t, 3H), 1.27-1.15 (m, 5H) | Intermediate 3 & 2-(1-methylpiperidin-4-yl)ethan-1-amine |

Intermediate 3

Ethyl 2-(5-bromo-2-fluoronicotinoyl)-3-(dimethylamino)acrylate

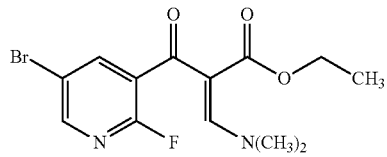 [SMILES: CCOC(=O)/C(=C\N(C)C)C(=O)c1cc(Br)cnc1F]

To a solution of 5-bromo-2-fluoronicotinic acid (3 g, 13.64 mmol) in toluene (30 mL) was added thionyl chloride (5 mL, 68.18 mmol, 5 equiv.) followed by DMF (0.5 mL). This was stirred at 110° C. for 2 h then concentrated in vacuo. The residue was resuspended in THF (15 mL) and added dropwise to a solution of ethyl 3-(dimethylamino)acrylate (2 mL, 13.64 mmol) and triethylamine (2.85 mL, 20.45 mmol) in THF (15 mL). The reaction was stirred at 70° C. for 18 h, cooled down to room temperature, and quenched with water. The reaction was partitioned between water (70 mL) and ethyl acetate (70 mL) and the layers were separated. The aqueous layer was extracted with ethyl acetate (2×70 mL). The combined organic layers were washed with 1 N HCl (100 mL) and brine (100 mL), dried over sodium sulftate, and concentrated. The concentrate was purified via silica gel chromatography to provide ethyl 2-(5-bromo-2-fluoronicotinoyl)-3-(dimethylamino)acrylate as an orange solid (3.64 g, 77%).

$^1$NMR (d$_6$-DMSO) δ 8.42 (d, 1H), 8.15 (dd, 1H), 7.91 (s, 1H), 3.94-3.87 (m, 2H), 3.38 (s, 3H), 2.83 (s, 3H), 0.92 (t, 3H).

Intermediate 4

Methyl 5-bromo-2-(3-ethylureido)isonicotinate

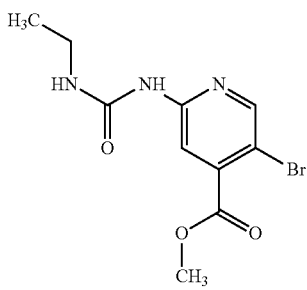 [SMILES: CCNC(=O)Nc1cc(C(=O)OC)c(Br)cn1]

Methyl 2-amino-5-bromoisonicotinate (200 g, 865 mmol) was dissolved in chloroform (1.2 L) and placed into a 2 L Parr apparatus. Ethyl isocyanate (204 mL, 2.59 mol) was added, and the Parr apparatus was heated at 40° C. for 36 h at which time the reaction was determined to be complete. The mixture was then cooled to room temperature, concentrated, and the solid was dissolved in 2:1 ethyl acetate: tetrahydrofuran (3 L). This solution was extracted with water (1 L), and the water was back extracted with ethyl acetate (300 mL). The organic layers were combined then dried over sodium sulfate, filtered, and concentrated yielding 261 g (quant) of methyl 5-bromo-2-(3-ethylureido)isonicotinate as a dark yellow solid.

MS (ESP): 302.0 (MH$^+$) for C$_{10}$H$_{12}$BrN$_3$O$_3$.

$^1$H NMR (300 MHz, CDCl$_3$): δ 1.22 (t, 3H), 3.41 (q, 2H), 7.22 (s, 1H), 7.30 (s, 1H), 8.38 (s, 1H), 8.70 (s, 1H), 9.42 (s, 1H).

Intermediate 5

5-Bromo-2-(3-ethylureido)isonicotinamide

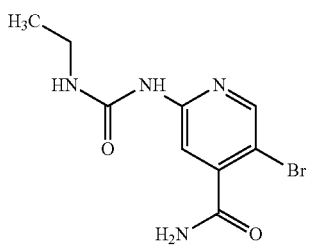 [SMILES: CCNC(=O)Nc1cc(C(N)=O)c(Br)cn1]

A solution of methyl 5-bromo-2-(3-ethylureido)isonicotinate (Intermediate 4, 261 g, 865 mmol) and 7N ammonia in methanol (1.7 L) was allowed to stir at room temperature for 3 d. The solid that precipitated was then collected by filtration, rinsed with methanol (2×500 mL), and then dried on a high vacuum pump overnight, yielding 237 g (95%) of 5-bromo-2-(3-ethylureido)isonicotinamide as a smooth white solid.

MS (ESP): 287.0 (MH$^+$) for C$_9$H$_{11}$BrN$_4$O$_2$.

$^1$H NMR (300 MHz, DMSO-d$_6$): δ 1.1 (t, 3H), 3.18 (q, 2H), 7.40 (s, 1H), 7.60 (s, 1H), 7.80 (s, 1H), 8.1 (s, 1H), 8.38 (s, 1H), 9.39 (s, 1H).

Intermediate 6

5-Bromo-2-(3-ethylureido)pyridine-4-carbothioamide

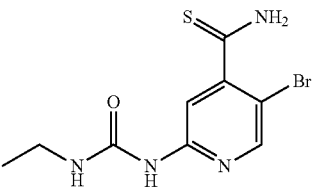 [SMILES: CCNC(=O)Nc1cc(C(N)=S)c(Br)cn1]

A suspended mixture of 5-bromo-2-(3-ethylureido)isonicotinamide (Intermediate 5, 237 g, 830 mmol), Lawesson's Reagent (336 g, 830 mmol), and tetrahydrofuran (3 L) was stirred at 70° C. for 18 h. The precipitate was collected by filtration and washed with methyl tert-butyl ether (2×500 L). This solid was then dried in the vacuum oven at 50° C. for 12 h to give 192 g (77%) of 5-bromo-2-(3-ethylureido)pyridine-4-carbothioamide as an off white solid.

MS (ESP): 304.1 (MH$^+$) for C$_9$H$_{11}$BrN$_4$OS.

$^1$H NMR (300 MHz, DMSO-d$_6$): δ 1.1 (t, 3H), 3.18 (q, 2H), 7.38 (s, 1H), 7.50 (s, 1H), 8.28 (s, 1H), 9.25 (s, 1H), 9.80 (s, 1H), 10.28 (s, 1H).

Intermediate 7

1-(5-Bromo-4-(4-hydroxy-4-(trifluoromethyl)-4,5-dihydrothiazol-2-yl)pyridin-2-yl)-3-ethylurea

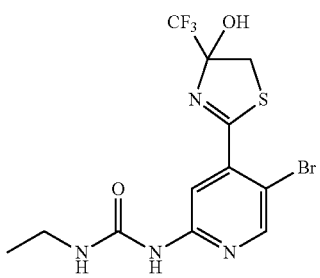 [SMILES: CCNC(=O)Nc1cc(C2=NC(O)(C(F)(F)F)CS2)c(Br)cn1]

A suspension of 5-bromo-2-(3-ethylureido)pyridine-4-carbothioamide (Intermediate 6, 160 g, 510 mmol), 3-bromo-1,1,1-trifluoroacetone (200 g, 1.02 mol) in acetonitrile (3 L) was heated at 80° C. for 20 h. The solution was then cooled down and concentrated. 2:1 Acetonitrile: methyl tert-butyl ether (2.4 L) was added, and the solution thus obtained was placed on a rotovap, and the volume of solvent was reduced by half. The precipitate that formed was filtered and dried in a vacuum oven at 40° C. After letting the filtrate sit, more solid precipitated out and an additional two crops of precipitate were collected and dried in the vacuum oven at 40° C. resulting in a combined collection of 202.4 g (92%) of 1-(5-bromo-4-(4-hydroxy-4-(trifluoromethyl)-4,5-dihydrothiazol-2-yl)pyridin-2-yl)-3-ethylurea as pale yellow solid.

MS (ESP): 413.0 (MH$^+$) for $C_{12}H_{12}BrF_3N_4O_2S$.

$^1$H NMR (300 MHz, DMSO-d$_6$): δ 1.05 (t, 3H), 3.10 (q, 2H), 3.60 (d, 1H), 3.85 (d, 1H), 7.58 (s, 1H), 7.95 (s, 1H), 8.42 (s, 1H), 9.42 (s, 1H).

Intermediate 8

1-(5-Bromo-4-(4-(trifluoromethyl)thiazol-2-yl)pyridin-2-yl)-3-ethylurea

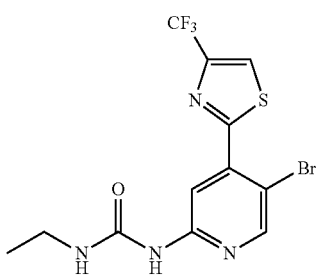 [SMILES: CCNC(=O)Nc1cc(-c2nc(C(F)(F)F)cs2)c(Br)cn1]

A suspension of 1-(5-bromo-4-(4-hydroxy-4-(trifluoromethyl)-4,5-dihydrothiazol-2-yl)pyridin-2-yl)-3-ethylurea (Intermediate 7, 175.8 g, 430 mmol) and triethylamine (295 mL, 2.13 mol) in tetrahydrofuran (3 L) was prepared and stirred at room temperature. Methane sulfonyl chloride (106 mL, 1.36 mol) was added dropwise over the course of an hour. This mixture was stirred at room temperature for 6 hours. The solid was collected by filtration, rinsed with tetrahydrofuran (2×500 mL), and the filtrate was retained while the solid was discarded. The combined tetrahydrofuran layers were concentrated to a viscous, yellow semi-solid which was then washed with water (2×500 mL). This solid was further stirred with water (500 mL) for 18 hours, then filtered and dried in the vacuum oven at 50° C. for 12 hours to give 121.8 g (73%) of 1-(5-bromo-4-(4-(trifluoromethyl)thiazol-2-yl)pyridin-2-yl)-3-ethylurea as an off-white solid.

MS (ESP): 395.0 (MH$^+$) for $C_{12}H_{10}BrF_3N_4OS$.

$^1$H NMR (300 MHz, DMSO-d$_6$): δ 1.1 (t, 3H), 3.20 (q, 2H), 7.23 (s, 1H), 8.40 (s, 1H), 8.60 (s, 1H), 8.83 (s, 1H), 9.40 (s, 1H).

Intermediate 9

6-(3-Ethylureido)-4-(4-(trifluoromethyl)thiazol-2-yl)pyridin-3-ylboronic acid

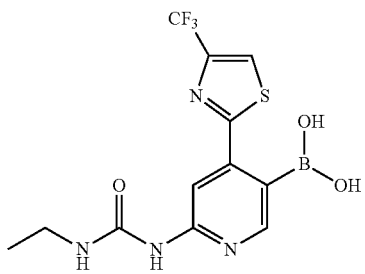 [SMILES: CCNC(=O)Nc1cc(-c2nc(C(F)(F)F)cs2)c(B(O)O)cn1]

A suspension of 1-(5-bromo-4-(4-(trifluoromethyl)thiazol-2-yl)pyridin-2-yl)-3-ethylurea (Intermediate 8, 50 g, 130 mmol) in tetrahydrofuran (1.25 L) was prepared and stirred at −50° C. 2.0 M Isopropyl magnesium chloride in tetrahydrofuran (165 mL, 330 mmol) was added dropwise over 45 min so that the temperature never rose above −35° C. The reaction was stirred for a further hour at −40° C. then was cooled to −78° C. 2.5 M n-Butyl lithium in hexanes (293 mL, 730 mmol) was then added dropwise to the reaction mixture over the course of 1 h so that the temperature never rose above −65° C. This mixture was then allowed to return to −78° C. for 1.5 h. Boron methoxide (155 mL, 1.39 mol) was added in 1 portion and the cold bath was removed. At this point a sticky solid formed, and the reaction mixture was stirred vigorously. The reaction was allowed to warm to room temperature and stir for 1 hour. 6N Hydrochloric acid (300 mL) was then added slowly to minimize foaming and the reaction was stirred at room temperature for 30 minutes so that all of the solids were dissolved. The reaction was concentrated to remove the tetrahydrofuran then water (1 L) was added. The solution was basified to pH 10 with 25% sodium hydroxide and the total volume was increased to 2 L with water. The aqueous solution was extracted with methyl tert-butyl ether (3×650 mL). The organic layers were combined and extracted with 5% sodium hydroxide (500 mL). The aqueous phases were combined and acidified to pH 5.5 with 6N hydrochloric acid to form a suspension. This suspension was extracted with 2:1 ethyl acetate:THF (3×1.3 L) making sure all of the solid dissolved in the organic layer. The organic layers were combined and back washed with water (1 L) then concentrated. The concentrate was triturated with methyl tert-butyl ether (1 L). The solid obtained was dried in a vacuum oven at 50° C. for 18 hours to give 35 g (77%) of 6-(3-ethylureido)-4-(4-(trifluoromethyl)thiazol-2-yl)pyridin-3-ylboronic acid as an off-white solid.

MS (ESP): 361.2 (M+H⁺) for $C_{12}H_{12}BF_3N_4O_3S$.

¹H NMR (300 MHz, DMSO-d₆): δ 1.10 (t, 3H), 3.18 (m, 2H), 7.75 (brt, 1H), 7.91 (s, 1H), 8.18 (br, 2H), 8.31 (s, 1H), 8.64 (s, 1H), 9.31 (s, 1H).

Intermediate 10

5-Bromo-2-hydroxypyridine-3-carboxylic acid

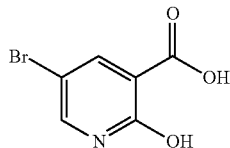 [SMILES: O=C(O)c1cc(Br)cnc1O]

To a solution of 2-hydroxypyridine-3-carboxylic acid (2 g, 14.3 mmol) in 50% sodium hydroxide (2.7 g, 67.5 mmol) diluted with water (10 mL) was added sodium hypobromite solution (15 mL). The sodium hypobromite solution was prepared by adding bromine (1.81 g, 11.3 mmol) to a solution of 50% sodium hydroxide (3.4 g, 84.5 mmol) in water (15 mL) at 0° C. then diluting the solution to 50 mL. After 3 d, the reaction solution was cooled in an ice-bath and acidified carefully with 12 N hydrochloric acid solution. The solid that formed was collected by filtration and washed with water then dried to afford 1.4 g (70%) of 5-bromo-2-hydroxypyridine-3-carboxylic acid.

¹H NMR (400 MHz, DMSO-d₆): δ 8.11 (s, 1H), 8.15 (s, 1H).

Mass (APCI−ve Scan): m/z 217.9 (M−H).

Intermediate 11

5-Bromo-2-chloropyridine-3-carboxylic acid

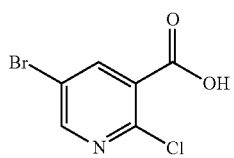 [SMILES: O=C(O)c1cc(Br)cnc1Cl]

To 5-bromo-2-hydroxypyridine-3-carboxylic acid (Intermediate 10, 14 g, 64.2 mmol) was added thionyl chloride (70 mL) and dimethylformamide (8 mL). The reaction mixture was heated to reflux for 3 h. After cooling, the excess thionyl chloride was removed by rotary evaporation and the residue was poured into water (1 L) and extracted with ethyl acetate (3×100 mL). The organic layer was dried over anhydrous sodium sulphate then filtered and concentrated to afford 7.0 g (47%) of 5-bromo-2-chloropyridine-3-carboxylic acid.

¹H NMR (400 MHz DMSO-d₆): δ 8.44 (s, 1H), 8.72 (s, 1H).

Mass (APCI−ve Scan): m/z 235.9 (M−H).

Intermediate 12

Ethyl 3-(5-bromo-2-chloropyridin-3-yl)-3-oxopropanoate

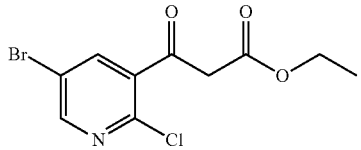 [SMILES: CCOC(=O)CC(=O)c1cc(Br)cnc1Cl]

To a suspension of 5-bromo-2-chloropyridine-3-carboxylic acid (Intermediate 11, 7.0 g, 29.7 mmol) in anhydrous tetrahydrofuran (70 mL), 1,1'-carbonylbis(1H-imidazole) (CDI) (5.8 g, 35.7 mmol) was added. The reaction mixture was heated to reflux for 2 h then cooled to room temperature and the crude solution was used in the next step with out further purification. A solution of 3-ethoxy-3-oxopropanoic acid (3.93 g, 29.7 mmol) in anhydrous tetrahydrofuran (80 mL) was cooled to 0° C. and methyl magnesium bromide in diethyl ether (16 mL, 3M solution) was added in drop wise manner. After stirring for 20 min at 0° C., the crude solution which was prepared from Intermediate 11 and CDI was added and the reaction was heated to 60° C. After heating for 16 h, the reaction mixture was cooled to room temperature and then poured into water. The pH was adjusted to 5 with concentrated hydrochloric acid solution, and the solution was extracted with ethyl acetate. The organic layer was dried with anhydrous sodium sulphate and concentrated under reduce pressure to afford ethyl 3-(5-bromo-2-chloropyridin-3-yl)-3-oxopropanoate (5.0 g, 55%) as a reddish oil.

Intermediate 13

Ethyl(2Z)-2-[(5-bromo-2-chloropyridin-3-yl)carbonyl]-3-ethoxyprop-2-enoate

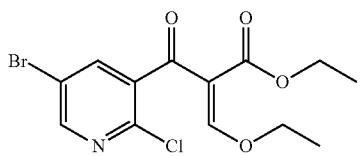 [SMILES: CCO/C=C(\C(=O)OCC)C(=O)c1cc(Br)cnc1Cl]

Ethyl 3-(5-bromo-2-chloropyridin-3-yl)-3-oxopropanoate (Intermediate 12, 1.0 g, 3.26 mmol) was suspended in acetic anhydride (0.83 g, 8.16 mM) and 1,1',1''-[methanetriyltris(oxy)]triethane (0.725 g, 4.90 mmol) was added. The reaction mixture was heated to 130° C. for 3 h then cooled to room temperature and concentrated under reduced pressure. The residue so obtained was co-distilled with xylene (2-3 times) to obtain ethyl (2Z)-2-[(5-bromo-2-chloropyridin-3-yl)carbonyl]-3-ethoxyprop-2-enoate (1.1 g) which was taken without further purification to the next step.

Intermediate 14

Ethyl(2Z)-2-[(5-bromo-2-chloropyridin-3-yl)carbonyl]-3-(ethylamino)prop-2-enoate

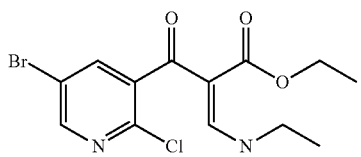 [SMILES: CCN/C=C(\C(=O)OCC)C(=O)c1cc(Br)cnc1Cl]

The residue ethyl (2Z)-2-[(5-bromo-2-chloropyridin-3-yl)carbonyl]-3-ethoxyprop-2-enoate (Intermediate 13, 1.1 g; 3.03 mmol) was suspended in dichloromethane (50 mL) and ethylamine gas was bubbled through the mixture until the starting material disappeared. The reaction mixture was washed with water and the organic layer was dried with anhydrous sodium sulphate and concentrated under reduced pressure to afford 700 mg (63.9%) of ethyl (2Z)-2-[(5-bromo-2-chloropyridin-3-yl)carbonyl]-3-(ethylamino)prop-2-enoate which was taken without further purification to the next step.

Intermediate 15

Ethyl 6-bromo-1-ethyl-4-oxo-1,4-dihydro-1,8-naphthyridine-3-carboxylate

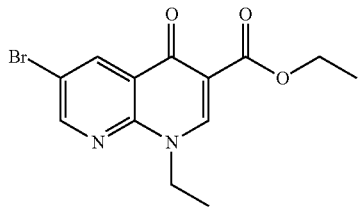 [SMILES: CCOC(=O)c1cn(CC)c2ncc(Br)cc2c1=O]

The above crude compound ethyl (2Z)-2-[(5-bromo-2-chloropyridin-3-yl)carbonyl]-3-(ethylamino)prop-2-enoate (Intermediate 14, 700 mg) was suspended in acetonitrile (30 mL) and potassium carbonate (0.9 g, 6.53 mmol) and ethylamine (1 eq) were added. The mixture was heated to 80° C. for 16 h then cooled to room temperature and filtered to remove potassium carbonate. Water was added to the filtrate and the precipitated product was filtered and dried to afford 500 mg, 50% of ethyl 6-bromo-1-ethyl-4-oxo-1,4-dihydro-1,8-naphthyridine-3-carboxylate.

$^1$H NMR (400 MHz, DMSO-d$_6$): δ 1.27 (t, 3H), 1.34 (t, 3H), 4.22-4.27 (q, 2H), 4.45-4.50 (q, 2H), 8.63 (s, 1H), 8.88 (s, 1H), 8.98 (s, 1H).

LC-MS: m/z 325.1 (M+H), 327 (M+2).

Intermediates 16-19

The following Intermediates were prepared according to the procedure described for Intermediate 15 from the indicated starting material.

| Int | Compound | Data | SM |
| --- | --- | --- | --- |
| 16 | Ethyl 6-bromo-1-cyclopropyl-4-oxo-1,4-dihydro-1,8-naphthyridine-3-carboxylate | $^1$H NMR (400 MHz, DMSO-d$_6$): δ 1.04-1.08 (m, 2H), 1.12-1.14 (m, 2H), 1.27-1.30 (t, 3H), 3.67-3.70 (m, 1H), 4.21-4.27 (q, 2H), 8.60 (s, 1H), 9.01 (s, 1H). LC-MS: m/z 337.1 (M + H) | Intermediate 14 & cyclopropylamine |
| 17 | Ethyl 6-bromo-1-(2-hydroxyethyl)-4-oxo-1,4-dihydro-1,8-naphthyridine-3-carboxylate | $^1$H NMR (400 MHz, DMSO-d$_6$): δ 1.29-1.38 (t, 3H), 4.17-4.24 (t, 2H), 4.25-4.27 (q, 2H), 4.54-4.56 (t, 2H), 4.82 (br s, 1H), 8.19-8.22 (br s, 1H), 8.71-8.73 (s, 2H) LC-MS: m/z 341.1 (M + H) | Intermediate 14 and 2-hydroxyethyl amine |

| Int | Compound | Data | SM |
|---|---|---|---|
| 18 | Ethyl 6-bromo-1-[(2S)-1-hydroxy-4-methylpentan-2-yl]-4-oxo-1,4-dihydro-1,8-naphthyridine-3-carboxylate | $^1$H NMR (400 MHz, DMSO-$d_6$): δ 0.86 (d, 6H), 1.27-1.36 (m, 3H), 1.39 (m, 1H), 1.69 (m, 1H), 1.70 (m, 1H), 3.67 (m, 2H), 4.24 (q, 2H), 5.10 (s, 1H), 5.86 (br, 1H), 8.66 (s, 1H), 8.75 (s, 1H), 8.97 (s, 1H). LC-MS: m/z 399 (M + 2) | Intermediate 14 and (S)-leucinol |
| 19 | Ethyl 6-bromo-1-[(2S)-1-hydroxy-3,3-dimethylbutan-2-yl]-4-oxo-1,4-dihydro-1,8-naphthyridine-3-carboxylate | $^1$H NMR (400 MHz, DMSO-$d_6$): δ 1.02 (s, 9H), 1.27-1.30 (t, 3H), 3.99-4.02 (q, 2H), 4.25-4.29 (m, 2H), 4.99-5.02 (t, 1H), 5.69-5.72 (q, 1H), 8.68-8.76 (d, 2H), 8.97-8.98 (d, 1H). LC-MS: m/z 399.2 (M + 2) | Intermediate 14 and (2S)-2-amino-3,3-dimethylbutan-1-ol |

Intermediate 20

Ethyl 6-bromo-1-{2-[(methylsulfonyl)oxy]ethyl}-4-oxo-1,4-dihydro-1,8-naphthyridine-3-carboxylate

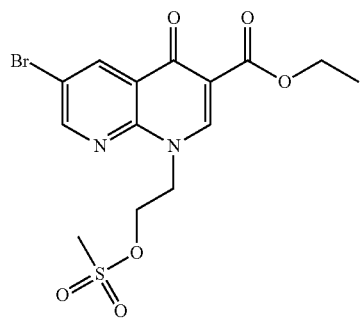 [SMILES: CCOC(=O)c1cn(CCOS(C)(=O)=O)c2ncc(Br)cc2c1=O]

A solution of ethyl 6-bromo-1-(2-hydroxyethyl)-4-oxo-1,4-dihydro-1,8-naphthyridine-3-carboxylate (Intermediate 17, 800 mg, 2.34 mmol) and triethylamine (473 mg, 4.69 mmol) in dichloromethane (50 mL) was cooled to 0° C. and methane sulphonyl chloride (400 mg, 3.50 mmol) was added drop wise. The mixture was allowed to stir at room temperature for 3 h. The reaction mixture was washed with water and the organic layer was dried over anhydrous sodium sulphate and concentrated under reduced pressure to afford 700 mg, (71%) of ethyl 6-bromo-1-{2-[(methylsulfonyl)oxy]ethyl}-4-oxo-1,4-dihydro-1,8-naphthyridine-3-carboxylate, which was taken without further purification to next step.

Intermediate 21

Ethyl 6-bromo-1-[2-(dimethylamino)ethyl]-4-oxo-1,4-dihydro-1,8-naphthyridine-3-carboxylate

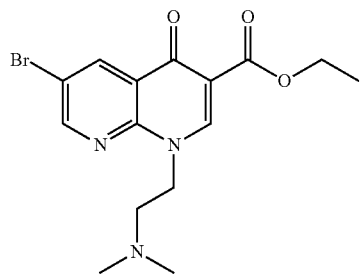 [SMILES: CCOC(=O)c1cn(CCN(C)C)c2ncc(Br)cc2c1=O]

A solution of ethyl 6-bromo-1-{2-[(methylsulfonyl)oxy]ethyl}-4-oxo-1,4-dihydro-1,8-naphthyridine-3-carboxylate (Intermediate 20, 700 mg, 1.67 mmol) in dichloromethane was purged with N,N-dimethylethane-1,2-diamine gas until the starting material disappeared. The reaction mixture was washed with water, and the organic layer was dried over anhydrous sodium sulphate and concentrated under reduced pressure to afford ethyl 6-bromo-1-[2-(dimethylamino)ethyl]-4-oxo-1,4-dihydro-1,8-naphthyridine-3-carboxylate 300 mg, (49%).

$^1$H NMR (400 MHz, DMSO-$d_6$): δ 1.29 (t, 3H), 2.19 (s, 6H), 2.62 (t, 2H), 4.25 (q, 2H), 4.53 (t, 2H), 8.63 (s, 1H), 8.81 (s, 1H), 8.95 (s, 1H).

LC-MS: m/z 370 (M+2).

Intermediate 22

6-Bromo-1-ethyl-4-oxo-1,4-dihydro-1,8-naphthyridine-3-carboxylic acid

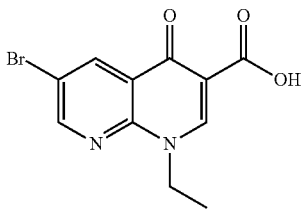 [SMILES: CCn1cc(C(=O)O)c(=O)c2cc(Br)cnc21]

To a solution of ethyl 6-bromo-1-ethyl-4-oxo-1,4-dihydro-1,8-naphthyridine-3-carboxylate (Intermediate 15, 470 mg, 1.44 mmol) dissolved in ethanol (30 mL) was added 10% potassium hydroxide (2.9 mL, 2.89 mmol) and the mixture was heated to 175° C. for 1 h. The solvent was evaporated under reduced pressure to a residue. Water (20 mL) was added to the residue and the pH was adjusted to 3 with dilute hydrochloric acid (2N) to give solid precipitate which was filtered and dried to afford 340 mg (80%) of 6-bromo-1-ethyl-4-oxo-1,4-dihydro-1,8-naphthyridine-3-carboxylic acid.

$^1$H NMR (400 MHz, DMSO-$d_6$): δ 1.41 (t, 3H), 4.66 (q, 2H), 8.84 (d, 1H), 9.17 (d, 1H), 9.26 (s, 1H), 14.42 (s, 1H).

MASS (APCI+ve Scan): m/z 299 (M+2H).

Intermediate 23

2-Hydroxyethyl 6-bromo-1-ethyl-4-oxo-1,4-dihydro-1,8-naphthyridine-3-carboxylate

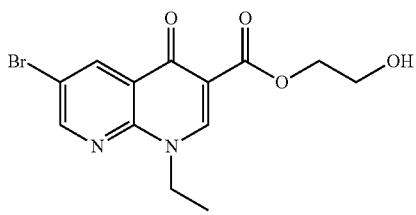 [SMILES: CCn1cc(C(=O)OCCO)c(=O)c2cc(Br)cnc21]

6-Bromo-1-ethyl-4-oxo-1,4-dihydro-1,8-naphthyridine-3-carboxylic acid (Intermediate 22, 1.7 g, 5.72 mmol), ethane-1,2-diol (1.91 g, 34.34 mmol) and triphenylphosphine (9.0 g, 34.34 mmol) were dissolved in tetrahydrofuran (100 mL). Diethyl azodicarboxylate (DEAD) (4.97 g, 28.61 mol) was added drop wise and the mixture was stirred for 16 h at room temperature. The mixture was concentrated under reduced pressure, and water (100 mL) was added. The aqueous mixture was extracted with ethyl acetate (2×100 mL) and the combined organic layers were dried over anhydrous sodium sulfate, filtered and concentrated under reduced pressure to give a crude compound. The crude compound was purified by flash column chromatography over silica gel (100-200 mesh) using eluent gradient of ethyl acetate/petroleum ether: 1:1 to 100:0 to afford 1.6 g (82%) of 2-hydroxyethyl 6-bromo-1-ethyl-4-oxo-1,4-dihydro-1,8-naphthyridine-3-carboxylate.

$^1$H NMR (400 MHz, CDCl$_3$): δ 1.53 (t, 3H), 3.56 (t, 1H), 3.94 (t, 2H), 4.49 (m, 4H), 8.64 (s, 1H), 8.79 (s, 1H), 8.88 (s, 1H).

MASS (APCI+ve Scan): m/z 342 (M+2H).

Intermediate 24

3-Hydroxypropyl 6-bromo-1-ethyl-4-oxo-1,4-dihydro-1,8-naphthyridine-3-carboxylate

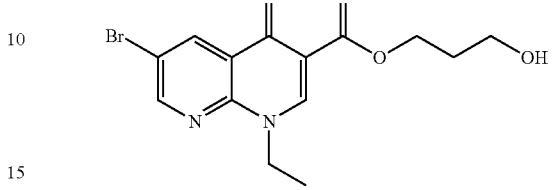

6-Bromo-1-ethyl-4-oxo-1,4-dihydro-1,8-naphthyridine-3-carboxylic acid (2.0 g, 6.73 mM), propane-1,3-diol (Intermediate 22, 2.047 g, 26.93 mmol) and triphenylphosphine (7.058 g, 26.93 mmol) were dissolved in tetrahydrofuran (80 mL). Diethyl azodicarboxylate (DEAD) (3.51 g, 20.02 mmol) was added and the mixture was stirred for 16 h at room temperature. The solvent was evaporated under reduced pressure and water (100 mL) was added to the residue. The aqueous mixture was extracted with ethyl acetate (2×100 mL) and the combined organic layers were dried over anhydrous sodium sulfate, filtered and concentrated under reduced pressure to give a crude compound. The crude compound was purified by flash column chromatography over silica gel (100-200 mesh) and the product was eluted with a gradient of 50% ethyl acetate/petroleum ether to 100% ethyl acetate to afford 1.8 g (80%) of 3-hydroxypropyl 6-bromo-1-ethyl-4-oxo-1,4-dihydro-1,8-naphthyridine-3-carboxylate.

$^1$H NMR (400 MHz, DMSO-$d_6$): δ 1.39 (t, 3H), 1.86 (q, 2H), 3.59 (m, 2H), 4.27 (q, 2H), 4.52 (q, 2H), 4.58 (m, 1H), 8.64 (s, 1H), 8.87 (s, 1H), 9.00 (s, 1H).

MASS (APCI+ve Scan): m/z 356 (M+2H).

Intermediate 25

2-{[Bis(benzyloxy)phosphoryl]oxy}ethyl 6-bromo-1-ethyl-4-oxo-1,4-dihydro-1,8-naphthyridine-3-carboxylate

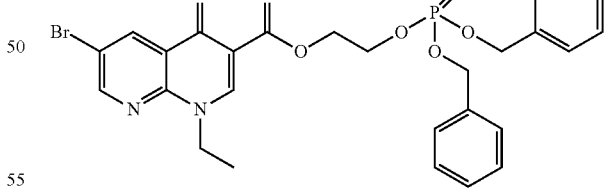

2-Hydroxyethyl 6-bromo-1-ethyl-4-oxo-1,4-dihydro-1,8-naphthyridine-3-carboxylate (Intermediate 23, 100 mg, 0.29 mol), dibenzyl hydrogen phosphate (65 mg, 0.23 mmol) and triphenylphosphine (192 mg, 0.733 mmol) were dissolved in tetrahydrofuran (15 mL). Diisopropyl azodicarboxylate [DIAD] (106 mg, 0.52 mmol) was added drop wise and the mixture was stirred for 4 h at room temperature. The reaction mixture was concentrated under reduced pressure and water (100 mL) was added. The aqueous mixture was extracted with ethyl acetate (2×100 mL) and the combined organic layers were dried over anhydrous sodium sulphate, filtered and concentrated under reduced pressure to give a crude compound. The crude compound was purified by flash column chromatography over silica gel (10-50% ethyl acetate/petroleum ether) to afford 60 mg (40%) of 2-{[bis(benzyloxy)phosphoryl]oxy}ethyl 6-bromo-1-ethyl-4-oxo-1,4-dihydro-1,8-naphthyridine-3-carboxylate.

$^1$H NMR (400 MHz, DMSO-d$_6$): δ 1.36 (t, 3H), 4.04 (m, 1H), 4.2-4.44 (m, 5H), 5.02 (m, 4H), 7.28 (m, 10H), 8.59 (s, 1H), 8.94 (s, 1H), 8.99 (s, 1H).

LC-MS: m/z 601 (M+H).

Intermediate 26

3-{[Bis(benzyloxy)phosphoryl]oxy}propyl 6-bromo-1-ethyl-4-oxo-1,4-dihydro-1,8-naphthyridine-3-carboxylate

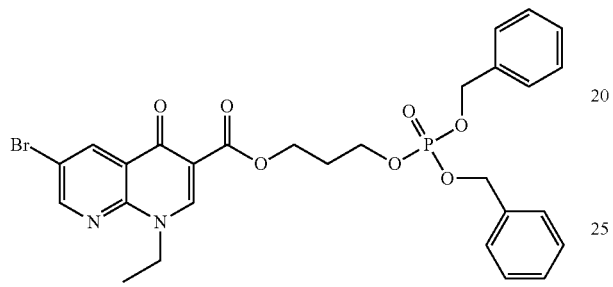

3-Hydroxypropyl 6-bromo-1-ethyl-4-oxo-1,4-dihydro-1,8-naphthyridine-3-carboxylate (Intermediate 24, 100 mg, 0.28 mmol), dibenzyl hydrogen phosphate (124 mg, 0.44 mmol) and triphenylphosphine (367 mg, 1.4 mmol) was dissolved in tetrahydrofuran (15 mL). Diisopropyl azodicarboxylate [DIAD] (281 mg, 1.40 mmol) was added and the mixture was stirred for 4 h at room temperature. The reaction mixture was concentrated under reduced pressure and water (100 mL) was added. The aqueous mixture was extracted with ethyl acetate (2×100 mL) and the combined organic layers were dried over anhydrous sodium sulphate, filtered and concentrated under reduced pressure to give a crude compound. The crude compound was purified by flash column chromatography over silica gel (0-50% ethyl acetate/petroleum ether) to afford 80 mg (47%) of 3-{[bis(benzyloxy)phosphoryl]oxy}propyl 6-bromo-1-ethyl-4-oxo-1,4-dihydro-1,8-naphthyridine-3-carboxylate NMR (CHCl$_3$): δ 1.44 (t, 3H), 2.08 (q, 2H), 4.21 (q, 2H), 4.41 (m, 4H), 5.02 (m, 2H), 7.27 (m, 10H), 8.81 (s, 1H), 8.86 (s, 1H), 8.92 (s, 1H).

Intermediate 27

Ethyl(2Z)-2-[(5-bromo-2-chloropyridin-3-yl)carbonyl]-3-{[(2S)-1-hydroxy-4-methylpentan-2-yl]amino}prop-2-enoate

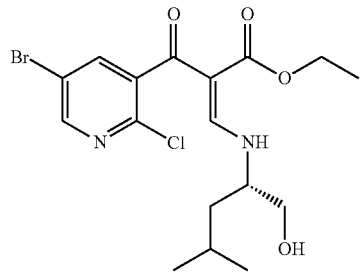 [SMILES: CCOC(=O)/C(=C\N[C@H](CO)CC(C)C)C(=O)c1cc(Br)cnc1Cl]

The crude ethyl (2Z)-2-[5-bromo-2-chloropyridin-3-yl)carbonyl]-3-ethoxyprop-2-enoate (Intermediate 13, 3.2 g) was dissolved in dichloromethane (30 mL) and (2S)-2-amino-4-methylpentan-1-ol (2.17 g, 14.7 mmol) was added. The mixture was stirred for 30 min at room temperature. Dichloromethane (70 mL) was added to the reaction mixture and the mixture was washed with water (2×100 mL). The organic layer was dried over anhydrous sodium sulphate, filtered and concentrated under reduced pressure to give a thick mass which was purified by flash column chromatography. The product was eluted with the gradient of 20% ethyl acetate/petroleum ether to afford colorless thick mass 2.5 g (80%) of ethyl (2Z)-2-[(5-bromo-2-chloropyridin-3-yl)carbonyl]-3-{[(2S)-1-hydroxy-4-methylpentan-2-yl]amino}prop-2-enoate.

$^1$H NMR (400 MHz, CDCl$_3$): δ 1.11 (s, 6H), 1.31 (d, 1H), 1.44 (d, 1H), 1.59 (d, 1H), 1.75 (t, 3H), 2.18 (d, 1H), 3.58 (d, 1H), 3.67 (d, 1H), 3.82 (d, 1H), 4.02 (q, 2H), 7.64 (s, 1H), 8.22 (d, 1H), 8.41 (s, 1H), 10.98 (d, 1H).

MASS (APCI+ve Scan): m/z 435 (M+2).

Intermediate 28

Ethyl 1-[(2S)-1-{[bis(benzyloxy)phosphoryl]oxy}-4-methylpentan-2-yl]-6-bromo-4-oxo-1,4-dihydro-1,8-naphthyridine-3-carboxylate

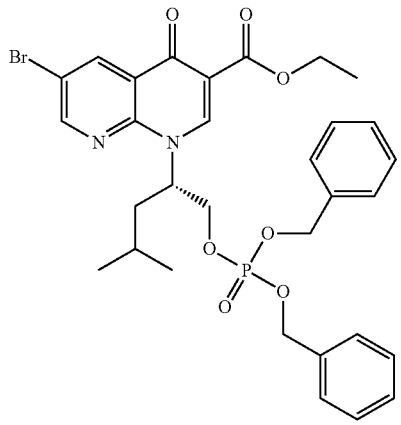 [SMILES: CCOC(=O)c1cn([C@H](COP(=O)(OCc2ccccc2)OCc2ccccc2)CC(C)C)c2ncc(Br)cc2c1=O]

Ethyl(2Z)-2-[(5-bromo-2-chloropyridin-3-yl)carbonyl]-3-{[(2S)-1-hydroxy-4-methylpentan-2-yl]amino}prop-2-enoate (Intermediate 27, 415 mg, 0.95 mmol) and triphenylphosphine (409 mg, 1.47 mmol) were dissolved in tetrahydrofuran (30 mL). Diisopropyl azodicarboxylate [DIAD] (0.4 mL, 2.35 mmol) was added and the mixture was stirred for 1 h at room temperature. A second portion of triphenylphosphine (625 mg) and diisopropyl azodicarboxylate [DIAD] (0.4 mL) were added and the mixture was stirred for an additional 5 h at room temperature. The reaction mixture was concentrated under reduced pressure to give a crude compound. The crude compound was purified by flash column chromatography over silica gel (10-30% ethyl acetate/petroleum ether to afford 700 mg (60%) of ethyl 1-[(2S)-1-{[bis(benzyloxy)phosphoryl]oxy}-4-methylpentan-2-yl]-6-bromo-4-oxo-1,4-dihydro-1,8-naphthyridine-3-carboxylate as liquid.

$^1$H NMR (400 MHz, DMSO-d$_6$): δ 0.94 (d, 6H), 1.24 (t, 3H), 1.38 (d, 1H), 1.66 (d, 1H), 1.88 (d, 1H), 4.22 (q, 2H), 4.48 (2s, 2H), 4.85 (d, 4H), 6.01 (d, 1H), 7.15-7.41 (m, 10H), 8.62 (s, 1H), 8.79 (s, 1H), 8.97 (s, 1H).

LC-MS: m/z 659 (M+H).

Intermediate 29

(R)-ethyl 6-bromo-1-(1-(tert-butoxycarbonyl)piperidin-3-yl)-4-oxo-1,4-dihydro-1,8-naphthyridine-3-carboxylate

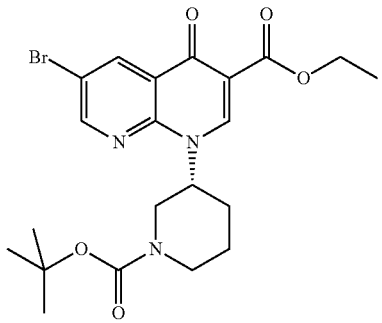 [SMILES: CCOC(=O)c1cn([C@@H]2CCCN(C(=O)OC(C)(C)C)C2)c2ncc(Br)cc2c1=O]

Ethyl 2-(5-bromo-2-fluoronicotinoyl)-3-(dimethylamino)acrylate (Intermediate 3, 2.0 g, 5.79 mmol), (R)-tert-butyl 3-aminopiperidine-1-carboxylate (1.160 g, 5.79 mmol, CNH technologies), and potassium carbonate (2.042 g, 7.38 mmol, Aldrich) were combined in THF (10.0 mL). The reaction was heated at 60° C. for 2 hrs. After 2 h, DMF (5.0 mL) was added. The reaction was heated at 90° C. for 14 h. The reaction mixture was cooled to 0° C. and 1N HCl was slowly added until pH was around 4. The resulting precipitate was filtered, washed with water and dried overnight to yield a light yellow solid (2.10 g, 75%).

MS (ES)(M+H)$^+$: 481 for $C_{21}H_{26}BrN_3O_5$.

Intermediate 30

(S)-ethyl 6-bromo-1-(1-(tert-butoxycarbonyl)piperidin-3-yl)-4-oxo-1,4-dihydro-1,8-naphthyridine-3-carboxylate

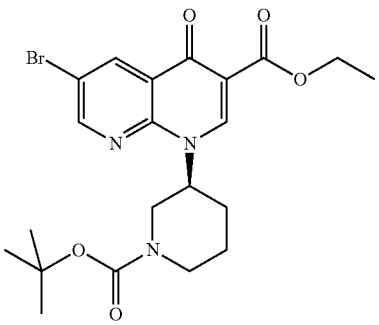 [SMILES: CCOC(=O)c1cn([C@H]2CCCN(C(=O)OC(C)(C)C)C2)c2ncc(Br)cc2c1=O]

Ethyl 2-(5-bromo-2-fluoronicotinoyl)-3-(dimethylamino)acrylate (Intermediate 3, 2.0 g, 5.79 mmol), (S)-tert-butyl 3-aminopiperidine-1-carboxylate (1.160 g, 5.79 mmol), and potassium carbonate (2.042 g, 7.38 mmol) were combined in DMF (10.0 mL). The reaction mixture was heated at 90° C. for 2 h. The reaction mixture was cooled to 0° C. and 1N HCl was slowly added until pH was 5. The resulting precipitate was collected by filtration, washed with water and dried overnight to yield a light yellow solid (2.10 g, 75%).

MS (ES)(M+H)$^+$: 481 for $C_{21}H_{26}BrN_3O_5$.

Intermediates 31-32

The following Intermediates were prepared by the procedure described for Intermediate 30 from the starting materials (SM) indicated.

| Int | Compound | Data | SM |
|---|---|---|---|
| 31 | (S)-ethyl 6-bromo-1-((1-ethylpyrrolidin-2-yl)methyl)-4-oxo-1,4-dihydro-1,8-naphthyridine-3-carboxylate | MS (ES) (M + H)$^+$: 409 for $C_{18}H_{22}BrN_3O_3$ $^1$H NMR (300 MHz) δ ppm 8.97 (s, 1 H), 8.81 (s, 1 H), 8.66 (s, 1 H), 4.41 (d, J = 5.27 Hz, 2 H), 4.25 (q, J = 7.28 Hz, 2 H), 3.06 (t, J = 6.78 Hz, 1 H), 2.81-2.98 (m, 2 H), 2.07-2.28 (m, 3 H), 1.70-1.85 (m, 1 H), 1.52-1.67 (m, 2 H), 1.44 (ddd, J = 7.72, 4.14, 3.96 Hz, 1 H), 1.28 (t, J = 7.16 Hz, 3 H), 0.89 (t, J = 7.16 Hz, 3 H). | Intermediate 3 & (S)-(1-ethylpyrrolidin-2-yl)methenamine |
| 32 | (R)-ethyl 6-bromo-1-((1-ethylpyrrolidin-2-yl)methyl)-4-oxo-1,4-dihydro-1,8-naphthyridine-3-carboxylate | MS (ES) (M + H)$^+$: 409 for $C_{18}H_{22}BrN_3O_3$ $^1$H NMR (300 MHz) δ ppm 8.98 (s, 1 H), 8.82 (s, 1 H), 8.65 (s, 1 H), 7.95 (s, 1 H), 4.42 (br. s., 2 H), 4.25 (q, J = 7.03 Hz, 2 H), 3.07 (br s., 1 H), 2.21 (br. s., 2 H), 1.78 (d, J = 9.80 Hz, 1 H), 1.39-1.70 (m, 3 H), 1.28 (t, J = 7.16 Hz, 3 H), 0.83-0.99 (m, 3 H) | Intermediate 3 and (R)-(1-ethylpyrrolidin-2-yl)methenamine |

Intermediate 33

(S)-ethyl 6-bromo-4-oxo-1-(piperidin-3-yl)-1,4-dihydro-1,8-naphthyridine-3-carboxylate

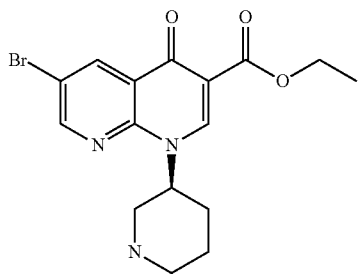 [SMILES: CCOC(=O)c1cn([C@H]2CCCNC2)c2ncc(Br)cc2c1=O]

(S)-ethyl 6-bromo-1-(1-(tert-butoxycarbonyl)piperidin-3-yl)-4-oxo-1,4-dihydro-1,8-naphthyridine-3-carboxylate (Intermediate 30, 10.847 g, 22.58 mmol) was taken up in dichloromethane (10 mL) and added HCl 4M in Dioxane (113 mL, 451.63 mmol) while stirring at RT for 1 h. The solvent was removed in vacuo and the residue was triturated with DCM, ether and EtOAc to give the desired product as a yellow solid. (S)-ethyl 6-bromo-4-oxo-1-(piperidin-3-yl)-1,4-dihydro-1,8-naphthyridine-3-carboxylate (8.50 g, 90%) was recovered as the HCl salt. MS (ES)(M+H)$^+$: 381 for $C_{16}H_{18}BrN_3O_3$. [HCl].

Intermediate 34

(S)-ethyl 6-bromo-1-(1-(2-morpholinoethyl)piperidin-3-yl)-4-oxo-1,4-dihydro-1,8-naphthyridine-3-carboxylate

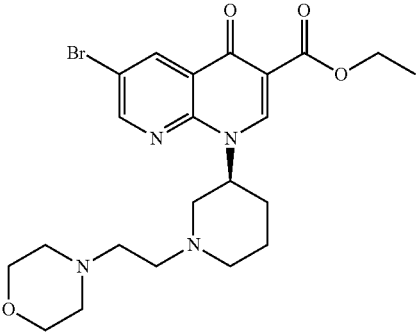 [SMILES: CCOC(=O)c1cn([C@H]2CCCN(CCN3CCOCC3)C2)c2ncc(Br)cc2c1=O]

(S)-ethyl 6-bromo-4-oxo-1-(piperidin-3-yl)-1,4-dihydro-1,8-naphthyridine-3-carboxylate hydrochloride Intermediate 33, 0.400 g, 0.96 mmol) and K$_2$CO$_3$ (0.663 g, 4.80 mmol) were taken up in acetonitrile (3 mL) and 4-(2-bromoethyl)morpholine hydrochloride (0.221 g, 0.96 mmol) added. The reaction mixture was heated to 120° C. in the microwave for 30 min. The reaction mixture was cooled to room temperature and filtered, and the inorganics were washed with EtOAc two times. The solvent was removed in vacuo. (S)-ethyl 6-bromo-1-(1-(2-morpholinoethyl)piperidin-3-yl)-4-oxo-1,4-dihydro-1,8-naphthyridine-3-carboxylate (0.420 g, 89%) was recovered as a tan solid and will be carried on without further purification. MS (ES)(M+H)$^+$: 494 for $C_{22}H_{29}BrN_4O_4$.

Intermediate 35

The following Intermediate was prepared by the procedure described for Intermediate 34 from the starting materials (SM) indicated.

| Int | Compound | Data | SM |
|---|---|---|---|
| 35 | (S)-ethyl 6-bromo-1-(2-(diethylamino)ethyl)piperidin-3-yl)-4-oxo-1,4-dihydro-1,8-naphthyridine-3-carboxylate | MS (ES) (M + H)$^+$: 480 for $C_{22}H_{31}BrN_4O_3$ | 2-chloro-N,N-diethylethanamine hydrochloride and Intermediate 33 |

Intermediate 36

S)-8-(1-(2-(diethylamino)ethyl)piperidin-3-yl)-6-(ethoxycarbonyl)-5-oxo-5,8-dihydro-1,8-naphthyridin-3-ylboronic acid

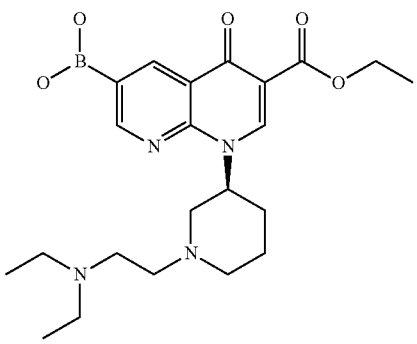 [SMILES: CCOC(=O)c1cn([C@H]2CCCN(CCN(CC)CC)C2)c2ncc(B(O)O)cc2c1=O]

(S)-ethyl 6-bromo-1-(1-(2-(diethylamino)ethyl)piperidin-3-yl)-4-oxo-1,4-dihydro-1,8-naphthyridine-3-carboxylate (Intermediate 35, 2.7 g, 5.63 mmol) and $PdCl_2(PPh_3)_2$ (0.395 g, 0.56 mmol) were combined and suspended in 1,4-dioxane (50 mL). The slurry was degassed, purged with nitrogen and then gently warmed to 75° C. for 20 min. 4,4,4',4',5,5,5',5'-Octamethyl-2,2'-bi(1,3,2-dioxaborolane) (4.29 g, 16.90 mmol) was then added in a single portion and the temperature was raised to 100° C. After an hour of heating, triethylamine (0.784 mL, 5.63 mmol) and potassium acetate (1.658 g, 16.90 mmol) were added sequentially. The reaction mixture was stirred at reflux overnight. The reaction mixture was cooled to room temperature and filtered through a celite. Solvent was removed in vacuo and the residue was purified via ISCO DCM/Methanol 0-20% gradient. (S)-8-(1-(2-(diethylamino)ethyl)piperidin-3-yl)-6-(ethoxycarbonyl)-5-oxo-5,8-dihydro-1,8-naphthyridin-3-ylboronic acid (2.0 g, 80%) was recovered as a brown solid.

MS (ES)(M+H)$^+$: 445 for $C_{22}H_{33}BN_4O_5$.

Intermediate 37

Ethyl 2-(2,6-difluoro-5-iodonicotinoyl)-3-(dimethylamino)acrylate

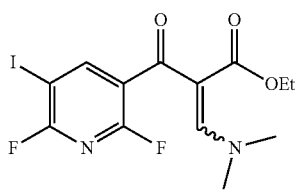 [SMILES: CCOC(=O)C(=CN(C)C)C(=O)c1cc(I)c(F)nc1F]

2,6-Difluoro-5-iodonicotinic acid (21 g, 73.69 mmol, from patent WO 2009/089263) was suspended in toluene (100 ml). Thionyl Chloride (26.9 ml, 368.44 mmol) and 1 ml of DMF were added and the mixture was heated at reflux for 1 h. The reaction mixture was concentrated in vacuo. The resulting residue was taken up in 10 mL of THF and triethylamine (15.41 ml, 110.53 mmol) was added followed by the addition of ethyl 3-(dimethylamino)acrylate (10.55 ml, 73.69 mmol) dropwise. The reaction mixture was stirred for 1 h at reflux. The reaction mixture was cooled down to room temperature and partitioned between water (50 mL) and ethyl acetate (50 mL). The aqueous layer was extracted with ethyl acetate (2×50 mL) and the organic layer was washed with 1N HCl (50 mL) and brine (50 mL), dried over sodium sulfate, and concentrated in vacuo. Purified via ISCO using EtOAc/Hexanes 10 to 100% gradient run, ethyl 2-(2,6-difluoro-5-iodonicotinoyl)-3-(dimethylamino)acrylate (14.4 g, 35.1 mmol, 47.6%) was recovered as a light pink solid.

MS (ES)(M+H)$^+$: 411 for $C_{13}H_{13}F_2IN_2O_3$.

$^1$H NMR δ □ ppm 8.47 (t, J=8.29 Hz, 1 H), 7.88 (s, 1 H), 3.93 (q, J=7.28 Hz, 2 H), 3.36 (br. s., 3 H), 2.81 (br. s., 3 H), 0.96 (t, J=7.16 Hz, 3 H).

Intermediate 38

(S)-ethyl 2-(2,6-difluoro-5-iodonicotinoyl)-3-((1-ethylpyrrolidin-2-yl)methylamino)acrylate

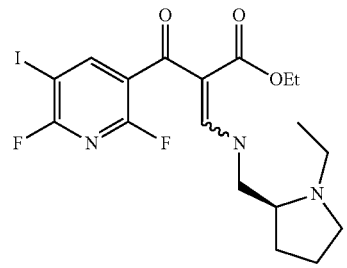 [SMILES: CCOC(=O)C(=CNC[C@@H]1CCCN1CC)C(=O)c1cc(I)c(F)nc1F]

Ethyl 2-(2,6-difluoro-5-iodonicotinoyl)-3-(dimethylamino)acrylate (Intermediate 37, 0.500 g, 1.10 mmol) was taken up THF (40 mL) and cooled to 0° C. for 10 min and then (S)-(1-ethylpyrrolidin-2-yl)methanamine (0.153 mL, 1.10 mmol) was added and stirred at room temperature for 2 min. The reaction mixture was quenched with sat $NH_4Cl$ diluted with EtOAc and separated, dried, and solvent removed. The residue was purified by a 0-5% gradient on the ISCO of DCM/Methanol to give (S)-ethyl 2-(2,6-difluoro-5-iodonicotinoyl)-3-((1-ethylpyrrolidin-2-yl)methylamino)acrylate (0.360 g, 67%) as a red oil.

MS (ES)(M+H)$^+$: 494 for $C_{18}H_{22}F_2IN_3O_3$.

Intermediate 39

The following Intermediate were prepared by the procedure described for Intermediate 38 from the starting materials (SM) indicated

| Int | Compound | Data | SM |
|---|---|---|---|
| 39 | ethyl 2-(2,6-difluoro-5-iodonicotinoyl)-3-(ethylamino)acrylate | MS (ES) (M + H)$^+$: 411 for $C_{13}H_{13}F_2IN_2O_3$ | Intermediate 37 and ethanamine |

Intermediate 40

(S)-ethyl 7-(2-(dimethylamino)ethylamino)-1-((1-ethylpyrrolidin-2-yl)methyl)-6-iodo-4-oxo-1,4-dihydro-1,8-naphthyridine-3-carboxylate

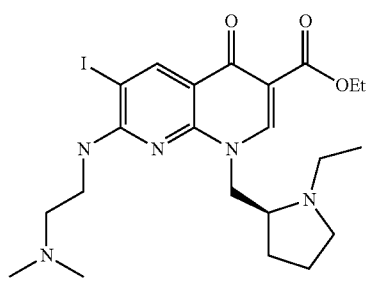 [SMILES: CCOC(=O)c1cn(C[C@@H]2CCCN2CC)c2nc(NCCN(C)C)c(I)cc2c1=O]

(S)-ethyl 2-(2,6-difluoro-5-iodonicotinoyl)-3-((1-ethylpyrrolidin-2-yl)methylamino)acrylate (Intermediate 38, 0.360 g, 0.73 mmol) was taken up in DMF (5 mL), $K_2CO_3$ (0.303 g, 2.19 mmol) was added and reaction mixture was heated to 90° C. for 15 min. The reaction mixture cooled to room temperature and $N^1,N^1$-dimethylethane-1,2-diamine (0.080 mL, 0.73 mmol) was added and stirred for 15 min. The reaction mixture was quenched with water and extracted with EtOAc 3 times. The combined organics were washed with brine two times, dried over $Mg_2SO_4$, and the solvent removed. Crude product was carried on without purification.

MS (ES)(M+H)$^+$: 542 for $C_{22}H_{32}IN_5O_3$.

Intermediate 41-42

The following Intermediates were prepared by the procedure described for Intermediate 40 from the starting materials (SM) indicated.

| Int | Compound | Data | SM |
|---|---|---|---|
| 41 | ethyl 7-(2-(dimethylamino)ethylamino)-1-ethyl-6-iodo-4-oxo-1,4-dihydro-1,8-napthyridine-3-carboxylate | MS (ES) (M + H)$^+$: 459 for $C_{17}H_{23}IN_4O_3$ | Intermediate 39 and N1,N1-dimethylethane-1,2-diamine |
| 42 | ethyl 1-ethyl-6-iodo-7-(4-methylpiperazin-1-yl)-4-oxo-1,4-dihydro-1,8-napthyridine-3-carboxylate | MS (ES) (M + H)$^+$: 471 for $C_{18}H_{23}IN_4O_3$ | Intermediate 39 and 1-methylpiperazine |

Intermediate 43

(S)-7-(2-(dimethylamino)ethylamino)-1-((1-ethylpyrrolidin-2-yl)methyl)-6-iodo-4-oxo-1,4-dihydro-1,8-naphthyridine-3-carboxylic acid

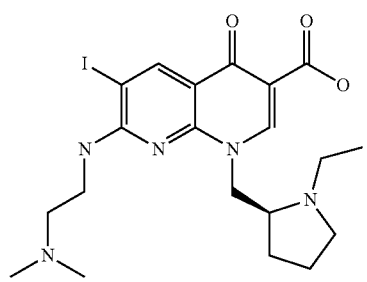 [SMILES: CCN1CCC[C@H]1Cn1cc(C(=O)O)c(=O)c2cc(I)c(NCCN(C)C)nc21]

(S)-ethyl 7-(2-(dimethylamino)ethylamino)-1-((1-ethylpyrrolidin-2-yl)methyl)-6-iodo-4-oxo-1,4-dihydro-1,8-naphthyridine-3-carboxylate (Intermediate 40) was then taken up in methanol (2 mL) and THF (5 mL) and 1 ml of 2N LiOH was added and stirred at room temperature for 30 min. The solvent was removed in vacuo to give (S)-7-(2-(dimethylamino)ethylamino)-1-((1-ethylpyrrolidin-2-yl)methyl)-6-iodo-4-oxo-1,4-dihydro-1,8-naphthyridine-3-carboxylic acid as a light brown solid, material, which will be carried forward without further purification.

MS (ES)(M+H)$^+$: 514 for $C_{20}H_{28}IN_5O_3$.

Intermediate 44-45

The following Intermediates were prepared by the procedure described for Intermediate 43 from the starting materials (SM) indicated

| Int | Compound | Data | SM |
|---|---|---|---|
| 44 | 7-(2-(dimethylamino)ethylamino)-1-ethyl-6-iodo-4-oxo-1,4-dihydro-1,8-napthyridine-3-carboxylic acid 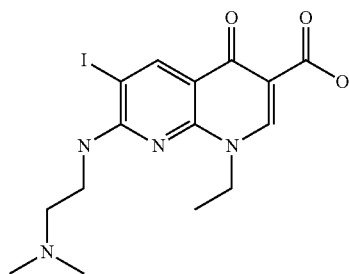 | MS (ES) (M + H)$^+$: 431 for $C_{15}H_{19}IN_4O_3$ | Intermediate 41 |
| 45 | 1-ethyl-6-iodo-7-(4-methylpiperazin-1-yl)-4-oxo-1,4-dihydro-1,8-napthyridine-3-carboxylic acid 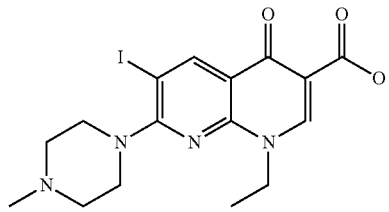 | MS (ES) (M + H)$^+$: 443 for $C_{16}H_{19}IN_4O_3$ | Intermediate 42 |

Intermediate 46

1-(5-bromo-4-(4-isobutylthiazol-2-yl)pyridin-2-yl)-3-ethylurea

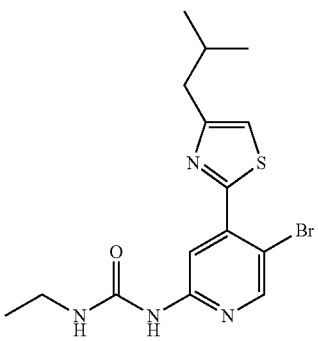 [SMILES: CCNC(=O)Nc1cc(-c2nc(CC(C)C)cs2)c(Br)cn1]

In a 100 mL round-bottomed flask 5-bromo-2-(3-ethylureido)pyridine-4-carbothioamide (Intermediate 6, 0.95 g, 3.13 mmol) and 1-bromo-4-methylpentan-2-one (0.561 g, 3.13 mmol, *Chem. Pharm. Bull.*, 2001, 49(8), 988-998) were mixed in EtOH (10 mL) to give a yellow suspension. The reaction mixture was heated to 80° C. for 3 h. The reaction mixture was cooled to room temperature, and concentrated under reduced pressure. ACN was added, and the residue solid was azeotroped with ACN (3×). The crude mass obtained, 1.02 g, was taken forward without purification.

LC/MS (ES$^+$)[(M+FI)$^+$]: 383, 385 for $C_{14}H_{15}BrN_4OS$.

$^1$H NMR (300 MHz, d$_6$-DMSO): 0.94 (d, 6H), 1.08 (t, 3H), 2.07 (m, 1H), 2.68 (m, 2H), 3.17 (m, 2H), 7.32 (m, 1H), 7.64 (s, 1H), 8.35 (s, 1H), 8.49 (s, 1H), 9.30 (s, 1H).

Intermediate 47

Ethyl 6-bromo-1-cyclohexyl-4-oxo-1,4-dihydro-1,7-naphthyridine-3-carboxylate

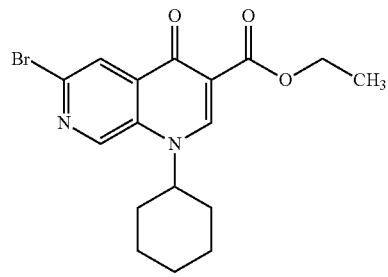 [SMILES: CCOC(=O)c1cn(C2CCCCC2)c2cnc(Br)cc2c1=O]

To a solution of ethyl 2-(2-bromo-5-fluoroisonicotinoyl)-3-(dimethylamino)acrylate (Intermediate 66, 1.14 g, 3.29 mmol, 1 equiv.) in DMF (6.5 mL) was added cyclohexanamine (592 mg, 3.29 mmol, 1 equiv.). This reaction mixture was stirred at 70° C. for 30 min. Potassium carbonate (1.36 g, 9.86 mmol, 3 equiv.) was added and stirred at 70° C. for 2 h. The reaction mixture was cooled to room temperature and quenched with water (2 mL). 1 N HCl was added until pH 4-5 was reached. The precipitate was washed with water and hexanes and dried to provide ethyl 6-bromo-1-cyclohexyl-4-oxo-1,4-dihydro-1,7-naphthyridine-3-carboxylate (1.15 g, 92%).

Calcd for $C_{17}H_{19}BrN_2O_3$.

NMR (d$_6$-DMSO) δ 9.32 (s, 1H), 8.66 (s, 1H), 8.17 (s, 1H), 4.85-4.80 (m, 1H), 4.29-4.22 (m, 2H), 2.08-2.03 (m, 2H), 1.87-1.45 (m, 8H), 1.29 (t, 3H).

Intermediates 48-55

The following intermediates were prepared by the procedure described in Intermediate 47 from the indicated starting material

| Int | Compound | Data | SM |
|---|---|---|---|
| 48 | ethyl 6-bromo-1-(3,3-dimethylbutyl)-4-oxo-1,4-dihydro-1,7-naphthyridine-3-carboxylate | Calcd for $C_{17}H_{21}BrN_2O_3$ [M + H]$^+$: 383.08. | Intermediate 66 & 3,3-dimethylbutan-1-amine |

| Int | Compound | Data | SM |
|---|---|---|---|
| 49 | (R)-ethyl 6-bromo-1-((1-ethylpyrrolidin-2-yl)methyl)-4-oxo-1,4-dihydro-1,7-naphthyridine-3-carboxylate | Calcd for $C_{18}H_{22}BrN_3O_3$ [M + H]$^+$: 410.01. $H^1$NMR (d$_6$-DMSO) δ 9.21 (s, 1H), 9.03 (s, 1H), 8.17 (s, 1H), 5.17-5.09 (m, 1H), 4.94-4.87 (m, 1H), 4.29-4.22 (m, 2H), 4.03-3.94 (m, 1H), 3.70-3.59 (m, 1H), 3.26-3.12 (m, 4H), 2.13-1.76 (m, 5H), 1.30 (t, 3H), 1.21 (t, 3H). | Intermediate 66 & (R)-(1-ethylpyrrolidin-2-yl)methanamine |
| 50 | (S)-ethyl 6-bromo-1-((1-ethylpyrrolidin-2-yl)methyl)-4-oxo-1,4-dihydro-1,7-naphthyridine-3-carboxylate | Calcd for $C_{18}H_{22}BrN_3O_3$ [M + H]$^+$: 409.98. $H^1$NMR (d$_6$-DMSO) δ 9.21 (s, 1H), 9.03 (s, 1H), 8.17 (s, 1H), 5.16-5.09 (m, 1H), 4.94-4.87 (m, 1H), 4.29-4.22 (m, 2H), 4.02-3.94 (m, 1H), 3.70-3.58 (m, 1H), 3.26-3.03 (m, 4H), 2.15-1.76 (m, 5H), 1.30 (t, 3H), 1.21 (t, 3H) | Intermediate 66 & (S)-(1-ethylpyrrolidin-2-yl)methanamine |
| 51 | ethyl 6-bromo-1-(2-(morpholinopropyl)-4-oxo-1,4-dihydro-1,7-naphthyridine-3-carboxylate | Calcd for $C_{18}H_{22}BrN_3O_4$ [M + H]$^+$: 426.00. $H^1$NMR (d$_6$-DMSO) δ 9.19 (s, 1H), 8.59 (s, 1H), 8.15 (s, 1H), 4.54-4.48 (m, 1H), 4.33-4.19 (m, 3H), 3.48-3.37 (m, 3H), 2.92-2.83 (m, 1H), 2.75-2.68 (m, 2H), 2.20-2.14 (m, 2H), 1.28 (t, 3H), 1.05 (d, 3H) | Intermediate 66 & 2-morpholinopropan-1-amine |
| 52 | ethyl 6-bromo-1-((1-methyl-1H-pyrazol-4-yl)methyl)-4-oxo-1,4-dihydro-1,7-naphthyridine-3-carboxylate | Calcd for $C_{16}H_{15}BrN_4O_3$ $H^1$NMR (d$_6$-DMSO) δ 9.18 (s, 1H), 8.92 (s, 1H), 8.14 (s, 1H), 7.80 (s, 1H), 7.53 (s, 1H), 5.56 (s, 2H), 4.29-4.22 (m, 2H), 3.76 (s, 3H), 1.29 (t, 3H) | Intermediate 66 & (1-methyl-1H-pyrazol-4-yl)methanamine |

-continued

| Int | Compound | Data | SM |
|---|---|---|---|
| 53 | ethyl 6-bromo-1-((1-methyl-1H-imidazol-4-yl)methyl)-4-oxo-1,4-dihydro-1,7-naphthyridine-3-carboxylate 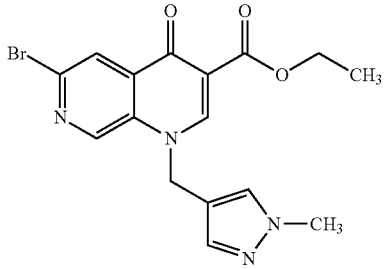 | Calcd for $C_{16}H_{15}BrN_4O_3$ [M + H]$^+$: 392.98. H$^1$NMR (d$_6$-DMSO) δ 9.29 (s, 1H), 8.90 (s, 1H), 8.12 (s, 1H), 7.53 (s, 1H), 7.32 (s, 1H), 5.55 (s, 2H), 4.29-4.22 (m, 2H), 3.6 (s, 3H), 1.29 (t, 3H) | Intermediate 66 & (1-methyl-1H-imidazol-4-yl)methanamine |
| 54 | (S)-ethyl 6-bromo-1-(1-tert-butoxycarbonyl)piperidin-3-yl)-4-oxo-1,4-dihydro-1,7-naphthyridine-3-carboxylate 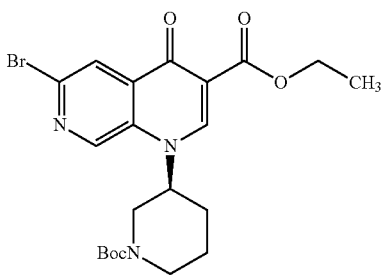 | Calcd for $C_{21}H_{26}BrN_3O_5$ [M + H]$^+$: 482.02 | Intermediate 66 & (S)-tert-butyl 3-aminopiperidine-1-carboxylate |
| 55 | (R)-ethyl 6-bromo-1-(1-tert-butoxycarbonyl)piperidin-3-yl)-4-oxo-1,4-dihydro-1,7-naphthyridine-3-carboxylate 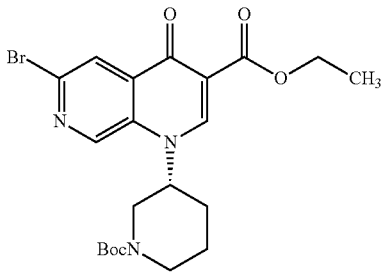 | Calcd for $C_{21}H_{26}BrN_3O_5$ [M + H]$^+$: 482.04 | Intermediate 66 & (R)-tert-butyl 3-aminopiperidine-1-carboxylate |

Intermediate 56

Ethyl 6-bromo-1-(1,3-dimethoxypropan-2-yl)-4-oxo-1,4-dihydro-1,7-naphthyridine-3-carboxylate

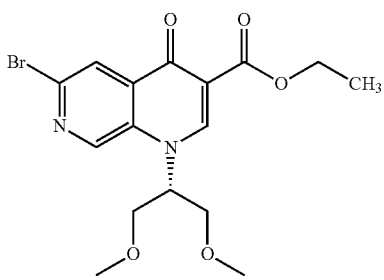

To a solution of ethyl 2-(2-bromo-5-fluoroisonicotinoyl)-3-(dimethylamino)acrylate (Intermediate 65, 1 g, 2.9 mmol, 1 equiv.) in THF (7 mL) was added 1,3-dimethoxypropan-2-amine (451 mL, 2.9 mmol, 1 equiv.). This reaction mixture was stirred at 60° C. for 1 h. The reaction mixture was concentrated under reduced pressure and re-suspended in DMF (7 mL). Potassium carbonate (1.2 g, 8.69 mmol, 3 equiv.) was added, and the reaction mixture was stirred at 70° C. for 3 h. The reaction mixture was cooled to room temperature and quenched with water. 1 N HCl was added until pH 4-5 was reached. The precipitate was washed with water and hexanes and dried to provide ethyl 6-bromo-1-(1,3-dimethoxypropan-2-yl)-4-oxo-1,4-dihydro-1,7-naphthyridine-3-carboxylate as a solid (963 mg, 83%).

Calcd for $C_{16}H_{19}BrN_2O_5$.

NMR (d$_6$-DMSO) δ 9.33 (s, 1H), 8.81 (s, 1H), 8.04 (s, 1H), 5.52-5.42 (m, 1H), 4.28-4.21 (m, 2H), 3.91-3.79 (m, 4H), 3.26 (s, 6H), 1.29 (t, 3H).

Intermediates 57-59

The following intermediates were prepared by the procedure described in Intermediate 56 from the indicated starting material.

| Int | Compound | Data | SM |
|---|---|---|---|
| 57 | (S)-ethyl 6-bromo-1-(1-hydroxy-4-methylpentan-2-yl)-4-oxo-1,4-dihydro-1,7-naphthyridine-3-carboxylate | Calcd for $C_{17}H_{21}BrN_2O_4$ [M + H]$^+$: 398.88. $H^1$NMR ($d_6$-DMSO) δ 9.40 (s, 1H), 8.67 (s, 1H), 8.05 (s, 1H), 5.17-5.14 (m, 2H), 4.29-4.22 (m, 2H), 3.79-3.73 (m, 2H), 1.98-1.74 (m, 2H), 1.52-1.46 (m, 1H), 1.28 (t, 3H), 0.92 (d, 3H), 0.88 (d, 3H) | Intermediate 66 & (S)-2-amino-4-methylpentan-1-ol |
| 58 | ethyl 6-bromo-1-(2-methoxyethyl)-4-oxo-1,4-dihydro-1,7-naphthyridine-3-carboxylate | Calcd for $C_{14}H_{15}BrN_2O_4$ [M + H]$^+$: 398.88. $H^1$NMR ($d_6$-DMSO) δ 9.40 (s, 1H), 8.67 (s, 1H), 8.05 (s, 1H), 5.17-5.14 (m, 2H), 4.29-4.22 (m, 2H), 3.79-3.73 (m, 2H), 1.98-1.74 (m, 2H), 1.52-1.46 (m, 1H), 1.28 (t, 3H), 0.92 (d, 3H), 0.88 (d, 3H) | Intermediate 66 & 2-methoxyethanamine |
| 59 | ethyl 6-bromo-1-(2-dimethylamino)ethyl)-4-oxo-1,4-dihydro-1,7-naphthyridine-3-carboxylate | Calcd for $C_{15}H_{18}BrN_3O_3$ $H^1$NMR ($d_6$-DMSO) δ 9.25 (s, 1H), 8.84 (s, 1H), 8.15 (s, 1H), 4.91-4.87 (m, 2H), 4.29-4.22 (m, 2H), 3.62-3.49 (m, 2H), 2.85 (s, 6H), 1.29 (t, 3H) | Intermediate 66 & N,N-dimethylethane-1,2-diamine |

Intermediate 60

(S)-ethyl 6-bromo-1-(1-(2-morpholinoethyl)piperidin-3-yl)-4-oxo-1,4-dihydro-1,7-naphthyridine-3-carboxylate

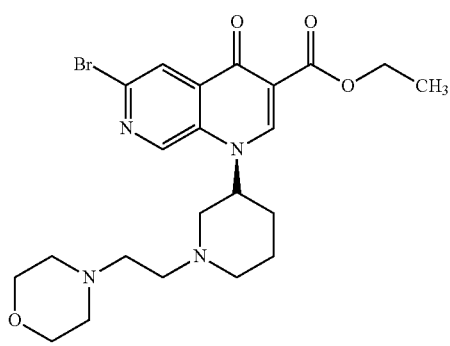

To a suspension of (S)-ethyl 6-bromo-4-oxo-1-(piperidin-3-yl)-1,4-dihydro-1,7-naphthyridine-3-carboxylate hydrochloride (Intermediate 62, 1 g, 2.4 mmol, 1 equiv.) in acetonitrile (6 mL) was added 4-(2-chloroethyl)morpholine hydrochloride (447 mg, 2.4 mmol, 1 equiv.) followed by sodium iodide (360 mg, 2.4 mmol, 1 equiv.) and potassium carbonate (1.66 g, 12 mmol, 5 equiv.). This was stirred in the microwave at 120° C. for 30 min. The reaction was cooled to room temperature and diluted with ethyl acetate. The precipitates were removed, and the filtrate was concentrated to provide (S)-ethyl 6-bromo-1-(1-(2-morpholinoethyl)piperidin-3-yl)-4-oxo-1,4-dihydro-1,7-naphthyridine-3-carboxylate as a solid (501.3 mg, 43%). Calcd for $C_{22}H_{29}BrN_4O_4$ $[M+H]^+$: 495.07.

Intermediate 61

The following intermediate was prepared by the procedure described in Intermediate 60 from the indicated starting material.

Intermediate 62

(S)-ethyl 6-bromo-4-oxo-1-(piperidin-3-yl)-1,4-dihydro-1,7-naphthyridine-3-carboxylate hydrochloride

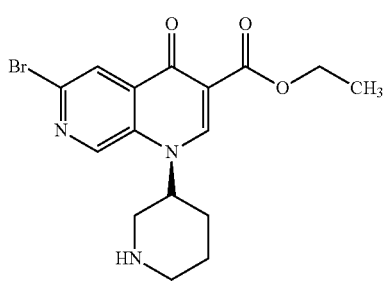

To a solution of (S)-ethyl 6-bromo-1-(1-(tert-butoxycarbonyl)piperidin-3-yl)-4-oxo-1,4-dihydro-1,7-naphthyridine-3-carboxylate (Intermediate 54, 6.37 g, 13.26 mmol, 1 equiv.) in dichloromethane (53 mL) was added 4 N hydrogen chloride (13.26 mL, 53.04 mmol, 4 equiv.). This was stirred at room temperature for 8 h. The precipitate was washed with diethyl ether and dried to provide (S)-ethyl 6-bromo-4-oxo-1-(piperidin-3-yl)-1,4-dihydro-1,7-naphthyridine-3-carboxylate hydrochloride as a solid (4.67 g, >99%).

Calcd for $C_{22}H_{29}BrN_4O_4$.

NMR ($d_6$-DMSO) δ 9.46 (s, 1H), 9.45 (s, 1H), 8.7 (s, 1H), 8.17 (s, 1H), 8.05 (s, 1H), 5.36-3.30 (m, 1H), 4.31-4.22 (m, 2H), 3.77-3.63 (m, 2H), 3.42-3.35 (m, 2H), 2.34-2.06 (m, 4H), 1.28 (t, 3H).

Intermediate 63

The following intermediate was prepared by the procedure described in Intermediate 60 from the indicated starting material.

| Int | Compound | Data | SM |
|---|---|---|---|
| 61 | (R)-ethyl 6-bromo-1-(1-(2-morpholinoethyl)piperidin-3-yl)-4-oxo-1,4-dihydro-1,7-naphthyridine-3-carboxylate | Calcd for $C_{22}H_{29}BrN_4O_4$ $[M + H]^+$: 494.98 | Intermediate 63 |

| Int | Compound | Data | SM |
|---|---|---|---|
| 63 | (R)-ethyl 6-bromo-4-oxo-1-(piperidin-3-yl)-1,4-dihydro-1,7-naphthyridine-3-carboxylate hydrochloride<br>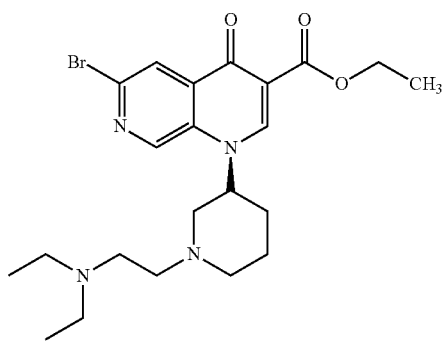 | Calcd for $C_{22}H_{29}BrN_4O_4$. $H^1$NMR ($d_6$-DMSO) δ 9.44 (s, 1H), 9.42 (s, 1H), 8.7 (s, 1H), 8.17 (s, 1H), 8.05 (s, 1H), 5.36-3.30 (m, 1H), 4.31-4.22 (m, 2H), 3.77-3.63 (m, 2H), 3.42-3.35 (m, 2H), 2.34-2.06 (m, 4H), 1.30 (t, 3H) | Intermediate 55 |

Intermediate 64

(S)-ethyl 6-bromo-1-(1-(2-(diethylamino)ethyl)piperidin-3-yl)-4-oxo-1,4-dihydro-1,7-naphthyridine-3-carboxylate To a suspension of (S)-ethyl 6-bromo-4-oxo-1-(piperidin-3-yl)-1,4-dihydro-1,7-naphthyridine-3-carboxylate hydrochloride (Intermediate 62, 610 mg, 1.46 mmol, 1 equiv.) in acetonitrile (4 mL) was added 2-chloro-N,N-diethylethanamine hydrochloride (252 mg, 1.46 mmol, 1 equiv.) followed by potassium carbonate (1 g, 7.32 mmol, 5 equiv.). This was stirred in the microwave at 120° C. for 30 min. The reaction was cooled to room temperature and diluted with ethyl acetate. The precipitate was discarded, and the filtrate was concentrated to provide (S)-ethyl 6-bromo-1-(1-(2-(diethylamino)ethyl)piperidin-3-yl)-4-oxo-1,4-dihydro-1,7-naphthyridine-3-carboxylate as a solid (mg, %).

Calcd for $C_{22}H_{31}BrN_4O_3$ [M+H]$^+$: 481.04.

Intermediate 65

The following intermediate was prepared by the procedure described in Intermediate 62 with the indicated starting material.

| Int | Compound | Data | SM |
|---|---|---|---|
| 65 | (R)-ethyl 6-bromo-1-(1-(2-(diethylamino)ethyl)piperidin-3-yl)-4-oxo-1,4-dihydro-1,7-naphthyridine-3-carboxylate | Calcd for $C_{22}H_{31}BrN_4O_3$ [M + H]$^+$: 481.11 | Intermediate 62 |

Intermediate 66 ethyl 2-(2-bromo-5-fluoroisonicotinoyl)-3-(dimethylamino)acrylate

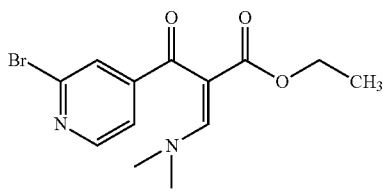 [SMILES: CCOC(=O)/C(=C/N(C)C)C(=O)c1ccnc(Br)c1]

To a solution of 2-bromo-5-fluoroisonicotinic acid (25 g, 113.64 mmol, 1 equiv.) in toluene (251 mL) was added thionyl chloride (41.5 mL, 568.19 mmol, 5 equiv.). The reaction was stirred at 110° C. for 4 h. The reaction was cooled to room temperature and concentrated. The residue was re-suspended in THF (100 mL) and added drop-wise to a solution of ethyl 3-(dimethylamino)acrylate (16.3 mL, 113.64 mmol, 1 equiv.) and triethylamine (23.8 mL, 170.46 mmol, 1.5 equiv.) in THF (151 mL). The reaction was stirred at 70° C. for 5 h. The reaction was cooled to room temperature and diluted with water. The reaction was partitioned between water (300 mL) and ethyl acetate (300 mL). The aqueous layer was extracted with ethyl acetate (2×300 mL), and the organics were washed with 1 N HCl (300 mL) and saturated brine (300 mL), dried over sodium sulfate, and concentrated. The compound was purified (silica gel chromatography) and concentrated to provide ethyl 2-(2-bromo-5-fluoroisonicotinoyl)-3-(dimethylamino)acrylate as a solid (28.6 g, 73%). Calcd for $C_{13}H_{14}BrFN_2O_3$ [M+H]$^+$: 346.90.

NMR (d$_6$-DMSO) δ 8.44 (s, 1H), 7.94 (s, 1H), 7.61 (d, 1H), 3.93-3.86 (m, 2H), 3.40 (s, 3H), 2.88 (s, 3H), 0.92 (t, 3H).

Intermediate 67

The following intermediate was prepared according to the procedure described for Example 28 from the starting materials indicated.

| Int | Compound | Data | SM |
|---|---|---|---|
| 67 | | Calcd for $C_{34}H_{41}F_3N_8O_4S$ [M + H]$^+$: 714 | Example 27 and 2-chloro-N,N-dimethylethanamine |

(R)-ethyl 1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydro-1,8-naphthyridine-3-carboxylate

Intermediates 68-70

The following intermediate was prepared according to the procedure described for Intermediate 1 from the indicated starting material.

| Int | Compound | Data | SM |
|---|---|---|---|
| 68 | ethyl 6-bromo-1-(2-morpholinoethyl)-4-oxo-1,4-dihydro-1,8-naphthyridine-3-carboxylate | Calcd for $C_{17}H_{20}BrN_3O_4$ $[M + H]^+$: 410 | Intermediate 3 & 2-morpholinoethanamine |
| 69 | ethyl 6-bromo-1-(1,3-dimethoxypropan-2-yl)-4-oxo-1,4-dihydro-1,8-naphthyridine-3-carboxylate | Calcd for $C_{16}H_{19}BrN_2O_5$ $[M + H]^+$: 400 | Intermediate 3 & 1,3-dimethoxypropan-2-amine |
| 70 | ethyl 6-bromo-1-(1-methylazetidin-3-yl)-4-oxo-1,4-dihydro-1,8-naphthyridine-3-carboxylate | Calcd for $C_{15}H_{16}BrN_3O_3$ $[M + H]^+$: 366 | Intermediate 3 & 1-methylazetidin-3-amine |

Intermediates 71-73

The following intermediate was prepared according to the procedure described for Example 5 from the indicated starting materials.

| Int | Compound | Data | SM |
|---|---|---|---|
| 71 | ethyl 6-(6-(3-ethylureido)-4-(4-(trifluoromethyl)thiazol-2-yl)pyridin-3-yl)-1-(1-methylazetidin-3-yl)-4-oxo-1,4-dihydro-1,8-naphthyridine-3-carboxylate | Calcd for $C_{27}H_{26}F_3N_7O_4S$ [M + H]$^+$: 602 | Intermediate 9 and Intermediate 70 |
| 72 | ethyl 6-(6-(3-ethylureido)-4-(4-(trifluoromethyl)thiazol-2-yl)pyridin-3-yl)-1-(2-morpholinoethyl)-4-oxo-1,4-dihydro-1,8-naphthyridine-3-carboxylate | Calcd for $C_{29}H_{30}F_3N_7O_5S$ [M + H]$^+$: 646 | Intermediate 9 and Intermediate 68 |
| Int 73 | ethyl 1-(1,3-dimethoxypropan-2-yl)-6-(6-(3-ethylureido)-4-(4-(trifluoromethyl)thiazol-2-yl)pyridin-3-yl)-4-oxo-1,4-dihydro-1,8-naphthyridine-3-carboxylate | Calcd for $C_{28}H_{29}F_3N_6O_6S$ [M + H]$^+$: 635 | Intermediate 9 and Intermediate 69 |

Intermediate 74

The following Intermediates were prepared by the procedure described for Intermediate 40 from the starting materials (SM) indicated.

| Int | Compound | Data | SM |
|---|---|---|---|
| 74 | (S)-ethyl 1-((1-ethylpyrrolidin-2-yl)methyl)-6-iodo-7-(4-methylpiperazin-1-yl)-4-oxo-1,4-dihydro-1,8-naphthyridine-3-carboxylate | Calcd for $C_{23}H_{32}IN_5O_3$ $[M + H]^+$: 554 | Intermediate 38 and 1-methylpiperazine |

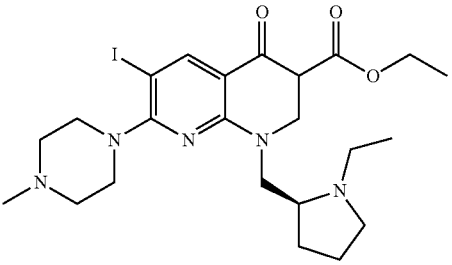

Intermediate 75

The following Intermediates were prepared by the procedure described for Intermediate 43 from the starting materials (SM) indicated.

| Int | Compound | Data | SM |
|---|---|---|---|
| 75 | (S)-1-((1-ethylpyrrolidin-2-yl)methyl)-6-iodo-7-(4-methylpiperazin-1-yl)-4-oxo-1,4-dihydro-1,8-naphthyridine-3-carboxylic acid | Calcd for $C_{21}H_{28}IN_5O_3$ $[M + H]^+$: 526 | Intermediate 74 |

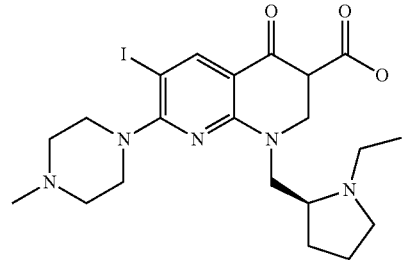

Intermediate 76

(S)-6-(6-(3-ethylureido)-4-(4-(trifluoromethyl)thiazol-2-yl)pyridin-3-yl)-7-fluoro-1-(1-hydroxy-3,3-dimethylbutan-2-yl)-4-oxo-1,4-dihydro-1,8-naphthyridine-3-carboxylic acid

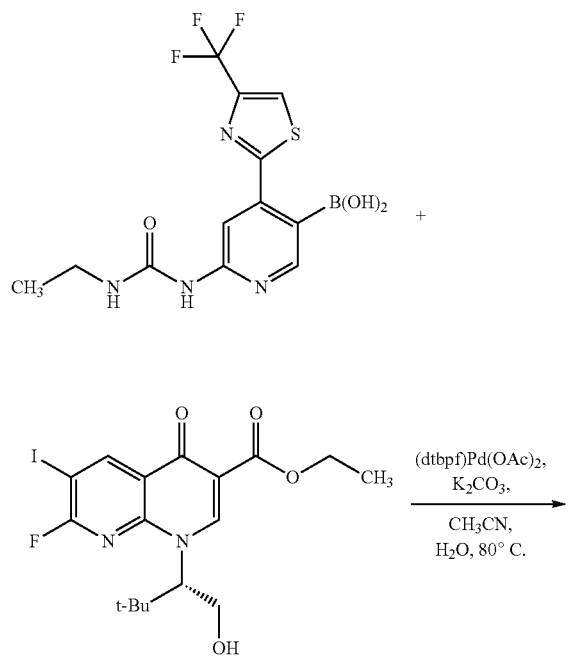

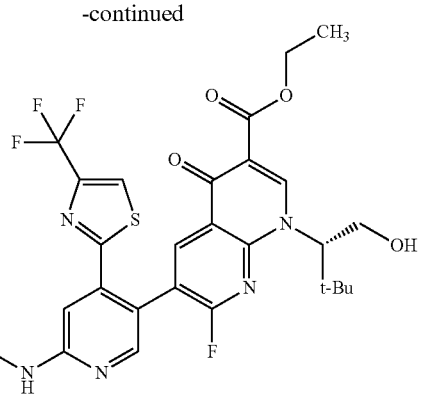

To a solution of palladium (II) acetate (0.163 g, 0.72 mmol, 0.1 equiv.) and 1,1'-bis(di-tert-butylphosphino)ferrocene (0.344 g, 0.72 mmol, 0.1 equiv.) in acetonitrile (27 mL) was added (S)-ethyl 7-fluoro-1-(1-hydroxy-3,3-dimethylbutan-2-yl)-6-iodo-4-oxo-1,4-dihydro-1,8-naphthyridine-3-carboxylate Intermediate 78 (3.35 g, 7.25 mmol, 1 equiv.) and 6-(3-ethylureido)-4-(4-(trifluoromethyl)thiazole-2-yl)pyridine-3-ylboronic acid Intermediate 9 (2.64 g, 7.32 mmol, 1.01 equiv.) and a solution of potassium carbonate (1.5 g, 10.87 mmol, 1.5 equiv.) in water (9 mL). This was stirred at 80° C. for 2 h. The reaction was cooled to room temperature and diluted with water. The precipitate was washed with water and dried. The compound was purified via silica gel chromatography and concentrated to afford (S)-6-(6-(3-ethylureido)-4-(4-(trifluoromethyl)thiazol-2-yl)pyridin-3-yl)-7-fluoro-1-(1-hydroxy-3,3-dimethylbutan-2-yl)-4-oxo-1,4-dihydro-1,8-naphthyridine-3-carboxylic acid Intermediate 76 (1.2 g, 25%). Calcd for $C_{29}H_{30}F_4N_6O_5S$ $[M+H]^+$: 651.2.

Intermediate 77

The following intermediate was prepared by the procedure described in Intermediate 76 from the indicated starting material.

| Int | Compound | Data | SM |
|---|---|---|---|
| 77 | ethyl 6-(6-(3-ethylureido)-4-(4-(trifluoromethyl)thiazol-2-yl)pyridin-3-yl)-7-fluoro-1-(2-(4-methylpiperazin-1-yl)ethyl)-4-oxo-1,4-dihydro-1,8-naphthyridine-3-carboxylate | Calcd for $C_{30}H_{32}F_4N_8O_4S$ $[M + H]^+$: 677.2. $H^1NMR$ ($d_6$-DMSO) δ 9.53 (s, 1H), 8.77 (s, 1H), 8.64 (d, 1H), 8.6 (d, 1H), 8.41 (s, 1H), 8.28 (s, 1H), 7.52 (t, 1H), 4.52-4.45 (m, 2H), 4.34-4.24 (m, 2H), 3.26-3.17 (m, 2H), 2.71-2.65 (m, 6H), 2.6 (s, 3H), 2.45-2.43 (m, 4H), 1.31 (t, 3H), 1.12 (t, 3H). | Intermediate 79 and Intermediate 9 |

Intermediate 78

(5)-ethyl 7-fluoro-1-(1-hydroxy-3,3-dimethylbutan-2-yl)-6-iodo-4-oxo-1,4-dihydro-1,8-naphthyridine-3-carboxylate

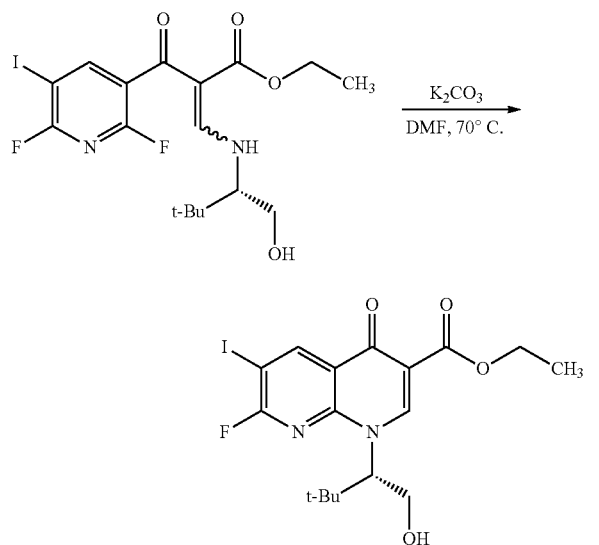

To a solution of (5)-ethyl 2-(2,6-difluoro-5-iodonicotinoyl)-3-(1-hydroxy-3,3-dimethylbutan-2-ylamino)acrylate Intermediate 80 (4.47 g, 9.27 mmol, 1 equiv.) in DMF (46 mL) was added potassium carbonate (1.92 g, 13.9 mmol, 1.5 equiv.) was added, and the reaction was stirred at 70° C. for 30 min. The reaction was cooled to 0° C. and quenched with saturated ammonium chloride (5 mL). The reaction was partitioned between water (50 mL) and dichloromethane (50 mL). The aqueous layer was extracted with dichloromethane (2×30 mL), and the organics were concentrated. The compound was purified via silica gel chromatography and concentrated to afford (S)-ethyl 7-fluoro-1-(1-hydroxy-3,3-dimethylbutan-2-yl)-6-iodo-4-oxo-1,4-dihydro-1,8-naphthyridine-3-carboxylate Intermediate 78 as a solid (3.37 g, 79%). Calcd for $C_{17}H_{26}FIN_2O_4$. $H^1$NMR ($d_6$-DMSO) δ 8.69 (s, 1H), 4.24 (m, 3H), 3.98 (m, 2H), 1.28 (t, 3H), 0.95 (s, 9H).

Intermediate 79

The following intermediate was prepared by the procedure described in Intermediate 78 from the indicated starting material.

| Int | Compound | Data | SM |
|---|---|---|---|
| 79 | ethyl 7-fluoro-6-iodo-1-(2-(4-methylpiperazin-1-yl)ethyl-4-oxo-1,4-dihydro-1,8-naphthyridine-3-carboxylate | Calcd for $C_{18}H_{22}FIN_4O_3$ $H^1$NMR ($d_6$-DMSO) δ 9.72 (s, 1H), 8.65 (s, 1H), 8.64 (d, 1H), 4.5-4.4 (m, 2H), 4.27-4.2 (m, 2H), 2.72.6 (m, 2H), 2.45 (m, 4H), 2.27 (m, 3H), 1.29 (t, 3H). | Intermediate 81 |

Intermediate 80

(S)-ethyl 2-(2,6-difluoro-5-iodonicotinoyl)-3-(1-hydroxy-3,3-dimethylbutan-2-ylamino)acrylate

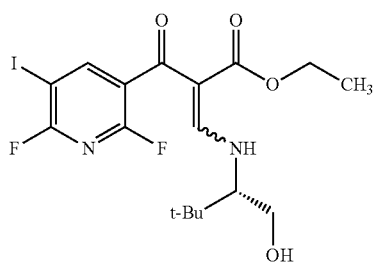 [SMILES: CCOC(=O)C(=CN[C@H](CO)C(C)(C)C)C(=O)c1cc(I)c(F)nc1F]

To a solution of 2,6-difluoro-5-iodonicotinic acid (4 g, 14.04 mmol, 1 equiv.) in toluene (30 mL) was added thionyl chloride (5.12 mL, 70.18 mmol, 5 equiv.) followed by DMF (0.5 mL). The reaction was stirred at 110° C. for 1 h. The reaction was concentrated. The residue was re-suspended in THF (15 mL) and added dropwise to a solution of ethyl-3-(dimethylamine)acrylate (2.1 mL, 14.04, 1.1 equiv.) and triethylamine (2.15 mL, 15.44 mmol, 1.1 equiv.) in THF (15 mL). The reaction was stirred at 67° C. for 2 h and cooled to 23° C. (S)-2-amino-3,3-dimethylbutan-1-ol (1.81 g, 15.44 mmol, 1.1 equiv.) was subsequently added and stirred at 23° C. for 30 min. The reaction was quenched with water (40 mL) and ethyl acetate (40 mL). The aqueous layer was extracted with ethyl acetate (2×40 mL), and the organics were dried and concentrated. The compound was purified via silica gel chromatography and concentrated to provide (S)-ethyl 2-(2,6-difluoro-5-iodonicotinoyl)-3-(1-hydroxy-3,3-dimethylbutan-2-ylamino)acrylate Intermediate 80 (4.49 g, 66%). Calcd for $C_{17}H_{21}F_2IN_2O_4$ [M+H]$^+$: 482.9.

Intermediate 81

The following intermediate was prepared by the procedure described in Intermediate 80 from the indicated starting material.

| Int | Compound | Data | SM |
|---|---|---|---|
| 81 | ethyl 2-(2,6-difluoro-5-iodonicotinoyl)-3-(2-(4-methylpiperazin-1-yl)ethylamino)acrylate | Calcd for $C_{18}H_{23}F_2IN_4O_3$ [M + H]$^+$: 409.0 | 2-(4-methylpiperazin-1-yl)ethanamine |

Intermediates 82-90

The following intermediates were prepared by the procedure described in Intermediate 47 with the indicated starting material.

| Int | Compound | Data | SM |
|---|---|---|---|
| 82 | ethyl 6-bromo-1-tert-butyl-4-oxo-1,4-dihydro-1,7-naphthyridine-3-carboxylate | Calcd for $C_{15}H_{17}BrN_2O_3$ [M + H]$^+$: 354.98. | Intermediate 66 & tert-butyl amine |

| Int | Compound | Data | SM |
|---|---|---|---|
| 83 | ethyl 6-bromo-4-oxo-1-(2-(pyrrolidin-1-yl)ethyl)-1,4-dihydro-1,7-naphthyridine-3-carboxylate | Calcd for $C_{17}H_{20}BrN_3O_3$ [M + H]$^+$: 395.95. H$^1$NMR (d$_6$-DMSO) δ 9.24 (s, 1H), 8.82 (s, 1H), 8.15 (s, 1H), 4.92-4.71 (m, 2H), 4.28-4.21 (m, 2H), 3.71-3.58 (m, 2H), 3.18-3.89 (m, 4H), 2.05-1.64 (m, 4H), 1.29 (t, 3H). | Intermediate 66 & 2-(pyrrolidin-1-yl)ethanamine |
| 84 | ethyl 6-bromo-1-ethyl-4-oxo-1,4-dihydro-1,7-naphthyridine-3-carboxylate | Calcd for $C_{13}H_{13}BrN_2O_3$ H$^1$NMR (d$_6$-DMSO) δ 9.18 (s, 1H), 8.78 (s, 1H), 8.03 (s, 1H), 4.55-4.49 (m, 2H), 4.28-4.21 (m, 2H), 1.4 (t, 3H), 1.29 (t, 3H). | Intermediate 66 & ethylamine |
| 85 | ethyl 6-bromo-1-(2-morpholinoethyl)-4-oxo-1,4-dihydro-1,7-naphthyridine-3-carboxylate | Calcd for $C_{17}H_{20}BrN_3O_4$ [M + H]$^+$: 411.95. H$^1$NMR (d$_6$-DMSO) δ 9.29 (s, 1H), 8.84 (s, 1H), 8.16 (s, 1H), 4.95-4.92 (m, 2H), 4.05-3.94 (m, 2H), 3.85-3.76 (m, 2H), 3.62-3.5 (m, 4H), 3.27-3.01 (m, 2H), 1.29 (t, 3H). | Intermediate 66 & 2-morpholinoethanamine |
| 86 | (S)-ethyl 6-bromo-1-(1-hydroxy-3,3-dimethylbutan-2-yl)-4-oxo-1,4-dihydro-1,7-naphthyridine-3-carboxylate | Calcd for $C_{17}H_{21}BrN_2O_4$ [M + H]$^+$: 398.95. | Intermediate 66 and tert-leucinol |

| Int | Compound | Data | SM |
|---|---|---|---|
| 87 | ethyl 6-bromo-4-oxo-1-(pyridin-4-ylmethyl)-1,4-dihydro-1,7-naphthyridine-3-carboxylate | Calcd for C$_{17}$H$_{14}$BrN$_3$O$_3$ [M + H]$^+$: 389.92.<br>H$^1$NMR (d$_6$-DMSO) δ 9.0 (s, 1H), 8.81 (s, 1H), 8.55 (s, 1H), 8.53 (s, 1H), 8.16 (s, 1H), 7.28 (s, 1H), 7.26 (s, 1H), 5.83 (s, 2H), 4.29-4.22 (s, 2H), 1.29 (t, 3H). | Intermediate 66 and pyridin-4-ylmethanamine |
| 88 | ethyl 6-bromo-1-cyclopropyl-4-oxo-1,4-dihydro-1,7-naphthyridine-3-carboxylate | Calcd for C$_{14}$H$_{13}$BrN$_2$O$_3$ [M + H]$^+$: 338.91.<br>H$^1$NMR (d$_6$-DMSO) δ 9.33 (s, 1H), 8.55 (s, 1H), 8.12 (s, 1H), 4.27-4.2 (m, 2H), 3.77-3.75 (m, 1H), 1.3-1.27 (m, 2H), 1.28 (t, 3H), 1.18-1.17 (m, 2H). | Intermediate 66 & cyclopropanamine |
| 89 | (R)-ethyl 6-bromo-1-((1-(tert-butoxycarbonyl)pyrrolidin-3-yl)methyl-4-oxo-1,4-dihydro-1,7-naphthyridine-3-carboxylate | Calcd for C$_{21}$H$_{26}$BrN$_3$O$_3$ [M + H]$^+$: 481.99. | Intermediate 66 & (R)-tert-butyl 3-(aminomethyl)pyrrolidine-1-carboxylate |
| 90 | (S)-ethyl 6-bromo-1-((1-(tert-butoxycarbonyl)pyrrolidin-3-yl)methyl-4-oxo-1,4-dihydro-1,7-naphthyridine-3-carboxylate | Calcd for C$_{21}$H$_{26}$BrN$_3$O$_5$ [M + H]$^+$: 481.99. | Intermediate 66 & (S)-tert-butyl 3-(aminomethyl)pyrrolidine-1-carboxylate |

Intermediate 91

Ethyl 6-bromo-1-(1-methylazetidin-3-yl)-4-oxo-1,4-dihydro-1,7-naphthyridine-3-carboxylate

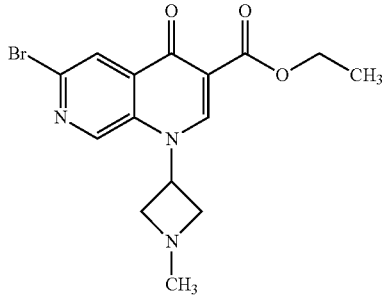 [SMILES: CCOC(=O)c1cn(C2CN(C)C2)c2cnc(Br)cc2c1=O]

To a solution of ethyl 2-(2-bromo-5-fluoroisonicotinoyl)-3-(dimethylamino)acrylate (Intermediate 66, 0.690 g, 2 mmol, 1 equiv.) in THF (7 mL) was added 1-methylazetidin-3-amine HCl (245 mg, 2 mmol, 1 equiv.) and potassium carbonate (276 mg, 2 mmol, 1 equiv.). This reaction mixture was stirred at 60° C. for 1 h. The reaction mixture was concentrated under reduced pressure and re-suspended in DMF (7 mL). Potassium carbonate (553 mg, 4 mmol, 2 equiv.) was added, and the reaction mixture was stirred at 70° C. for 3 h. The reaction mixture was cooled to room temperature and quenched with water. 1 N HCl was added until pH 4-5 was reached. The precipitate was washed with water and hexanes and dried to provide ethyl 6-bromo-1-(1-methylazetidin-3-yl)-4-oxo-1,4-dihydro-1,7-naphthyridine-3-carboxylate (1.2 g, ≥99%). Calcd for $C_{15}H_{16}BrN_3O_3$ [M+H]$^+$: 367.91.

Intermediate 92

(S)-ethyl 6-bromo-4-oxo-1-((1-propylpyrrolidin-3-yl)methyl)-1,4-dihydro-1,7-naphthyridine-3-carboxylate

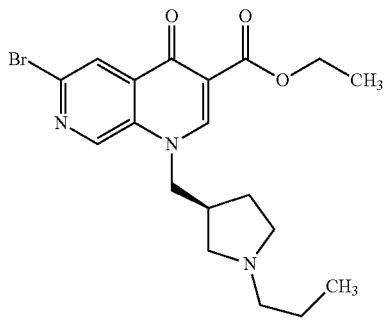 [SMILES: CCCN1CC[C@H](Cn2cc(C(=O)OCC)c(=O)c3cc(Br)ncc32)C1]

To a solution of (S)-ethyl 6-bromo-4-oxo-1-(pyrrolidin-3-ylmethyl)-1,4-dihydro-1,7-naphthyridine-3-carboxylate Intermediate 94 (511.5 mg, 1.2 mmol, 1 equiv.) in acetonitrile (3 mL) and DMF (1 mL) was added iodopropane (0.234 mL, 2.4 mmol, 2 equiv.) followed by potassium carbonate (663 mg, 4.8 mmol, 4 equiv.). The reaction was stirred at 60° C. for 2 days. The reaction was cooled to 23° C. and concentrated. The residue was re-suspended and partitioned between ethyl acetate (10 mL) and water (10 mL). The aqueous layer was extracted with ethyl acetate (2×10 mL), and the organics were dried and concentrated to afford (S)-ethyl 6-bromo-4-oxo-1-((1-propylpyrrolidin-3-yl)methyl)-1,4-dihydro-1,7-naphthyridine-3-carboxylate (211 mg, 38%). Calcd for $C_{19}H_{24}BrN_3O_3$ [M+H]$^+$: 424.0.

$H^1$NMR (d$_6$-DMSO) δ 9.23 (s, 1H), 8.8 (s, 1H), 8.17 (s, 1H), 4.6-4.57 (m, 2H), 4.3-4.23 (m, 2H), 3.74-3.51 (m, 2H), 3.28-3.12 (m, 4H), 2.2-1.97 (m, 2H), 1.87-1.6 (m, 2H), 1.29 (t, 3H), 1.0-0.91 (m, 2H), 0.85 (t, 3H).

Intermediate 93

The following intermediate was prepared by the procedure described in Intermediate 92 with the indicated starting material.

| Int | Compound | Data | SM |
|---|---|---|---|
| 93 | (R)-ethyl 6-bromo-1-((1-ethylpyrrolidin-3-yl)methyl-4-oxo-1,4-dihydro-1,7-naphthyridine-3-carboxylate | Calcd for $C_{18}H_{22}BrN_3O_3$ [M + H]$^+$: 410.0. $H^1$NMR (d$_6$-DMSO) δ 9.18 (s, 1H), 8.35 (s, 1H), 7.95 (s, 1H), 4.82-4.76 (m, 1H), 4.27-4.23 (m, 2H), 3.76-3.61 (m, 4H), 3.26-3.17 (m, 2H), 2.2-1.69 (m, 4H), 1.29 (t, 3H), 1.16 (t, 3H). | Intermediate 95 & iodoethane |

Intermediates 94

The following intermediates were prepared by the procedure described in Intermediate 47 with the indicated starting material.

| Int | Compound | Data | SM |
|---|---|---|---|
| 94 | (S)-ethyl 6-bromo-4-oxo-1-(pyrrolidin-3-ylmethyl)-1,4-dihydro-1,7-naphthyridine-3-carboxylate | Calcd for $C_{16}H_{18}BrN_3O_3$ [M + H]$^+$: 381.94. $H^1$NMR ($d_6$-DMSO) δ 9.27 (s, 1H), 8.87 (s, 1H), 8.15 (s, 1H), 4.77-4.74 (m, 1H), 4.59 (t, 2H), 4.28-4.21 (m, 2H), 3.14-3.05 (m, 2H), 2.1-1.96 (m, 2H), 1.76-1.64 (m 2H), 1.29 (t, 3H). | Intermediate 66 |
| 95 | (R)-ethyl 6-bromo-4-oxo-1-(pyrrolidin-3-ylmethyl)-1,4-dihydro-1,7-naphthyridine-3-carboxylate | Calcd for $C_{16}H_{18}BrN_3O_3$ [M + H]$^+$: 381.95. $H^1$NMR ($d_6$-DMSO) δ 9.27 9 (s, 1H), 8.86 (s, 1H), 8.16 (s, 1H), 4.6-4.56 (m, 1H), 4.28-4.21 (m, 2H), 3.16-2.97 (m, 2H), 2.97-2.81 (m, 2H), 2.08-1.95 (m, 2H), 1.76-1.64 (m, 2H), 1.29 (t, 3H). | Intermediate 66 |

Intermediate 96

2-Bromo-1-(1-methyl-1H-pyrazol-4-yl)ethanone

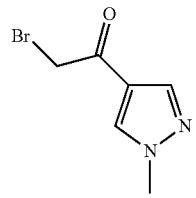

To a solution of 1-(1-methyl-1H-pyrazol-4-yl)ethanone (0.602 g, 4.85 mmol) in chloroform (20 mL) and of 33% HBr in acetic acid (3.92 mg, 0.05 mmol) was added dropwise a chloroform solution containing Br$_2$ (0.262 mL, 5.09 mmol) via an addition funnel. The reaction mixture was stirred at room temperature for 1 h and then concentrated under reduced pressure. The crude solid was triturated in ethyl acetate, filtered, washed and dried in vacuo. The free base was obtained by triturating the product in 5% NaHCO$_3$ for 2 h. The solid that formed were collected by filtration, washed with water and isopropyl alcohol and then dried in vacuo. Isolation gave 874 mg of the title compound.

LC/MS (ES$^+$)(M+H)$^+$: 204 for $C_6H_7BrN_2O$.
$^1$H NMR (300 MHz, d$_6$-DMSO): 3.88 (s, 3H), 4.56 (s, 2H), 7.99 (s, 1H), 8.47 (s, 1H).

Intermediate 97

1-(5-Bromo-4-(4-(1-methyl-1H-pyrazol-4-yl)thiazol-2-yl)pyridin-2-yl)-3-ethylurea

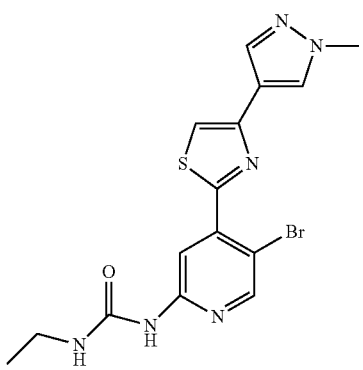 [SMILES: CCNC(=O)Nc1cc(-c2nc(-c3cnn(C)c3)cs2)c(Br)cn1]

In a 25 mL flask 5-bromo-2-(3-ethylureido)pyridine-4-carbothioamide (Intermediate 6, 478 mg, 1.58 mmol) and 2-bromo-1-(1-methyl-1H-pyrazol-4-yl)ethanone (Intermediate 96, 352 mg, 1.73 mmol) were suspended in ethanol (10 mL). The reaction mixture was heated at 80° C. for 12 h, cooled to room temperature and concentrated to one half the volume under reduced pressure. The resulting solids were filtered and washed with acetonitrile. Isolation gave 640 mg of the title compound as an off-white solid.

LC/MS (ES+)(M+H)+: 407, 409 for $C_{15}H_{15}BrN_6OS$.

$^1$H NMR (300 MHz, $d_6$-DMSO): 1.08 (t, 3H), 3.18 (m, 2H), 3.9 (s, 3H), 7.34 (m, 1H), 7.91 (s, 1H), 8.03 (s, 1H), 8.17 (s, 1H), 8.41 (s, 1H), 8.52 (s, 1H), 9.37 (s, 1H).

Intermediate 98

6-(3-ethylureido)-4-(4-(1-methyl-1H-pyrazol-4-yl)thiazol-2-yl)pyridin-3-ylboronic acid

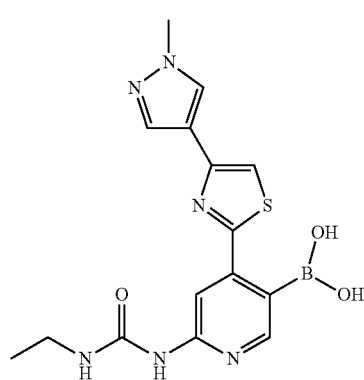 [SMILES: CCNC(=O)Nc1cc(-c2nc(-c3cnn(C)c3)cs2)c(B(O)O)cn1]

In a 100 mL flask 1-(5-bromo-4-(4-(1-methyl-1H-pyrazol-4-yl)thiazol-2-yl)pyridin-2-yl)-3-ethylurea (Intermediate 97, 1.28 g, 3.14 mmol) was dissolved in 1,4-dioxane (15 mL) at 40° C. and degassed with argon. Bis(triphenylphosphine) palladium chloride (0.221 g, 0.31 mmol) was added and allow it to react for 10 minutes while heating at 40° C. 4,4,4',4',5,5,5',5'-octamethyl-2,2'-bi(1,3,2-dioxaborolane) (2.394 g, 9.43 mmol) was added and stirred for 10 minutes while heating at 100° C. Triethylamine (1.314 mL, 9.43 mmol) and potassium acetate (0.925 g, 9.43 mmol) were added and the solution was heated at 100° C. for 15 h. The reaction mixture was cooled to room temperature, filtered through a pad of Celite and partitioned between water and ethyl acetate. The layers were separated and the aqueous layer was back extracted three times with ethyl acetate. The organic layers were combined and washed with water and brine, then dried over sodium sulfate and concentrated under reduced pressure, and purified by column chromatography (Silica gel, 0-10% MeOH in $CH_2Cl_2$). Isolation gave 400 mg of the title compound as an off-white solid.

LC/MS (ES+)[(M+H)+]: 373 for $C_{15}H_{12}BN_6O_3S$.

$^1$H NMR (300 MHz, $d_6$-DMSO): 1.10 (t, 3H), 3.20 (m, 2H), 3.9 (s, 3H), 7.81 (m, 1H), 7.84 (s, 1H), 7.91 (s, 1H), 7.92 (s, 1H), 8.12 (s, 1H), 8.33 (s, 1H), 8.37 (s, 2H), 9.27 (s, 1H).

Intermediate 99 ethyl 6-(6-(3-ethylureido)-4-(4-(1-methyl-1H-pyrazol-4-yl)thiazol-2-yl)pyridin-3-yl)-1-((1-methyl-1H-imidazol-4-yl)methyl)-4-oxo-1,4-dihydro-1,7-naphthyridine-3-carboxylate

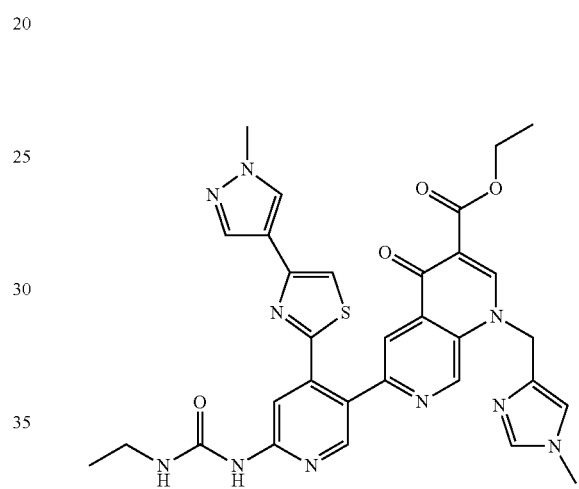

In a microwave vessel, 6-(3-ethylureido)-4-(4-(1-methyl-1H-pyrazol-4-yl)thiazol-2-yl)pyridin-3-ylboronic acid (Intermediate 98, 0.2 g, 0.54 mmol), ethyl 6-bromo-1-((1-methyl-1H-imidazol-4-yl)methyl)-4-oxo-1,4-dihydro-1,7-naphthyridine-3-carboxylate (Intermediate 102, 0.21 g, 0.54 mmol) and cesium carbonate (0.229 g, 0.70 mmol) were combined and suspended in a mixture of dioxane and water (5:1; 2.5 mL/0.5 mL). The suspension was degassed and purged with nitrogen. Pd(PPh$_3$)$_4$ (0.05 g, 0.04 mmol) was added and the mixture was degassed and purged a second time. The reaction mixture was heated in the microwave at 90° C. for 90 minutes. The reaction was partitioned between water and ethyl acetate, the layers were separated, and the organic phase was washed with saturated NaHCO$_3$, water and brine, then dried over magnesium sulfate, and concentrated. The resulting solids were filtered, washed with acetonitrile followed by chloroform. Isolation gave 90 mg of the title compound as an off-white solid.

LC/MS (ES+)[(M+H)+]: 639 for $C_{31}H_{30}N_{10}O_4S$.

Intermediate 100

The following intermediate was prepared in accordance to the procedure described for Intermediate 76 using the starting materials indicated in the table.

| Int | Compound | Data | SM |
|---|---|---|---|
| 100 | ethyl 1-ethyl-6-(6-(3-ethylureido)-4-(4-(trifluoromethyl)thiazol-2-yl)pyridin-3-yl)-7-fluoro-4-oxo-1,4-dihydro-1,8-naphthyridine-3-carboxylate | LC/MS (ES$^+$)[(M + H)$^+$]: 579 for $C_{25}H_{22}F_4N_6O_4S$. | Intermediate 9, ethyl 1-ethyl-7-fluoro-6-iodo-4-oxo-1,4-dihydro-1,8-naphthyridine-3-carboxylate Intermediate 103, diacetoxypalladium, 1,1-bis(di-t-butphosphino)ferrocene, K2CO3, acetonitrile, water |

Intermediates 101

The following intermediates were prepared in accordance to the procedure described for Example 59 using the starting materials indicated in the table.

| Int | Compound | Data | SM |
|---|---|---|---|
| 101 | ethyl 7-(3-tert-butoxycarbonylamino)pyrrolidin-1-yl)-1-ethyl-6-(6-(3-ethylureido)-4-(4-(trifluoromethyl)thiazol-2-yl)pyridin-3-yl)-4-oxo-1,4-dihydro-1,8-naphthyridine-3-carboxylate | LC/MS (ES$^+$)[(M + H)$^+$]: 745 for $C_{34}H_{39}F_3N_8O_6S$. | ethyl 1-ethyl-6-(6-(3-ethylureido)-4-(4-(trifluoromethyl)thiazol-2-yl)pyridin-3-yl)-7-fluoro-4-oxo-1,4-dihydro-1,8-naphthyridine-3-carboxylate Intermediate 100, tert-butyl pyrrolidin-3-ylcarbamate, THF |

Intermediate 102

The following intermediates were prepared in accordance to the procedure described for Intermediate 82 using the starting materials indicated in the table.

| Int | Compound | Data | SM |
|---|---|---|---|
| 102 | ethyl 6-bromo-1-((1-methyl-1H-imidazol-4-yl)methyl)-4-oxo-1,4-dihydro-1,7-naphthyridine-3-carboxylate | LC/MS (ES$^+$)[(M + H)$^+$]: 391, 393 for $C_{16}H_{15}BrN_4O_3$. $^1$H NMR (300 MHz, d$_6$-DMSO): 1.29 (t, 3H), 3.60 (s, 3H), 4.27 (m, 2H), 5.55 (s, 2H), 7.32 (s, 1H), 7.53 (s, 1H), 8.12 (s, 1H), 8.9 (s, 1H), 9.29 (s, 1H). | Intermediate 66 & 1-(1-methyl-1-H-imidazol-4-yl)methanamine |

Intermediate 103

The following intermediates were prepared in accordance to the procedure described for Intermediate 78 using the starting materials indicated in the table.

| Int | Compound | Data | SM |
|---|---|---|---|
| 103 | ethyl 1-ethyl-7-fluoro-6-iodo-4-oxo-1,4-dihydro-1,8-naphthyridine-3-carboxylate | LC/MS (ES$^+$)[(M + H)$^+$]: 391 for $C_{13}H_{12}FIN_2O_3$. $^1$H NMR (300 MHz, d$_6$-DMSO): 1.29 (t, 3H), 1.35 (t, 3H), 4.23 (m, 2H), 4.34 (m, 2H), 8.82 (s, 1H), 8.92 (d, 1H). | Intermediate 104 & $K_2CO_3$ |

Intermediate 104

The following intermediates were prepared in accordance to the procedure described for Intermediate 80 using the starting materials indicated in the table.

| Int | Compound | Data | SM |
|---|---|---|---|
| 104 | Ethyl-1-2-[(2,6-difluoro-5-iodopyridin-3-yl)carbonyl]-3-(ethylamino)pro-2-enoate 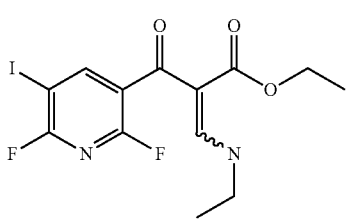 | LC/MS (ES$^+$)[(M + H)$^+$]: 410 for $C_{13}H_{13}F_2IN_2O_3$. | 2,6-difluoro-5-iodocotinic acid, thionyl chloride, ethyl-3-(dimethylamine)acrylate, triethylamine & ethylamine |

Intermediate 105

The following intermediates were prepared in accordance to the procedure described for Example 59 using the starting materials indicated in the table.

| Int | Compound | Data | SM |
|---|---|---|---|
| 105 | 7-(3-tert-butoxycarbonylamino)pyrrolidin-1-yl)-6-(6-(3-ethylureido-4-(4-(trifluoromethyl)thiazol-2-yl)pyridin-3-yl)-1-((S)-1-hydroxy-3,3-dimethylbutan-2-yl)-4-oxo-1,4-dihydro-1,8-naphthyridine-3-carboxylic acid 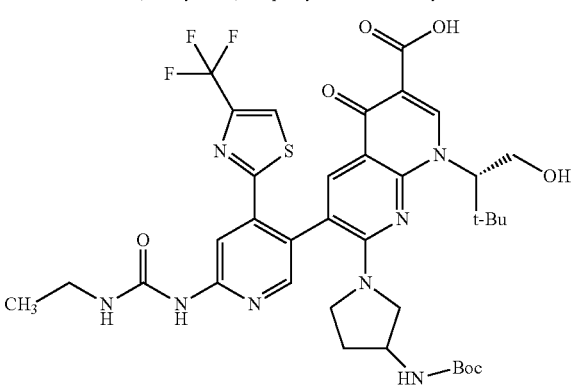 | Calcd for $C_{31}H_{35}F_3N_8O_5S$ [M + H]$^+$: 789.3. | Intermediate 76, 3-(tert-butoxycarbonylamino)-pyrrolidine, LiOH, & HCl. |

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

The invention claimed is:
1. A compound of formula (IA):

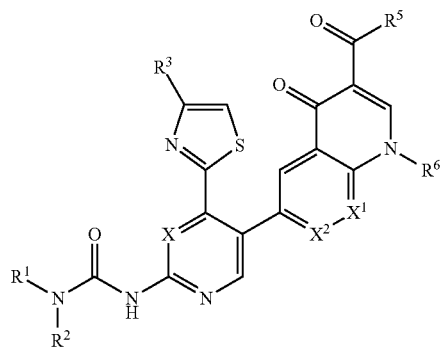

(IA)

or a pharmaceutically acceptable salt thereof, wherein:
X is CH;
$X^1$ is N;
$X^2$ is $CR^{24}$;
$R^1$ is ethyl;
$R^2$ is hydrogen
$R^3$ is trifluouromethyl or phenyl;
$R^5$ is selected from —OH, ethoxy, 2-hydroxyethoxy, 3-hydroxypropoxy, 2-(phosphonooxy)ethoxy, 3-(phosphonooxy)propoxy, and 2-{[bis(benzyloxy)phosphoryl]oxy}ethoxy;
$R^6$ is selected from hydrogen, $C_{1-6}$alkyl, $C_{3-14}$carbocyclyl-L and heterocyclyl-L-;
wherein said $C_{1-6}$alkl, $C_{3-14}$carbocyclyl-L-, or heterocyclyl-L- are optionally substituted with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$;
$R^{16}$ is a substituent on carbon which, for each occurrence, is independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N—$(C_{1-6}$alkyl)sulphamoyl, N,N—$(C_{1-6}$alkyl)$_2$sulphamoyl, $C_{1-6}$alkylsulphonylamino, $C_{3-6}$carbocyclyl, heterocyclyl and —OP(=O)(OR$^a$)$_2$, wherein R$^a$, for each occurrence is independently H or a $C_{1-6}$alkyl; wherein said carbamoyl, $C_{1-6}$alkyl, $C_{2-6}$alkenyl, $C_{2-6}$alkoxy, $C_{1-6}$alkanoyl, $C_{1-6}$alkanoyloxy, N—$(C_{1-6}$alky)amino, N N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl $C_{1-6}$alkylS(O)$_a$-wherein a is 0, 1 or 2, $C_{1-6}$alkoxcarbonyl, $C_{1-6}$alkoxy carbonylamino, N—$(C_{1-6}$alkyl)sulphamoyl, N,N—$(C_{1-6}$alkyl)$_2$sulphamoyl, $C_{1-6}$alkysulphonylamino, $C_{3-6}$carbocyclyl and heterocyclyl independently of each other may be optionally substituted on one or more carbon by one or more $R^{19}$; and wherein if said heterocyclyl contains an —NH— moiety that nitrogen may be optionally substituted by a group selected from $R^{20}$; and wherein if said heterocyclyl contains an =N— or a —S— moiety that nitrogen may be optionally substituted by one oxo group and that sulfur may be optionally substituted by one or two oxo groups;

$R^{17}$ and $R^{20}$, for each occurrence, are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—$(C_{1-6}$alkyl)carbamoyl, N,N—$(C_{1-6}$alkyl)carbamoyl, benzyl, benzyloxycarbonyl, benzoyl and phenylsulphonyl; wherein said $C_{1-6}$alkyl $C_{3-6}$cycloalky, $C_{1-6}$alkanoyl, $C_{1-6}$alkylsulphonyl, $C_{1-6}$alkoxycarbonyl, carbamoyl, N—$(C_{1-6}$alkyl)carbamoyl, N,N—$(C_{1-6}$alkyl)carbamoyl, benzyl, benzyloxycarbonyl, benzoyl and phenylsuphonyl independently of each other may be optionally substituted on carbon by one or more $R^{23}$;

$R^{19}$ and $R^{23}$, for each occurrence, are independently selected from halo, nitro, cyano, hydroxy, trifluoromethoxy, trifluoromethyl, phenyl, morpholinyl, piperazinyl, piperidinyl, amino, carboxy, carbamoyl, mercapto, sulphamoyl, $C_{1-6}$alkyl, $C_{1-6}$alkoxy, acetyl, acetoxy, methylamino, ethylamino, dimethylamino, diethylamino, dipropylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl;

$R^{24}$ is selected from hydrogen, halo, nitro, cyano, hydroxy, amino, mercapto, heterocyclyl, $C_{1-6}$alkyl, $C_{2-6}$alkenyl, $C_{2-6}$alkenyl, $C_{1-6}$alkoxy, N—$(C_{1-6}$alkyl)amino, N,N—$(C_{1-6}$alkyl)$_2$amino, and $C_{1-6}$alkylsulfanyl; wherein said heterocyclyl, $C_{1-6}$alkyl, $C_{2-6}$alkenyl, $C_{2-6}$alkynyl, $C_{1-6}$alkoxy, N—$C_{1-6}$alkyl)amino, N,N—$(C_{1-6}$alkyl)$_2$amino and $C_{1-6}$alkylsulfanyl may be optionally substituted on one or more carbon by one or more $R^{25}$; wherein if said heterocyclyl contains an —NH—moiety that nitrogen may be optionally substituted by $C_{1-6}$alkyl;

$R^{25}$ is a substituent on carbon which, for each occurrence, is independently selected from halo, nitro, cyano, hydroxy, amino, carboxy, carbamoyl, mercapto, sulphamoyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N—$(C_{1-6}$alkyl)sulphamoyl, N,N—$(C_{1-6}$alkyl)$_2$sulphamoyl, $C_{1-6}$alkylsulphonylamino, $C_{3-6}$carbocyclyl and heterocyclyl; wherein said carbamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino N—$(C_{1-6}$alkyl)sulphamoyl, N,N—$(C_{1-6}$alkyl)$_2$sulphamoyl, $C_{1-6}$alkylsulphonylamino, $C_{3-6}$carbocyclyl and heterocyclyl may be optionally substituted on one or more carbon by one or more $R^{26}$; and wherein if said heterocyclyl contains an —NH— moiety that nitrogen may be optionally substituted by a group selected from $R^{27}$; and wherein if said heterocyclyl contains an =N— or a —S— moiety that nitrogen may be optionally substituted by one oxo group and that sulfur may be optionally substituted by one or two oxo groups;

$R^{26}$ and $R^{28}$, for each occurrence, are independently selected from halo, nitro, cyano, hydroxy, trifluoromethoxy, trifluoromethyl, amino, carboxy, carbamoyl, mercapto, sulphamoyl, $C_{1-6}$alkyl, $C_{1-6}$alkoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl;

$R^{27}$, for each occurrence, is independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulphonyl; wherein said $C_{1-6}$alkyl, $C_{3-6}$cycloalkyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulphonyl may be optionally substituted on carbon by one or more $R^{28}$; and L is a direct bond or a $C_{1-6}$alkylene.

2. The compound of claim 1, or a pharmaceutically acceptable salt thereof, wherein $R^6$ is a $C_{1-6}$alkyl which is substituted on one or more carbon atoms with one or more independently selected $R^{16}$.

3. The compound of claim 2, wherein $R^6$, or a pharmaceutically acceptable salt thereof, is selected from 2-hydroxyethyl, ethyl, 1,3-dimethoxypropan-2-yl, 3,3-dimethylbutyl, 2-methoxyethyl, 1-hydroxy-4-methyl-pentan-2-yl, 2-(N,N-dimethylamino)-ethyl, 1-hydroxy-3,3-dimethyl-butan-2-yl, 2-(phosphonooxy)ethoxy, 1-(phosphonooxy)-4-methyl-pentan-2-yl, 2-{[bis(benzyloxy)phosphoryl]oxy}ethyl and 1-{[(benzyloxy)(hydroxy)phosphoryl]oxy}-4-methyl-penan-2-yl.

4. The compound of claim 1, or a pharmaceutically acceptable salt thereof, wherein $R^6$ is $C_{3-6}$cycloalkyl.

5. The compound of claim 1, or a pharmaceutically acceptable salt thereof, wherein $R^6$ is a heterocyclyl-L-; wherein said heterocyclyl is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$.

6. The compound of claim 5, or a pharmaceutically acceptable salt thereof, wherein $R^6$ is selected from 2-(1-methyl-piperidin-4-yl)-ethyl, 1-ethylpyrrolidin-2-yl)methyl, (1-methyl-1 H-imidazol-4-yl)methyl, 2-morpholinopropyl, (2-(diethylamino)ethyl)piperidin-3-yl, cyclohexyl, 1-(2-morpholino-ethyl)-piperidin-3-yl, 1-methyl -piperidin-4-ylmethyl and 1-(tert-butoxycarbonyl)-piperidin-3-yl, piperidin-3-yl.

7. The compound of claim 1, or a pharmaceutically acceptable salt thereof, represented by the following formula:

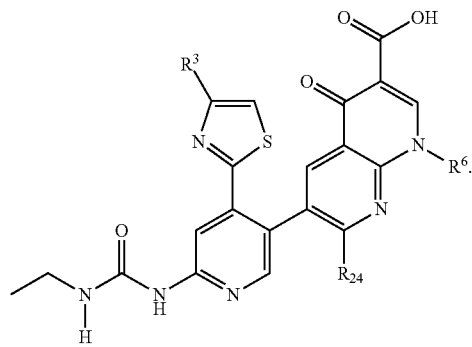

8. A pharmaceutical composition comprising a compound of claim 1, or a pharmaceutically acceptable salt thereof, and a pharmaceutically acceptable excipient or carrier.

9. The compound of claim 1, wherein the compound is selected from the group consisting of:

Ethyl 6-{6-[(ethylcarbamoyl)amino]-4-[4-(trifluoromethyl)-1,3-thiazol-2-yl]pyridin-3-yl}-1-(2-hydroxyethyl)-4-oxo-1,4-dihydro-1,8-naphthyridine-3-carboxylate;

Ethyl 1-cyclopropyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate;

Ethyl 6-{6-[(ethylcarbamoyl)amino]-4-[4-(trifluoromethyl)-1,3-thiazol-2-yl]pyridin-3-yl}-1-[(2S)-1-hydroxy-4-methylpentan-2-yl]-4-oxo-1,4-dihydro-1,8-naphthyridine-3-carboxylate;

Ethyl 6-{6-[(ethylcarbamoyl)amino]-4-[4-(trifluoromethyl)-1,3-thiazol-2-yl]pyridin-3-yl}-1-[(2S)-1-hydroxy-3,3-dimethylbutan-2-yl]-4-oxo-1,4-dihydro-1,8-naphthyridine-3-carboxylate;

1-Ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid;

1-Cyclopropyl-6-{6-[(ethylcarbamoyl)amino]-4-[4-(trifluoromethyl)-1,3-thiazol-2-yl]pyridin -3-yl}-4-oxo-1,4-dihydro-1,8-naphthyridine-3-carboxylic acid;

6-{6-[(ethylcarbamoyl)amino]-4-[4-(trifluoromethyl)-1,3-thiazol-2-yl]pyridin-3-yl}-1-(2-hydroxyethyl)-4-oxo-1,4-dihydro-1,8-naphthyridine-3-carboxylic acid;

6-{6-[(ethylcarbamoyl)amino]-4-[4-(trifluorornethyl)-1,3-thiazol-2-yl]pyridin-3-yl}1-1-[(2S)-1-hydroxy-4-methylpentan-2-yl]-4-oxo-1,4-dihydro-1,8-naphthyridine-3-carboxylic acid;

6-{6-[(ethylcarbamoyl)amino]-4-[4-(trifluorornethyl)-1,3-thiazol-2-yl]pyridin-3-yl}1-1-[(2S)-1-hydroxy-3,3-dimethylbutan-2-yl]-4-oxo-1,4-dihydro-1,8-naphthyridine-3-carboxylic acid;

1-(2-{[bis(benzyloxy)phosphoryl]oxy}ethyl)-6-{6-[(ethylcarbamoyl)amino]-4-[4-(trifluoromethyl)-1,3-thiazol-2-yl]pyridin-3-yl}1-4-oxo-1,4-dihydro-1,8-naphthyridine-3-carboxylic acid;

6-{6-[(ethylcarbamoyl)amino ]-4-[4-(trifluorornethyl)-1,3-thiazol-2-yl]pyridin-3-yl}-4-oxo-1-[2-(phosphonooxy)ethyl]-1,4-dihydro-1,8-naphthyridine-3-carboxylic acid;

Ethyl 1[2-(dimethylamino)ethyl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate;

1-[2-(dimethylamino)ethyl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid;

2-hydroxyethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate;

3-hydroxypropyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate;

2-{[bis(benzyloxy)phosphoryl]oxy}ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate;

2-(phosphonooxy)ethyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate;

3-{[Bis(benzyloxy)phosphoryl]oxy}propyl 1-ethyl-6-{6-[(ethylcarbamoyl)amino]-4-[4-(trifluoromethyl)-1,3-thiazol-2-yl]pyridin-3-yl}-4-oxo-1,4-dihydro-1,8-thianaphthyridine-3-carboxylate;

3-(Phosphonooxy)propyl 1-ethyl-6-{6-[(ethylcarbamoyl)amino]-4-[4-(trifluorornethyl)-1,3-thiazol-2-yl]pyridin-3-yl}-4-oxo-1,4-dihydro-1,8-naphthyridine-3-carboxylate;

Ethyl 1-[(2S)-1-{[(benzyloxy)(hydroxy)phosphoryl]oxy}-4-methylpentan-2-yl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylate;

1-[(2S)-1-{[(benzyloxy)(hydroxy)phosphoryl]oxy}-4-methylpentan-2-yl]-6-{6-[(ethylcarbamoyl)amino]-4-[4-(trifluoromethyl)-1,3-thiazol-2-yl]pyridin-3-yl}-4-oxo-1,4-dihydro-1,8-naphthyridine-3-carboxylic acid;

6-{6-[(ethylcarbamoyl)amino]-4-[4-(trifluorornethyl)-1,3-thiazol-2-yl]pyridin-3-yl}-1-[(2S)-4-methyl-1-(phosphonooxy)pentan-2-yl]-4-oxo-1,4-dihydro-1,8-naphthyridine-3-carboxylic acid;

(R)-ethyl 1-(1-(tert-butoxycarbonyl)piperidin-3-yl)-6-(6-(3-ethylureido)-4-(4-(trifluoromethypthiazol-2-yl)pyridin-3-yl)-4-oxo-1,4-dihydro-1,8-naphthyridine-3-carboxylate;

(R)-ethyl 6-(6-(3-ethylureido)-4-(4-(trifluoromethypthiazol-2-yl)pyridin-3-yl)-4-oxo-1-(piperidin-3-yl)-1,4-dihydro-1,8-naphthyridine-3-carboxylate;

(R)-ethyl 6-(6-(3-ethylureido)-4-(4-(trifluoromethypthiazol-2-yl)pyridin-3-yl)-1-(1-(2-morpholinoethyl)piperidin-3-yl)-4-oxo-1,4-dihydro-1,8-naphthyridine-3-carboxylat;

(R)-ethyl 6-(6-(3-ethylureido)-4-(4-(trifluoromethypthiazol-2-yl)pyridin-3-yl)-1-(1-(2-morpholinoethyl)piperidin-3-yl)-4-oxo-1,4-dihydroquinoline-3-carboxylic acid;

Ethyl 1-(2-{[bis(benzyloxy)phosphoryl]oxy}ethyl)-6-{6-[(ethylcarbamoyl)amino]-4-[4-(trifluoromethyl)-1,3-thiazol-2-y}-4-oxo-1,4-dihydro-1,8-naphthyridine-3-carboxylate;

(S)-6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydro-1,8-naphthyridine-3-carboxylic acid;

(S)-1-((1-ethylpyrrolidin-2-yl)methyl)-6-(6-(3-ethylureido)-4-(4-(trifluoromethyl)thiazol-2-y1)pyridin-3-yl)-4-oxo-1,4-dihydro-1,8-naphthyridine-3-carboxylic acid;

(R)-1-((1-ethylpyrrolidin-2-yl)methyl)-6-(6-(3-ethylureido)-4-(4-(trifluoromethyl)thiazol-2-y1)pyridin-3-yl)-4-oxo-1,4-dihydro-1,8-naphthyridine-3-carboxylic acid;

(S)-1-(1-(2-(diethylamino)ethyl)piperidin-3-yl)-6-(6-(3-ethylureido)-4-(4-isobutylthiazol-2-yl)pyridin-3-yl)-4-oxo-1,4-dihydro-1,8-naphthyridine-3-carboxylic acid;

(S)-1-(1-(2-(diethylamino)ethyl)piperidin-3-yl)-6-(6-(3-ethylureido)-4-(4-phenylthiazol-2-yl)pyridin-3-yl)-4-oxo-1,4-dihydro-1,8-naphthyridine-3-carboxylic acid;

7-(2-(dimethylamino)ethylamino)-1-(((S)-1-ethylpyrrolidin-2-yl)methyl)-6-(6-(3-ethylureido)-4-(4-(trifluoromethypthiazol-2-yl)pyridin-3-yl)-4-oxo-1,4-dihydro-1,8-naphthyridine-3-carboxylic acid;

7-(2-(dimethylamino)ethylamino)-1-ethyl-6-(6-(3-ethylureido)-4-(4-(trifluoromethyl)thiazol -2-yl)pyridin-3-yl)-4-oxo-1,4-dihydro-1,8-naphthyridine-3-carboxylic acid;

1-ethyl-6-(6-(3-ethylureido)-4-(4-(trifluoromethyl)thiazol-2-yl)pyridin-3-yl)-7-(4-methylpiperazin-1-yl)-4-oxo-1,4-dihydro-1,8-naphthyridine-3-carboxylic acid;

(R)-1-(1-(2-(diethylamino)ethyl)piperidin-3-yl)-6-(6-(3-ethylureido)-4-(4-(trifluoromethypthiazol-2-yl)pyridin-3-yl)-4-oxo-1,4-dihydro-1,8-naphthyridine-3-carboxylic acid;

1-(1,3-dimethoxypropan-2-yl)-6-(6-(3-ethylureido)-4-(4-(trifluoromethyl)thiazol-2-yl)pyridin-3-yl)-4-oxo-1,4-dihydro-1,8-naphthyridine-3-carboxylic acid;

6-(6-(3-ethylureido)-4-(4-(trifluoromethyl)thiazol-2-yl)pyridin-3-yl)-1-(2-morpholinoethyl)-4-oxo-1,4-dihydro-1,8-naphthyridine-3-carboxylic acid;

ethyl 6-(6-(3-ethylureido)-4-(4-(trifluoromethyl)thiazol-2-yl)pyridin-3-yl)-1-(1-methylazetidin-3-yI)-4-oxo-1,4-dihydro-1,8-naphthyridine-3-carboxylate;

(S)-1-((1-ethylpyrrolidin-2-yl)methyl)-6-(6-(3-ethylureido)-4-(4-(trifluoromethyl)thiazol-2-y1)pyridin-3-yl)-7-(4-methylpiperazin-1-yl)-4-oxo-1,4-dihydro-1,8-naphthyridine-3-carboxylic acid;

(S)-6-(6-(3-ethylureido)-4-(4-(trifluoromethyl)thiazol-2-yl)pyridin-3-yl)-1-(1-hydroxy-3,3-dimethylbutan-2-yl)-7-(4-methylpiperazin-1-yl)-4-oxo-1,4-dihydro-1,8-naphthyridine-3-carboxylic acid;

(S)-7-(3-(aminomethyl)pyrrolidin-1-yl)-6-(6-(3-ethylureido)-4-(4-(trifluoromethyl)thiazol-2-yl)pyridin-3-yl)-1-(2-(4-methylpiperazin-1-yl)ethyl)-4-oxo-1,4-dihydro-1,8-naphthyridine-3-carboxylic acid;

(S)-7-(3-aminopyrrolidin-1-yl)-6-(6-(3-ethylureido)-4-(4-(trifluoromethyl)thiazol-2-yl)pyridin-3-yl)-1-(2-(4-methylpiperazin-1 -yl)ethyl)-4-oxo-1 ,4-dihydro-1 ,8-naphthyridine-3-carboxylic acid;

7-(3-aminopyrrolidin-1-yl)-1-ethyl-6-(6-(3-ethylureido)-4-(4-(trifluoromethyl)thiazol-2-yl)pyridin-3-yl)-4-oxo-1,4-dihydro-1,8-naphthyridine-3-carboxylic acid; and 7-(3-aminopyrrolidin-1-yl)-6-(6-(3-ethylureido)-4-(4-(trifluoromethyl)thiazol-2-yl)pyridin-3-y1)-1-((S)-1-hydroxy-3,3-dimethylbutan-2-yl)-4-oxo-1 ,4-dihydro-1 ,8-naphthyridine-3-carboxylic acid, or a pharmaceutically acceptable salt thereof.

* * * * *